United States Patent
Bueno et al.

(10) Patent No.: US 11,234,732 B2
(45) Date of Patent: Feb. 1, 2022

(54) SYSTEM AND METHOD FOR A TISSUE RESECTION MARGIN MEASUREMENT DEVICE

(71) Applicants: The Brigham and Women's Hospital, Inc., Boston, MA (US); Navigation Sciences, Inc., Brookline, MA (US)

(72) Inventors: Raphael Bueno, Brookline, MA (US); Jayender Jagadeesan, Bedford, MA (US); Alan D. Lucas, Brookline, MA (US)

(73) Assignees: The Brigham and Women's Hospital, Inc., Boston, MA (US); Navigation Sciences, Inc., Brookline, MA (US)

( * ) Notice: Subject to any disclaimer, the term of this patent is extended or adjusted under 35 U.S.C. 154(b) by 0 days.

(21) Appl. No.: 17/420,528

(22) PCT Filed: Oct. 16, 2020

(86) PCT No.: PCT/US2020/056114
§ 371 (c)(1),
(2) Date: Jul. 2, 2021

(87) PCT Pub. No.: WO2021/076987
PCT Pub. Date: Apr. 22, 2021

(65) Prior Publication Data
US 2021/0386449 A1 Dec. 16, 2021

Related U.S. Application Data

(60) Provisional application No. 63/054,921, filed on Jul. 22, 2020, provisional application No. 62/923,137, filed on Oct. 18, 2019.

(51) Int. Cl.
*A61B 17/34* (2006.01)
*A61B 17/32* (2006.01)
(Continued)

(52) U.S. Cl.
CPC ........ *A61B 17/3468* (2013.01); *A61B 17/068* (2013.01); *A61B 17/320016* (2013.01);
(Continued)

(58) Field of Classification Search
CPC .............. A61B 17/3468; A61B 17/068; A61B 17/320016; A61B 34/10; A61B 34/20;
(Continued)

(56) References Cited

U.S. PATENT DOCUMENTS 9,770,262 B2   9/2017 Clancy et al.
9,855,421 B2   1/2018 Garai et al.
(Continued)

OTHER PUBLICATIONS

International Search Report with Written Opinion of International Application No. PCT/US2020/056114, dated Feb. 26, 2021, 31 pages.

*Primary Examiner* — Richard G Louis
(74) *Attorney, Agent, or Firm* — Quarles & Brady LLP

(57) ABSTRACT

Embodiments of the invention provide a system and method for resecting a tissue mass. The system for resecting a tissue mass includes a first sensor for measuring a signal corresponding to the position and orientation of the tissue mass. The first sensor is dimensioned to fit inside of or next to the tissue mass. The system also includes a second sensor attached to a surgical instrument configured to measure the position and orientation of the surgical instrument. A controller is in communication with the first sensor and the second sensor, and the controller executes a stored program to calculate a distance between the first sensor and the second sensor. Accordingly, visual, auditory, haptic or other feedback is provided to the clinician to guide the surgical instrument to the surgical margin.

23 Claims, 43 Drawing Sheets

(51) Int. Cl.
*A61B 34/20* (2016.01)
*A61B 34/10* (2016.01)
*A61B 17/068* (2006.01)
*A61B 90/00* (2016.01)
*A61B 17/00* (2006.01)

(52) U.S. Cl.
CPC .............. *A61B 34/10* (2016.02); *A61B 34/20* (2016.02); *A61B 90/06* (2016.02); *A61B 90/39* (2016.02); *A61B 2017/008* (2013.01); *A61B 2017/00119* (2013.01); *A61B 2017/00809* (2013.01); *A61B 2034/105* (2016.02); *A61B 2034/2051* (2016.02); *A61B 2090/067* (2016.02); *A61B 2090/397* (2016.02); *A61B 2090/3908* (2016.02)

(58) Field of Classification Search
CPC .................... A61B 90/06; A61B 90/39; A61B 2017/00119; A61B 2017/008; A61B 2017/00809; A61B 2034/105; A61B 2034/2051; A61B 2090/067; A61B 2090/3908; A61B 2090/397
See application file for complete search history.

(56) References Cited

U.S. PATENT DOCUMENTS

| | | |
|---|---|---|
| 2008/0188921 A1 | 8/2008 | Yamasaki et al. |
| 2016/0192960 A1 | 7/2016 | Bueno et al. |
| 2018/0256262 A1 | 9/2018 | Duindam et al. |
| 2019/0261886 A1 | 8/2019 | King et al. |

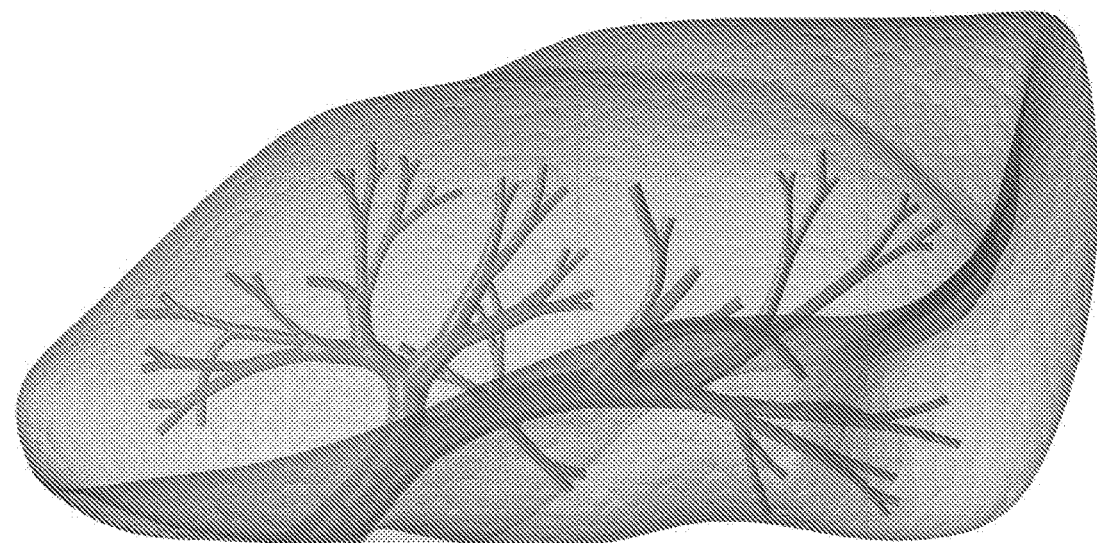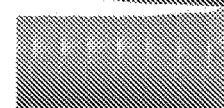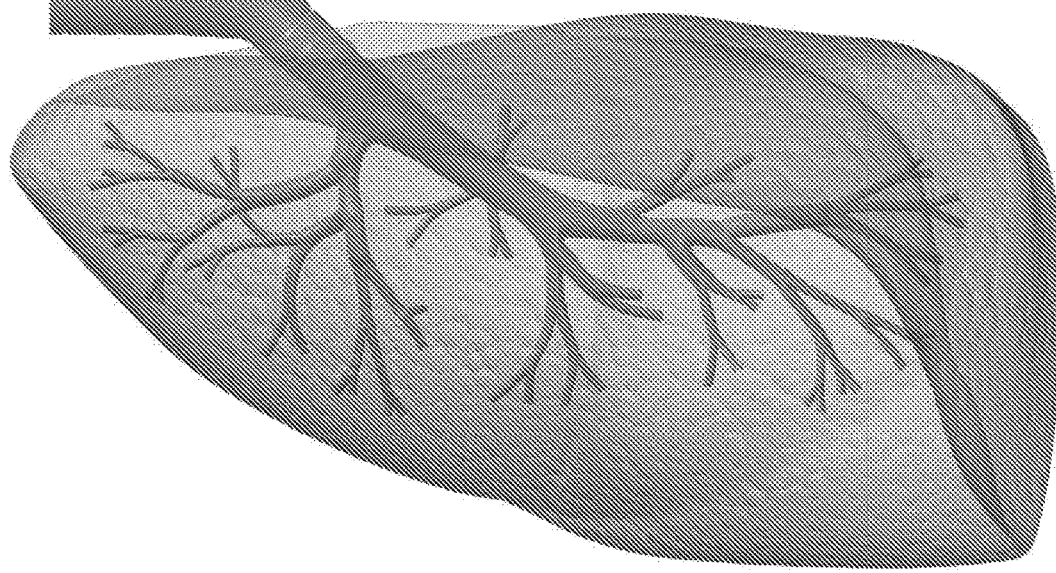
FIG. 12

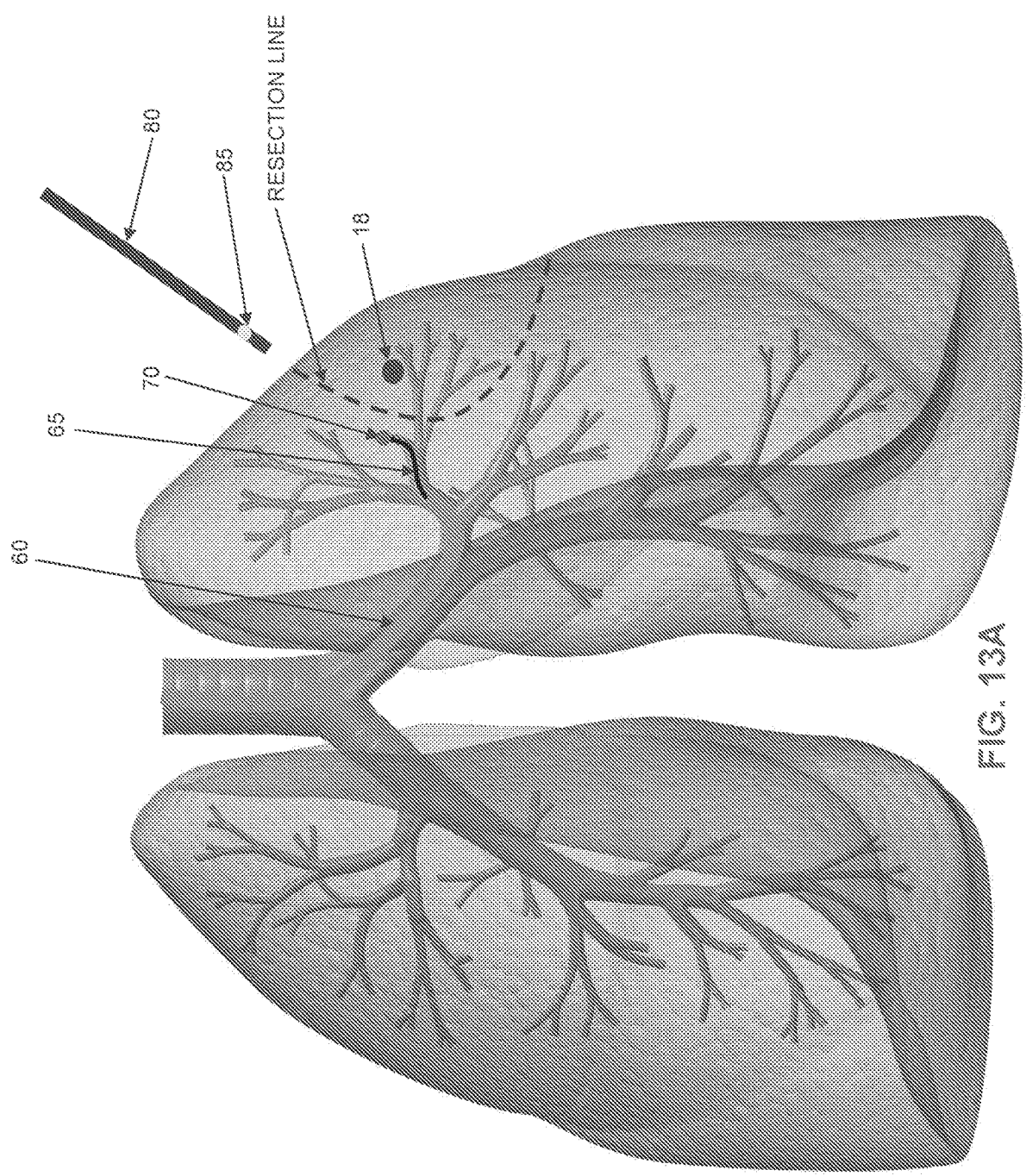

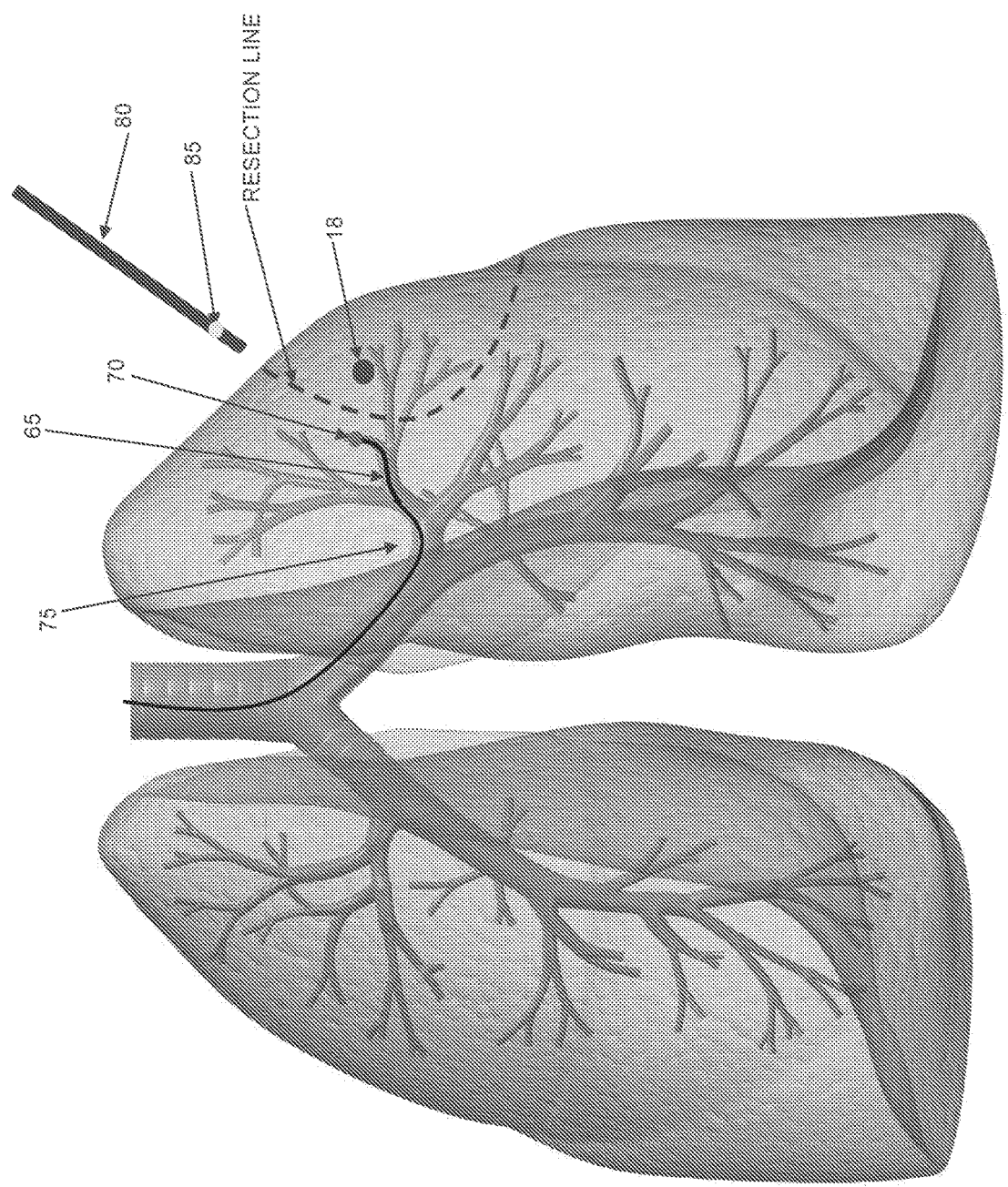

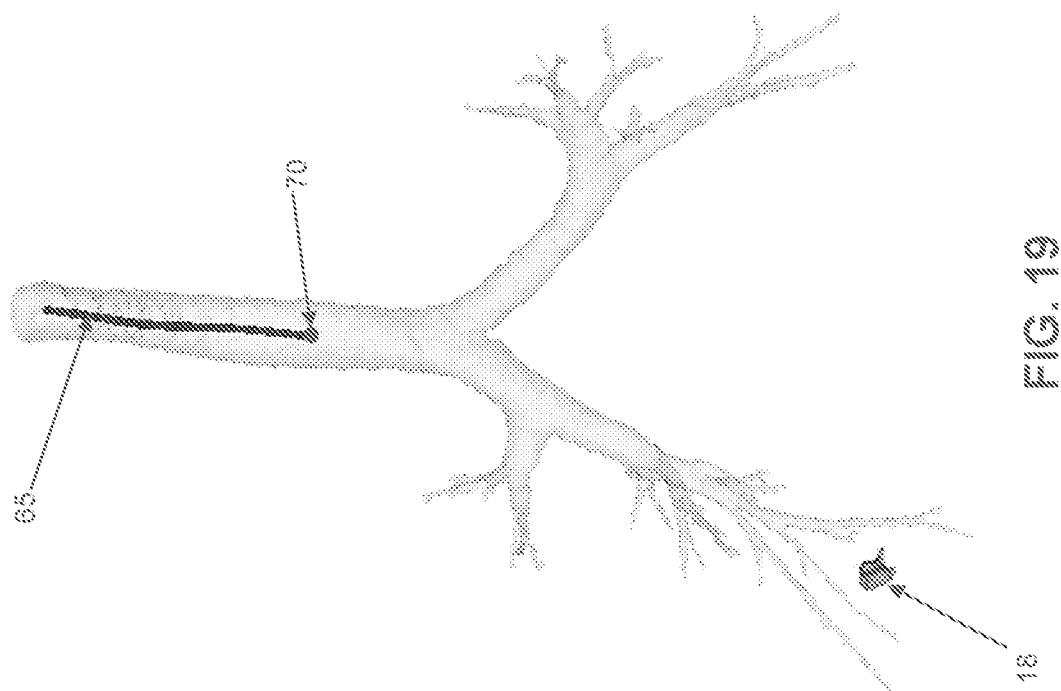
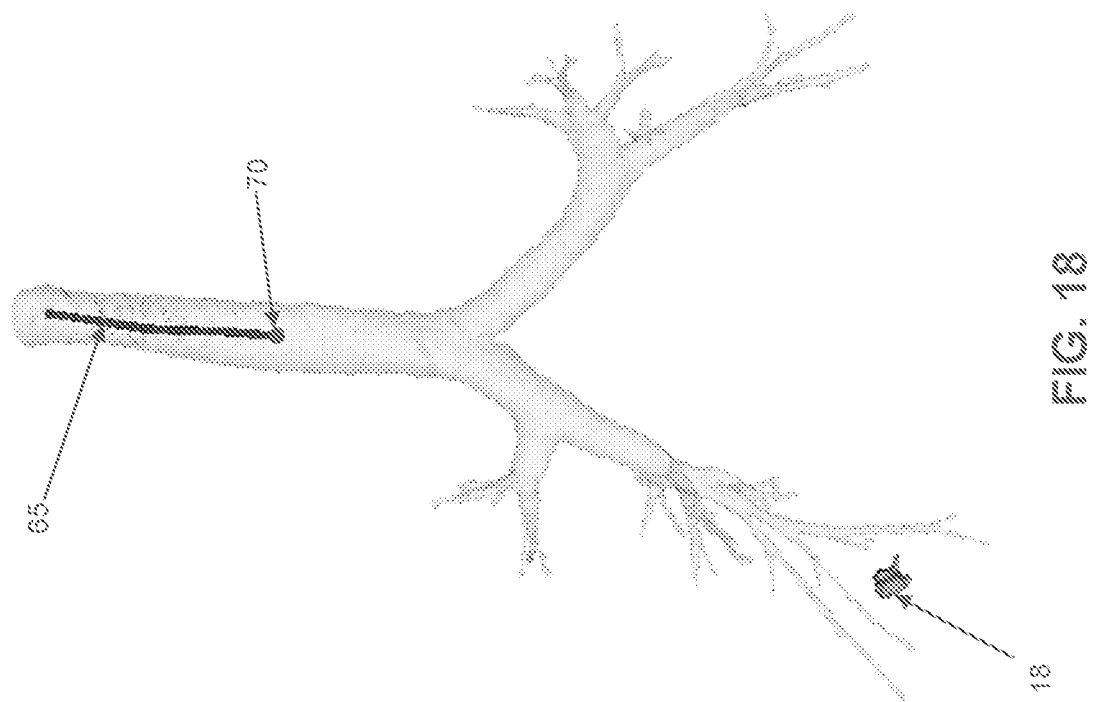

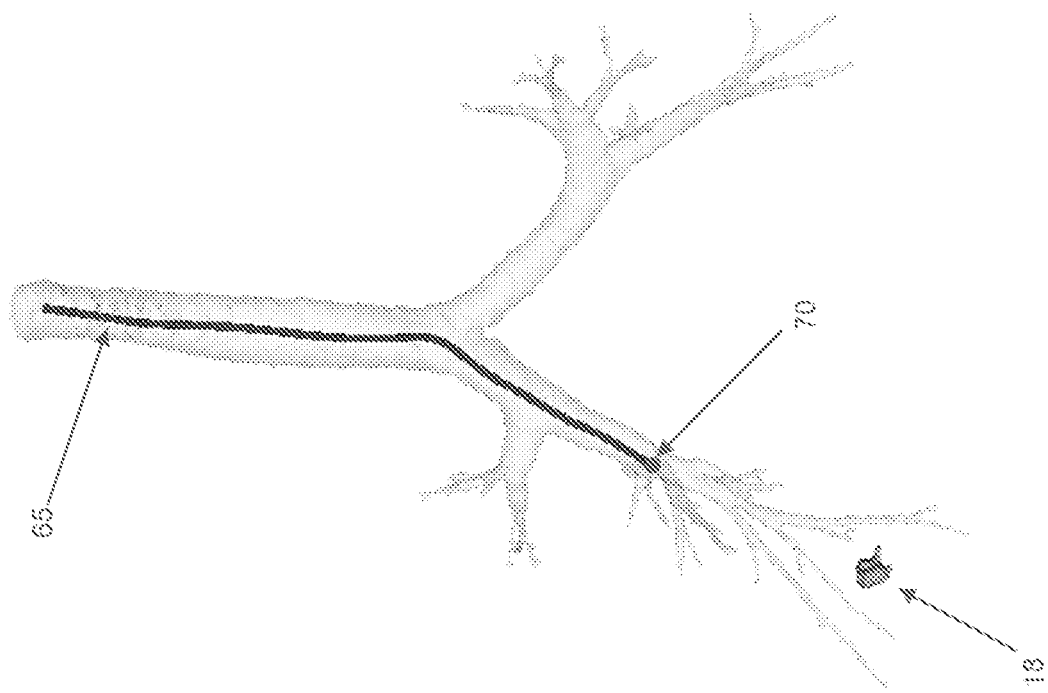
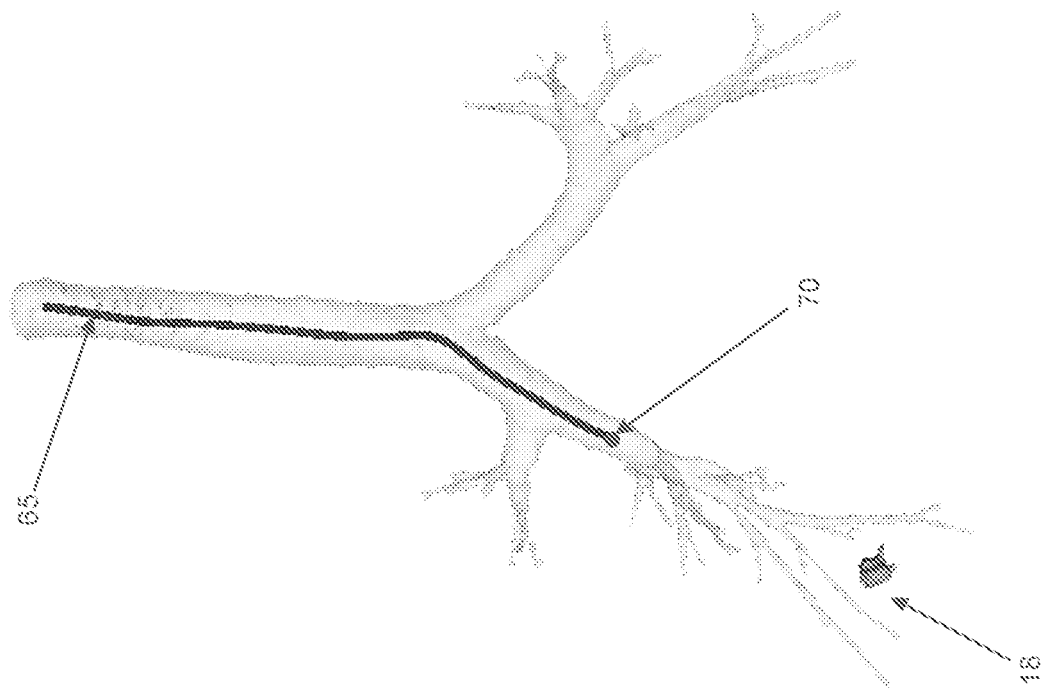

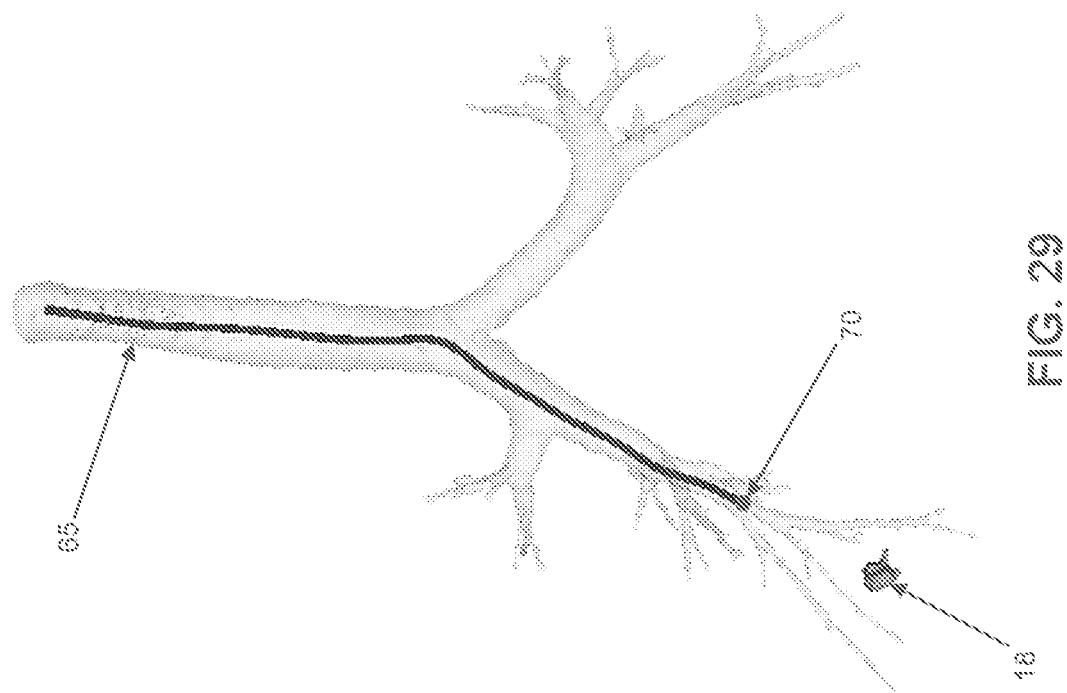
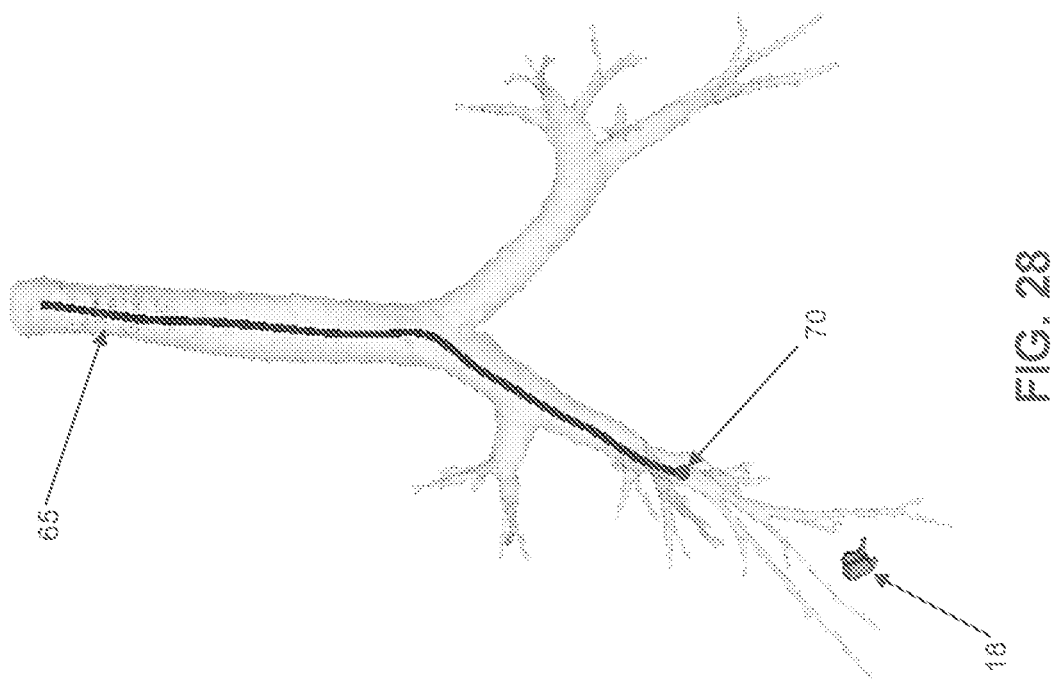

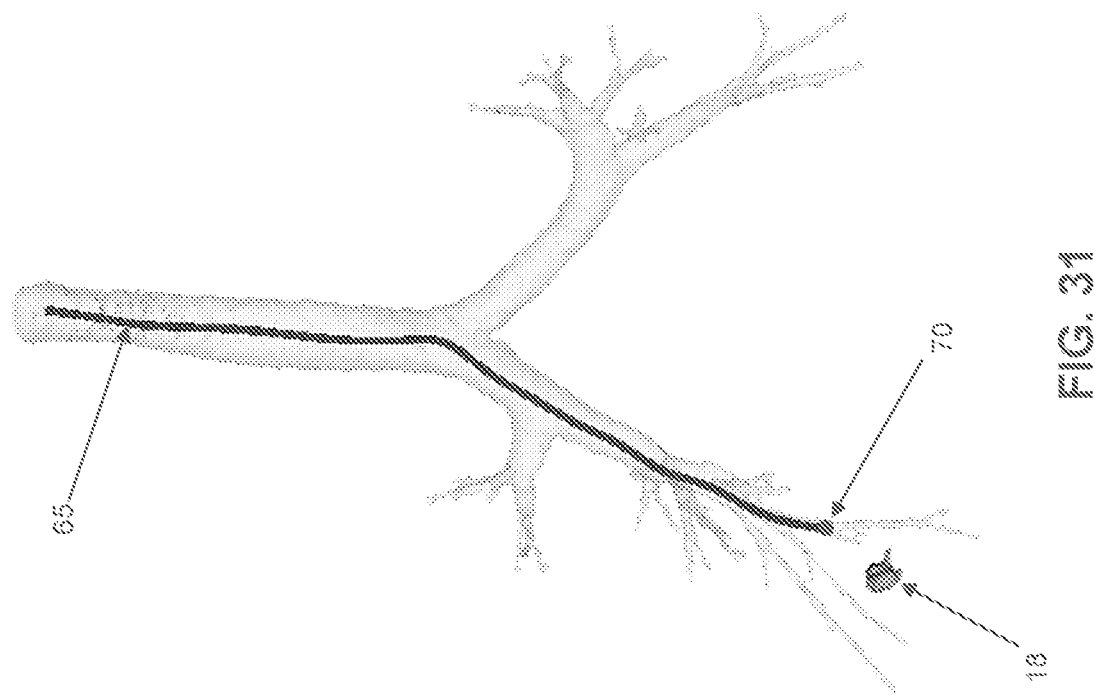
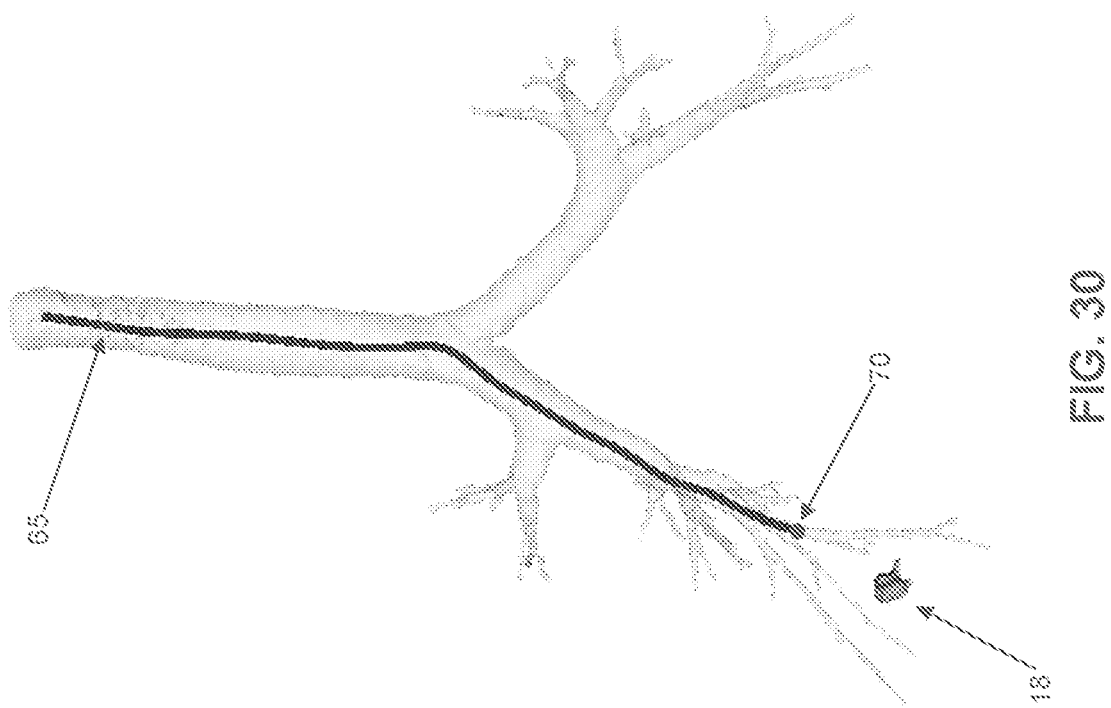

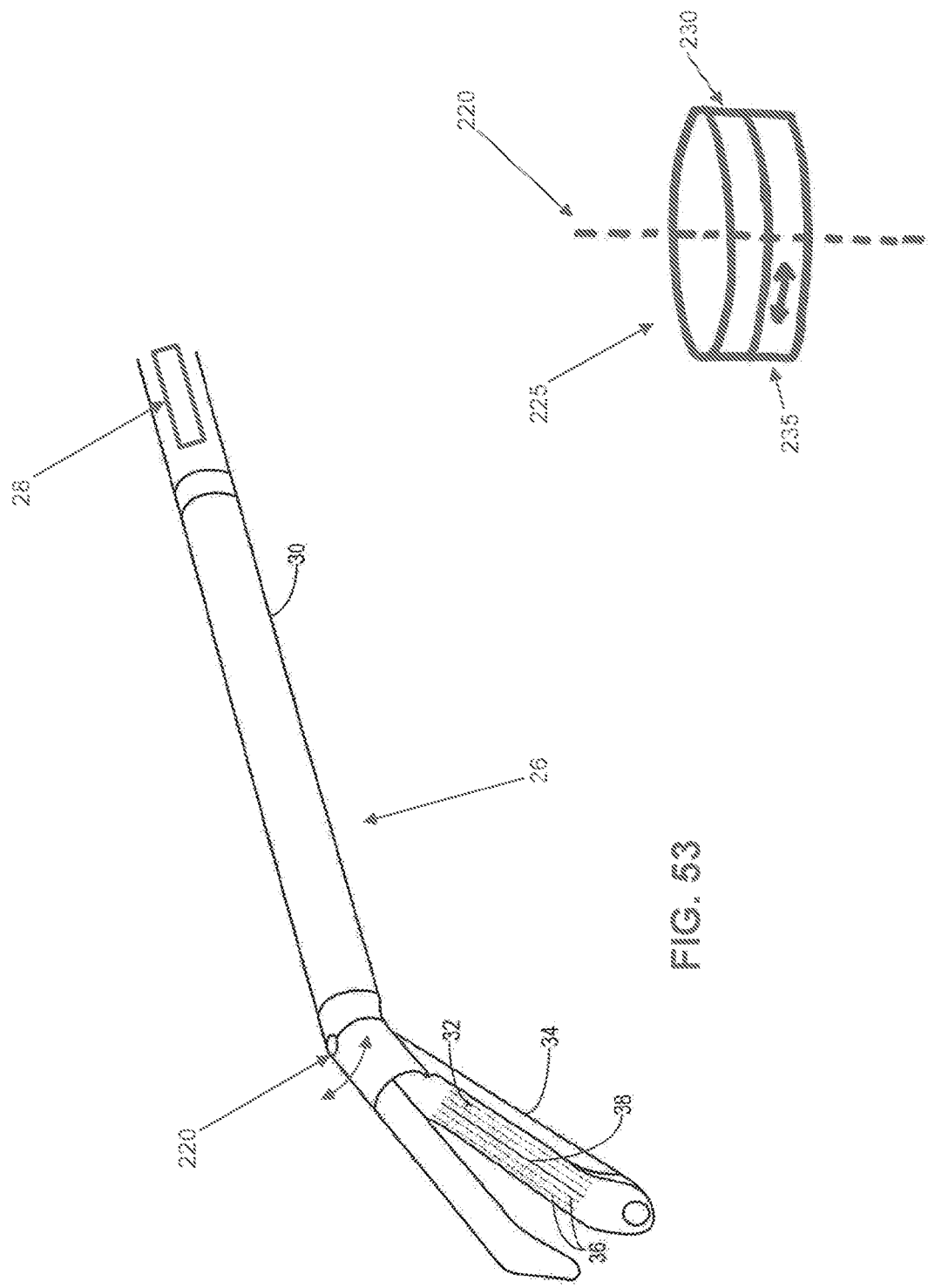

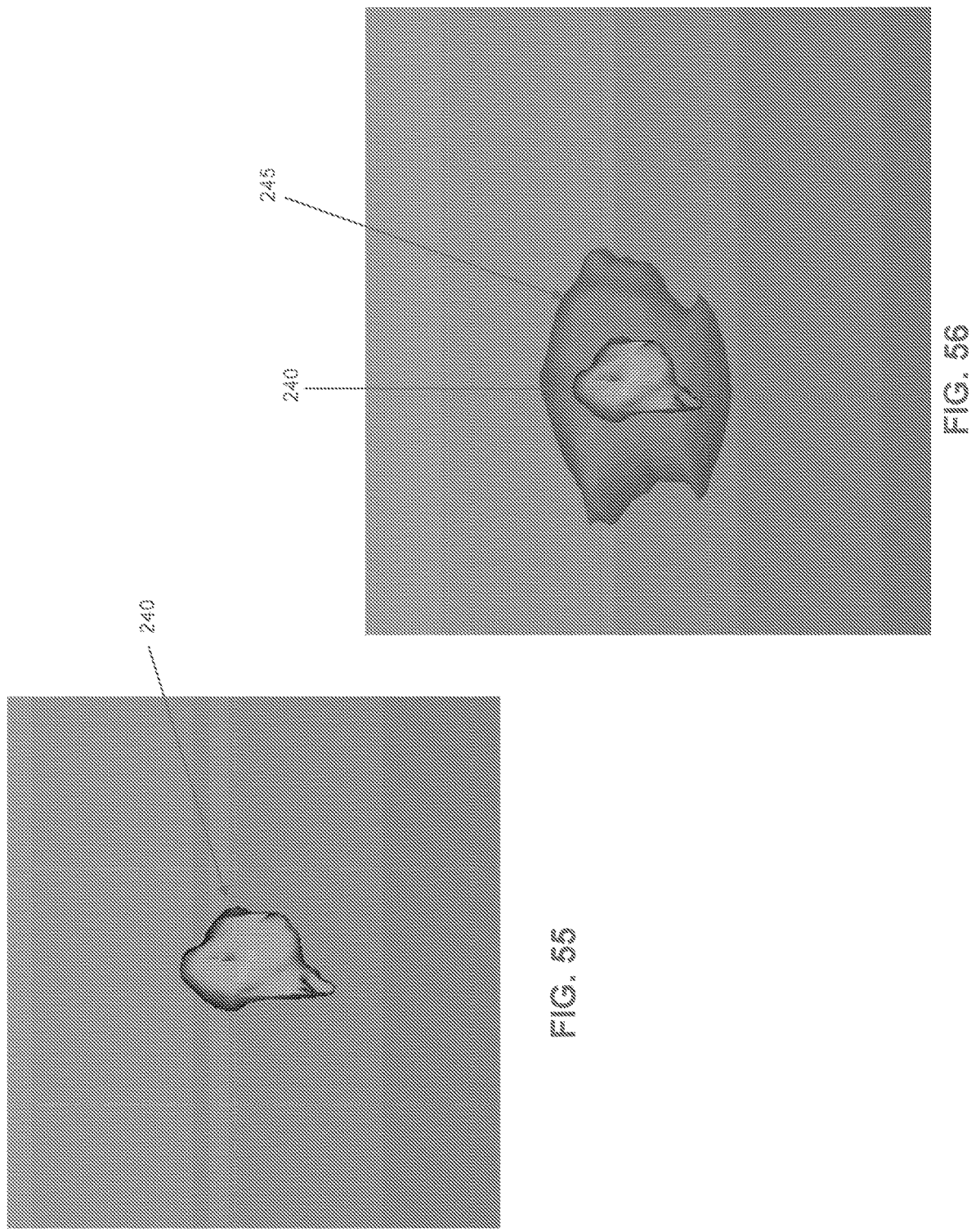

SYSTEM AND METHOD FOR A TISSUE RESECTION MARGIN MEASUREMENT DEVICE

REFERENCE TO PENDING PRIOR PATENT APPLICATIONS

This patent application claims benefit of:
(1) prior U.S. Provisional Patent Application Ser. No. 62/923,137, filed Oct. 18, 2019 by Raphael Bueno et al. for SYSTEM AND METHOD FOR A TISSUE RESECTION MARGIN MEASUREMENT DEVICE; and
(2) prior U.S. Provisional Patent Application Ser. No. 63/054,921, filed Jul. 22, 2020 by Raphael Bueno et al. for SYSTEM AND METHOD FOR A TISSUE RESECTION MARGIN MEASUREMENT DEVICE.

The two (2) above-identified patent applications are hereby incorporated herein by reference.

FIELD OF THE INVENTION

This invention relates to surgery in general, and more particularly to computer-assisted surgery.

BACKGROUND OF THE INVENTION

Minimally invasive surgical resection of lesions involves the precise excision of the lesion while sparing surrounding healthy and critical tissue. Some examples include, but are not limited to, breast conserving surgery and Video-Assisted Thoracic Surgery (VATS). Surgical resection of the lesion requires the removal of a margin of tissue around the lesion to ensure complete removal of the lesion cells and improved long-term survival. The default margin is dependent on the type of lesion and micro-invasion of the lesion into the surrounding tissue. While this is particularly true in cancer, where the size of the original lesion and the margin of normal tissue resected with the lesion is associated with survival, this is also true for non-cancerous lesions. Significant deformation of the tissue due to high viscoelasticity, physiological motion (such as collapsing of the lung, breathing or beating motion), or tissue manipulation can lead to difficulty in localizing the lesion and precise removal of the lesion. As a result, this can lead to insufficient resection, lesion recurrence locally, or by metastasis (in cancer), and poorer long-term benefits compared with cases where a sufficient margin is obtained. Two surgical applications are listed below as an example. However, the disclosed system and method may be applied for resection or biopsy of other lesions through a minimally invasive or image-guided approach or open-surgery, or a combination of approaches.

Lung Lesion Surgery

Current clinical practice to remove lung tissue segments involves opening the chest by cutting the sternum or by spreading the ribs. Many times ribs are broken and often segments are surgically removed during these procedures. The orthopedic trauma alone presents considerable pain and it can complicate the recovery process with patients. Thoracic pain of this magnitude also complicates the task of recovering a patient from general anesthesia since the body acclimates to forced ventilation and the pain can interrupt natural chest rhythm. Patients benefit dramatically from procedures that are performed through small incisions or ports in the chest without causing this orthopedic trauma.

Even though minimally invasive or VATS techniques are well known to provide benefit to the patient by minimizing trauma and speeding recovery times compared to open chest procedures, a substantial number of open chest procedures are currently still performed. This is due, at least in part, to the fact that there are only a limited number of instruments designed specifically to facilitate thoracic procedures in this way.

Surgery for lung cancer, however, is moving to a minimally invasive approach using VATS and smaller anatomic or non-anatomic lung resection (e.g., a wedge resection or segmentectomy) particularly for small lesions. In the conventional method of performing VATS, however, the lung is collapsed during surgery, leading to difficulty in precisely locating the lesion and determining the resection margins. Additionally, palpation of lung tissue is not always possible (particularly in the case of smaller or early stage cancers) due to the minimally invasive approach to surgery. Imprecise surgical resection could lead to incomplete resection and subsequent lesion recurrence.

Breast Lesion Surgery

Breast conserving surgery (BCS) involves the removal of the lesion while sparing the healthy breast parenchyma around the lesion. Studies have shown that BCS combined with chemotherapy has similar long-term benefits as mastectomy with the additional cosmetic advantage. However, identifying and resecting the entire lesion is a challenging task due to the highly deformable nature of the breast. Achieving the negative surgical margin with minimal damage to the healthy parenchyma is non-trivial due to the soft-tissue nature of the breast. In fact, studies show that up to 25% of breast resections leave positive margins and require re-treatment.

Therefore, a tissue resection margin measuring device is needed that overcomes the above limitations by providing an improved approach for precisely locating a lesion and determining the resection margins.

SUMMARY OF THE INVENTION

The present invention relates to a system and method for resecting a tissue mass while compensating for tissue deformation due to its elastic nature and physiologically induced motion. In a non-limiting example, the invention enables minimally invasive surgical procedures by providing a device and method to perform tissue resection that discriminates against traumatizing critical tissue and precisely determines the resection margin. Additionally, auditory, visual and haptic cues may be provided to the surgeon to identify and more precisely measure the lesion margins and critical structures surrounding the lesions to ensure complete and safe resection of the lesion.

Some embodiments of the invention provide a system for resecting a tissue mass. The system includes a surgical instrument and a first sensor for measuring a first signal. The first sensor is dimensioned to fit inside of or next to (e.g., in close proximity to) the target lesion/tissue mass, usually at a location between the tissue mass and the ultimate cut area-margin. The system also includes a second sensor for measuring a second signal, and the second sensor is coupled to the surgical instrument. A controller is in communication with the first sensor and the second sensor, and the controller executes a stored program to calculate a distance between the first sensor and the second sensor based on the first signal and the second signal.

In some embodiments the system may further include a sleeve dimensioned to engage at least one of a housing of the surgical device and the second sensor. The second sensor may be coupled to the housing of the surgical instrument by an adhesive, for example. The surgical device may be, for example, a stapler, a Bovi pencil or a cutting device configured to cut along a resection margin surrounding the target tissue mass, which may be a lesion (e.g., a tumor, a nodule, etc.). The resection margin may be included within the distance calculated between the first sensor and the second sensor. Other factors may be included in calculating the margins, such as the distance between the mass and the first sensor, and the configuration of the mass.

In one embodiment, the first signal received by the first sensor can indicate a position and an orientation of the tissue mass relative to the surgical instrument in real time. Similarly, the second signal received by the second sensor can indicate a position and an orientation of the surgical instrument relative to the tissue mass. In one embodiment, the second sensor indicates a position and an orientation of the surgical instrument in the same frame of reference as the first sensor. The first sensor may be a fiducial marker (sometimes referred to as a fiducial sensor or a fiducial tracker) embedded within an anchor made from superelastic material, and the second sensor may be an instrument sensor (sometimes referred to as an instrument tracker). In one embodiment, the first sensor may be configured to measure a position and an orientation of the tissue mass, and the second sensor may be configured to measure a position and an orientation of the surgical instrument.

In one embodiment, the system may further include a third sensor for measuring a third signal. The third sensor may be dimensioned to fit next to the tissue mass at a position opposite the first sensor, such that the third signal received by the third sensor indicates a position and an orientation of the tissue mass relative to the first sensor.

In one embodiment, the first sensor may be embedded within a hook structure made of a superelastic material, e.g., Nitinol. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within the tissue mass. In one embodiment, the first sensor that is embedded within the hook structure may be inserted into the tissue mass under real-time image guidance.

In one embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within the tissue mass. The hook structure may further comprise a plurality of extensions extending from a tube portion of the hook structure, such that the plurality of extensions may be dimensioned to receive the first sensor.

The system may further include a display in communication with the controller. The display may be coupled to the surgical instrument and configured to display the distance between the first sensor and the second sensor as calculated by a stored program executed by the controller, which may also be configured to include additional calculations. Distances from the base, mid and tip of the surgical instrument (e.g., a cutting instrument such as a stapler) can also be displayed. The display may be, but is not limited to, an OLED display or an LCD display. In one embodiment, the system may include an audible source for emitting an audible signal. The audible source may be in communication with the controller, which is configured to execute a stored program to alter the audible signal based on the distance between the first sensor and the second sensor. In one embodiment, the stored program is a navigation system.

The system may further include a piezoelectric actuator coupled to a handle of the surgical instrument. The piezoelectric actuator may be configured to emit a haptic signal. The piezoelectric actuator may be in communication with the controller, which is configured to execute a stored program to alter the haptic signal based on the distance between the first sensor and the second sensor.

The system may further include a monitor for emitting a visual signal in some embodiments. The monitor may be in communication with the controller, which is configured to execute a stored program to alter the visual signal based on the distance between the first sensor and the second sensor. Additionally or alternatively, the system may include a monitor for displaying a video overlay. The monitor may be in communication with the controller, which is configured to execute a stored program to fuse a laparoscopy, thoracoscopy or endoscopy image (i.e., a "scope image") with a virtual model image (i.e., an image computer-generated from a virtual model of the anatomy), so as to create the video overlay of the scope image with the virtual model image. The video overlay may be configured to identify a position of the tissue mass and the first sensor.

In one embodiment, the invention provides a method for resection of a tissue mass inside a patient. The method includes inserting a first sensor inside of or next to the target tissue mass (e.g., in close proximity to the tissue mass) and capturing at least one image of the first sensor embedded within or next to (e.g., in close proximity to) the tissue mass. A resection margin is calculated around the tissue mass using the at least one image. A surgical instrument is inserted into the patient, and the surgical instrument is coupled to a second sensor. The second sensor is tracked relative to the resection margin, and the surgical instrument is used to cut on the resection margin. The surgeon will determine, based on the diagnosis and size of the mass, what might be the best margin to accomplish. This information may also be used to determine the exact operation required.

In some embodiments the method may further include dimensioning a sleeve to engage at least one of a housing of the surgical device and the second sensor. Or the second sensor may be coupled to the housing of the surgical instrument by an adhesive, for example. In another embodiment, the sensor may be embedded within the device/instrument, or the sensor may be built into the device/instrument. The surgical device may be, for example, a stapler, a Bovi pencil or a cutting device configured to cut along a resection margin surrounding the tissue mass, which may be a lesion (e.g., a tumor, a nodule, etc.). The resection margin may be included within the distance calculated between the first sensor and the second sensor.

In some embodiments, the first signal received by the first sensor can indicate a position and an orientation of the first sensor (and hence the tissue mass) relative to the surgical instrument in real time. Similarly, the second signal received by the second sensor can indicate a position and an orientation of the surgical instrument relative to the tissue mass. In one embodiment, the second sensor indicates a position and an orientation of the surgical instrument in the same frame of reference as the first sensor. The first sensor may be a fiducial marker constructed from a superelastic material, and the second sensor may be an instrument sensor. In one embodiment, the first sensor may be configured to measure a position and an orientation of the tissue mass, and the second sensor may be configured to measure a position and an orientation of the surgical instrument.

In one embodiment, the method may further include providing a third sensor for measuring a third signal. The third sensor may be dimensioned to fit next to the tissue mass at a position opposite the first sensor, such that the third signal received by the third sensor indicates a position and an orientation of the tissue mass relative to the first sensor.

In some embodiments, the first sensor may be embedded within a hook structure. The hook structure may be in the form of a T-bar or J-bar and dimensioned to fit inside a delivery needle and/or a sheath. The delivery needle and/or the sheath may be configured to guide the first sensor, and the hook structure may be configured to anchor the first sensor within the tissue mass. In one embodiment, the first sensor that is embedded within the hook structure may be inserted into the tissue mass under real-time image guidance or under direct visual guidance.

In one embodiment, the first sensor is embedded within a hook structure that includes a plurality of prongs, and the first sensor may be dimensioned to fit inside a delivery needle and/or a sheath. The delivery needle and/or the sheath may be configured to guide the first sensor, and the plurality of prongs may be configured to anchor the first sensor within the tissue mass. The hook structure may further comprise a plurality of extensions extending from a tube portion of the hook structure, such that the plurality of extensions may be dimensioned to receive the first sensor.

The method may further include providing a display in communication with a controller. The display may be coupled to the surgical instrument and configured to display the distance calculated by the stored program executed by the controller. The display may be, but is not limited to, an OLED display or an LCD display. The display may also include information as to the distances between various sensors, as well as to the quality of the measurements. In some embodiments, the method may include emitting an audible signal from an audible source. The audible source may be in communication with the controller, which is configured to execute a stored program to alter the audible signal based on the distance between the first sensor and the second sensor. In one embodiment, the stored program is a navigation method.

The method may further include emitting a haptic signal from a piezoelectric actuator coupled to a handle of the surgical instrument. The piezoelectric actuator may be in communication with the controller, which is configured to execute a stored program to alter the haptic signal based on the distance between the first sensor and the second sensor.

In some embodiments, the method may further include emitting a visual signal on a monitor. The monitor may be in communication with the controller, which is configured to execute a stored program to alter the visual signal based on the distance between the first sensor and the second sensor. Additionally or alternatively, the method may include displaying a video overlay on the monitor. The monitor may be in communication with the controller, which is configured to execute a stored program to fuse a laparoscopy/thoracoscopy/endoscopy scope image(s) to a virtual model image so as to create the video overlay. The video overlay may be configured to identify a position of the tissue mass and the first sensor.

In one form of the invention, the system may be used to identify the location of a particular airway. In this form of the invention, the system comprises means for bronchoscopic positioning of a sensor into an airway of the lung. This bronchoscopic positioning of the sensor in an airway of the lung (e.g., by positioning the sensor on a bronchoscope or on a catheter within the brochoscope and advancing the bronchoscope into the airway of interest) can be used to define the lobar, segmental or subsegmental bronchus for surgery such as segmentectomy, lobectomy or wedge resection during the actual operation. This function can be independent of the lesion margin measurement, and the position of the sensor identifying the bronchus can be correlated with the position of another device (e.g., a surgical instrument) carrying another sensor so that the surgeon can define the correct bronchus for surgery from the chest side of the operation. Thus, in this form of the invention, one sensor is positioned on a bronchoscope or on a catheter placed within the bronchoscope which is inserted into a specific airway so as to define the location of that specific airway, and another sensor is positioned on a surgical instrument which is advanced for surgery from the chest side of the operation, with the system continuously tracking the position of the sensor on the surgical instrument vis-à-vis the position of the sensor on the bronchoscope, so that the surgeon can continuously track the location of the surgical instrument relative to the airway of interest (identified by the sensor on the bronchoscope), e.g., to target the airway identified by the sensor on the bronchoscope, to avoid the airway identified by the sensor on the bronchoscope, etc.

In one form of the invention, the system comprises means for mapping and tracking airways surrounding a lesion.

In one form of the invention, the system comprises means for bronchoscopic deployment of the fiducial sensor or another sensor into tissue (e.g., bronchoscopic deployment of the fiducial sensor into the mass or adjacent to the mass).

In one form of the invention, the system comprises means for measuring the articulation of a surgical stapler.

In one form of the invention, the system comprises means for marking the boundary of a resection margin of a lesion and positioning a surgical stapler adjacent to the boundary of a resection margin of a lesion.

In one form of the invention, there is provided a method for determining the position of an instrument relative to a selected lumen in an anatomical structure, the method comprising:

positioning a tracked catheter in the selected lumen of the anatomical structure, wherein the tracked catheter is tracked relative to a given frame of reference; and determining the position of a tracked instrument relative to the tracked catheter, wherein the tracked instrument is tracked relative to the given frame of reference, whereby to determine the position of the tracked instrument relative to the selected lumen of the anatomical structure.

In another form of the invention, there is provided a system for determining the position of an instrument relative to a selected lumen in an anatomical structure, the system comprising:

a catheter sized to be disposable in the selected lumen of the anatomical structure;

a catheter tracker for providing a catheter signal representative of the position of the catheter tracker relative to a given frame of reference, the catheter tracker being carried by the catheter;

an instrument;

an instrument tracker for providing an instrument signal representative of the position of the instrument tracker relative to the given frame of reference, the instrument tracker being carried by the instrument; and a controller for determining the position of the tracked instrument relative to the tracked catheter, whereby, when the tracked catheter is disposed in the selected lumen of the anatomical structure, the controller determines the position of the tracked instrument relative to the selected lumen in the anatomical structure.

In another form of the invention, there is provided a method for mapping and tracking a plurality of lumens in an anatomical structure, wherein the anatomical structure is deformable, the method comprising:

providing a virtual model of the anatomical structure while the anatomical structure is in a first configuration;

while the anatomical structure is in the first configuration, positioning a tracked catheter in one of the lumens in the anatomical structure which is to be mapped and tracked, and determining the position of the tracked catheter in that lumen so as to map the position of that lumen;

repeating the foregoing step for each of the lumens in the anatomical structure which is to be mapped and tracked so that those lumens are mapped;

supplementing the virtual model with the mapped lumens, whereby to provide a supplemented virtual model of the anatomical structure and the mapped lumens while the anatomical structure is in its first configuration;

maintaining the tracked catheter in one of the mapped lumens of the anatomical structure as the anatomical structure is deformed from its first configuration to a second configuration;

determining the position of the tracked catheter in the anatomical structure while the anatomical structure is in the second configuration; and modifying the supplemented virtual model so as to represent the anatomical structure and the mapped lumens while the anatomical structure is in its second configuration, whereby to provide a modified supplemented virtual model, wherein modification is effected by:

determining the spatial transformation of the tracked catheter as the anatomical structure deforms from its first configuration to its second configuration; and applying the spatial transformation of the tracked catheter to the mapped lumens of the supplemented virtual model so as to provide the modified supplemented virtual model of the anatomical structure and the mapped lumens while the anatomical structure is in its second configuration.

In another form of the invention, there is provided a method for mapping and tracking a selected lumen in an anatomical structure, wherein the anatomical structure is deformable, the method comprising:

positioning a tracked catheter in the selected lumen of the anatomical structure while the anatomical structure is in a first configuration;

determining the position of the tracked catheter while the anatomical structure is in the first configuration;

scanning the anatomical structure and the tracked catheter positioned in the selected lumen of the anatomical structure while the anatomical structure is in the first configuration;

creating a virtual model of the scanned anatomical structure and the tracked catheter positioned in the selected lumen of the anatomical structure while the anatomical structure is in its first configuration;

maintaining the tracked catheter in position within the selected lumen of the anatomical structure while the anatomical structure deforms to a second configuration;

determining the position and orientation of the tracked catheter while the anatomical structures is in its second configuration, whereby to determine the position of the selected lumen of the anatomical structure while the anatomical structure is in the second configuration; and adjusting the virtual model so as to represent the anatomical structure and the selected lumen while the anatomical structure is in its second configuration, whereby to provide an adjusted virtual model, wherein modification is effected by:

determining the spatial transformation of the tracked catheter as the anatomical structure deforms from its first configuration to its second configuration; and applying the spatial transformation of the tracked catheter to the selected lumen of the virtual model so as to provide the adjusted virtual model of the anatomical structure and the selected lumen while the anatomical structure is in its second configuration.

In another form of the invention, there is provided a system for mapping and tracking a plurality of lumens in an anatomical structure, wherein the anatomical structure is deformable, the system comprising:

a catheter sized to be disposed in the plurality of lumens of the anatomical structure which are to be mapped and tracked, and configured to remain in a selected lumen of the anatomical structure during deformation of the anatomical structure;

a catheter tracker for providing a catheter signal representative of the position of the catheter tracker, the catheter tracker being carried by the catheter;

a virtual model of the anatomical structure representing the anatomical structure while it is in a first configuration; and a controller for:
(i) determining the position of the tracked catheter as the tracked catheter is disposed within each of the plurality of lumens so as to map the plurality of lumens while the anatomical structure is in its first configuration; and
(ii) supplementing the virtual model with the mapped lumens, whereby to provide a supplemented virtual model of the anatomical structure and the mapped lumens representing the anatomical structure while it is in its first configuration.

In another form of the invention, there is provided a system for mapping and tracking a selected lumen in an anatomical structure, wherein the anatomical structure is deformable, the system comprising:

a catheter sized to be disposed in the selected lumen of the anatomical structure and configured to remain in the selected lumen of the anatomical structure during deformation of the anatomical structure;

a catheter tracker for providing a catheter signal representative of the position of the catheter tracker, the catheter tracker being carried by the catheter;

a virtual model of the anatomical structure and the tracked catheter positioned in the selected lumen of the anatomical structure, wherein the virtual model is created while the anatomical structure is in a first configuration; and a controller for:
(i) determining the position of the tracked catheter after the anatomical structure has assumed a second configuration; and
(ii) adjusting the virtual model of the anatomical structure and the tracked catheter so that the virtual model conforms to the position of the tracked catheter when the anatomical structure is in its second configuration.

In another form of the invention, there is provided a method for tracking a tissue mass disposed in or on an anatomical structure, wherein the anatomical structure comprises at least one lumen, the method comprising:

advancing a scope along the at least one lumen until the distal end of the scope is disposed in the vicinity of the selected tissue mass;

advancing a fiducial sensor through the scope, into the anatomical structure, and securing the fiducial sensor to the anatomical structure in the vicinity of the tissue mass; and detecting the position of the fiducial sensor within the anatomical structure.

In another form of the invention, there is provided a method for tracking a tissue mass disposed in or on an anatomical structure, wherein the anatomical structure comprises at least one lumen, the method comprising:

providing a sensor assembly comprising a fiducial sensor and an electrical lead extending distally from the fiducial sensor, and providing a deployment assembly comprising a needle cannula and a pusher, wherein the sensor assembly is slidably disposed in the needle cannula distal to the pusher;

advancing a scope along the at least one lumen until the distal end of the scope is disposed in the vicinity of the selected tissue mass;

advancing the needle cannula through the scope, into the anatomical structure, and through an outer surface of the anatomical structure;

retracting the needle cannula so as to expose a portion of the electrical lead extending through the outer surface of the anatomical structure;

supplying electrical power to the fiducial sensor via the electrical lead extending through the outer surface of the anatomical structure;

securing the fiducial sensor to the anatomical structure in the vicinity of the tissue mass by advancing the pusher relative to the needle cannula or by retracting the needle cannula relative to the pusher; and detecting the position of the fiducial sensor within the anatomical structure.

In another form of the invention, there is provided a system for determining the position of an instrument relative to a tissue mass carried by an anatomical structure, the system comprising:

a wireless fiducial tracker for providing a fiducial signal representative of the position of the wireless fiducial tracker, the wireless fiducial tracker adapted to be secured in the anatomical structure in the vicinity of the tissue mass;

an instrument;

an instrument tracker for providing an instrument signal representative of the position of the instrument tracker, the instrument tracker being carried by the instrument; and a controller for determining the position of the tracked instrument relative to the wireless fiducial tracker.

In another form of the invention, there is provided a system for determining the position of an instrument relative to a tissue mass carried by an anatomical structure, the system comprising:

a fiducial tracker for providing a fiducial signal representative of the position and orientation of the fiducial tracker, the fiducial tracker adapted to be secured in the anatomical structure in the vicinity of the tissue mass;

an electrical lead for providing electrical power to the fiducial tracker, the electrical lead being releasably connected to the fiducial tracker;

an instrument;

an instrument tracker for providing an instrument signal representative of the position of the instrument tracker, the instrument tracker being carried by the instrument; and a controller for determining the position of the tracked instrument relative to the fiducial tracker.

In another form of the invention, there is provided a system for determining the position and orientation of an instrument relative to a tissue mass disposed in or on an anatomical structure, the system comprising:

a sensor assembly comprising:

a fiducial tracker for providing a fiducial signal representative of the position of the fiducial tracker, the fiducial tracker adapted to be secured in the anatomical structure in the vicinity of the tissue mass; and an electrical lead for providing electrical power to the fiducial tracker, the electrical lead extending distally from the fiducial tracker;

an instrument;

an instrument tracker for providing an instrument signal representative of the position and orientation of the instrument tracker, the instrument tracker being carried by the instrument; and a controller for determining the position and orientation of the tracked instrument relative to the fiducial tracker.

In another form of the invention, there is provided a system for determining the position and orientation of an instrument relative to a tissue mass disposed in or on an anatomical structure, the system comprising:

a sensor assembly comprising:

a fiducial tracker for providing a fiducial signal representative of the position of the fiducial tracker, the fiducial tracker adapted to be secured in the anatomical structure in the vicinity of the tissue mass; and an electrical lead for providing electrical power to the fiducial tracker, the electrical lead extending distally from the fiducial tracker;

a deployment assembly comprising a needle cannula and a pusher, wherein the sensor assembly is slidably disposed within the needle cannula distal to the pusher;

an instrument;

an instrument tracker for providing an instrument signal representative of the position and orientation of the instrument tracker, the instrument tracker being carried by the instrument; and a controller for determining the position and orientation of the tracked instrument relative to the fiducial tracker.

In another form of the invention, there is provided a method for determining the position of an end effector of an instrument relative to a tissue mass carried by an anatomical structure, wherein the instrument comprises a shaft and the end effector, and wherein the disposition of the end effector relative to the shaft is adjustable, the method comprising:

tracking the position of the tissue mass;

tracking the shaft of the instrument;

determining the disposition of the end effector relative to the shaft; and determining the disposition of the end effector relative to the tissue mass.

In another form of the invention, there is provided a system for determining the position of an end effector of instrument relative to a tissue mass carried by an anatomical structure, the system comprising:

a wireless fiducial tracker for providing a fiducial signal representative of the position of the wireless fiducial tracker, the wireless fiducial tracker adapted to be secured in the anatomical structure in the vicinity of the tissue mass;

an instrument comprising a shaft and an end effector, wherein the disposition of the end effector relative to the shaft is adjustable;

an instrument tracker for providing an instrument signal representative of the position of the instrument tracker, the instrument tracker being carried by the shaft of the instrument;

a sensor for detecting the disposition of the end effector relative to the shaft; and a controller for determining the position of the tracked instrument relative to the wireless fiducial tracker.

In another form of the invention, there is provided a method for directing the position of an instrument relative to a tissue mass carried by an anatomical structure, the method comprising:

determining the tangent lines of the tissue mass;
tracking the position of the tissue mass;
tracking the position of the instrument;
determining the disposition of the instrument relative to the tangent lines; and
directing movement of the instrument so that a portion of the instrument is aligned with the tangent lines.

In another form of the invention, there is provided a system for directing the position of an instrument relative to a tissue mass carried by an anatomical structure, the system comprising:

a fiducial tracker for providing a fiducial signal representative of the position of the fiducial tracker, the fiducial tracker adapted to be secured in the anatomical structure in the vicinity of the tissue mass;
an instrument;
an instrument tracker for providing an instrument signal representative of the position of the instrument tracker, the instrument tracker being carried by the instrument; and
a controller for determining the tangent lines of the tissue mass and for directing the position of the tracked instrument relative to the tangent lines.

These and other features, aspects, and advantages of the present invention will become better understood upon consideration of the following detailed description, drawings, and appended claims.

BRIEF DESCRIPTION OF THE DRAWINGS

FIG. 12 is a schematic view showing the tree-like structure of the airways of the lung.

FIGS. 13, 13A and 13B are schematic views showing how a bronchoscope can be used to position a tracked catheter (i.e., a catheter carrying a sensor) in a specific airway of the lung, whereby to identify that specific airway of the lung, and how a surgical instrument carrying another sensor can be guided relative to that airway (e.g., to target that airway, to avoid that airway, etc.).

FIGS. 14-35 are schematic views showing how a tracked catheter can be used to identify the location of an airway.

FIGS. 53 and 54 are schematic views showing a surgical stapler with an articulation sensor for detecting the articulation of the head of the surgical stapler.

FIGS. 55 and 56 are schematic views showing (i) a model of a lesion, and (ii) a model of a resection margin in combination with a model of a lesion.

DETAILED DESCRIPTION OF THE INVENTION

Figure 1:
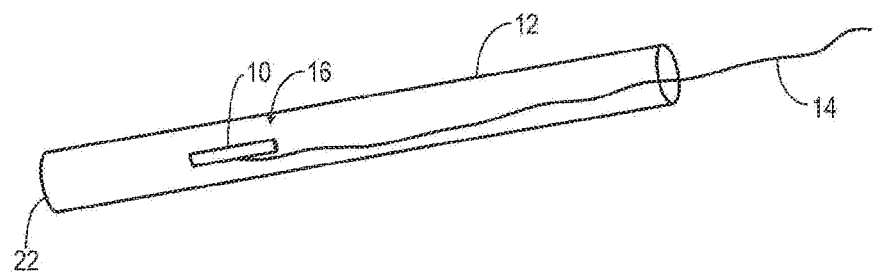
FIG. 1 is a perspective view of an exemplary fiducial sensor being deployed through a delivery needle according to one embodiment of the present invention.

Before any embodiments of the invention are explained in detail, it is to be understood that the invention is not limited in its application to the specific details of construction and the arrangement of components set forth in the following description or illustrated in the following drawings. The invention is capable of other embodiments and of being practiced or of being carried out in other ways. Also, it is to be understood that the phraseology and terminology used herein is for the purpose of description and should not be regarded as limiting. The use herein of "including," "comprising," or "having" and variations thereof is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from the scope of the present invention. Thus, embodiments of the invention are not intended to be limited to the specific embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present invention. Skilled artisans will recognize the examples provided herein have many useful alternatives and fall within the scope of embodiments of the invention.

Tracking The Location Of A Tissue Mass Using Fiducial Sensors

Figure 2:
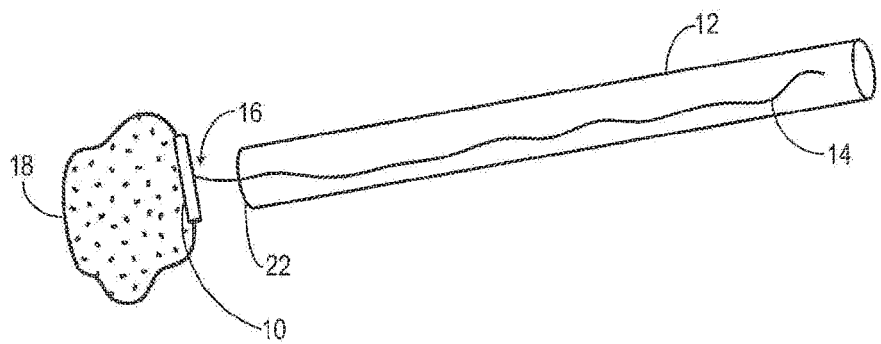
FIG. 2 is a perspective view of the exemplary fiducial sensor of FIG. 1 being deployed through the delivery needle next to a tissue mass according to one embodiment of the present invention (note that the fiducial sensor may be placed adjacent to the tissue mass so that the fiducial sensor is in contact with the tissue mass or so that the fiducial sensor is slightly spaced from the tissue mass).
Figure 3:
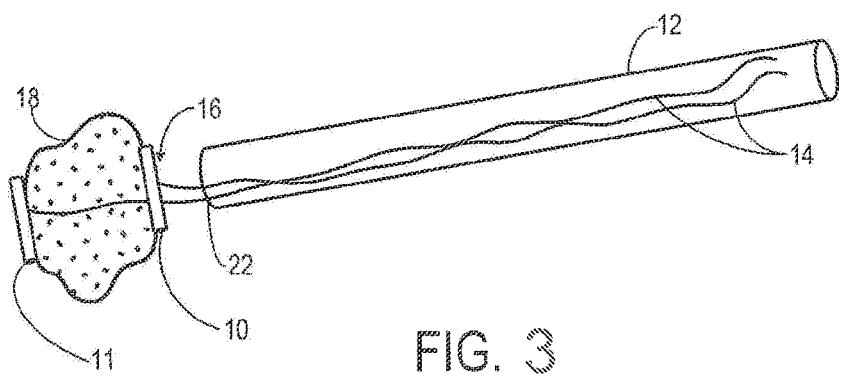
FIG. 3 is a perspective view of an additional fiducial sensor and the exemplary fiducial sensor of FIG. 1 being deployed through the delivery needle next to the tissue mass according to one embodiment of the present invention.

FIGS. 1-3 illustrate an exemplary fiducial sensor 10 (also sometimes referred to as a fiducial marker or a fiducial tracker) being inserted through a delivery needle 12. The fiducial sensor 10 may be, for example, a marker that includes a transmitter that measures position and orientation of a tissue mass 18 in real-time. The fiducial sensor 10 may be attached to a cable 14, as shown in FIGS. 1-3, or the fiducial sensor 10 may be wireless. The fiducial sensor 10 may be embedded within a hook structure 16, as shown in FIG. 1. The hook structure 16 of the fiducial sensor 10 can be made from a superelastic material, for example nitinol, or stainless steel, or any other suitable material. This will allow for the fiducial sensor 10 to be inserted through the delivery needle 12 and deployed through an opening 22 (i.e., the lumen) of the delivery needle 12 into the center of or at the periphery of the tissue mass 18. The tissue mass 18 may be, for example, a lesion (e.g., a tumor, a nodule, etc.).

Figure 4:
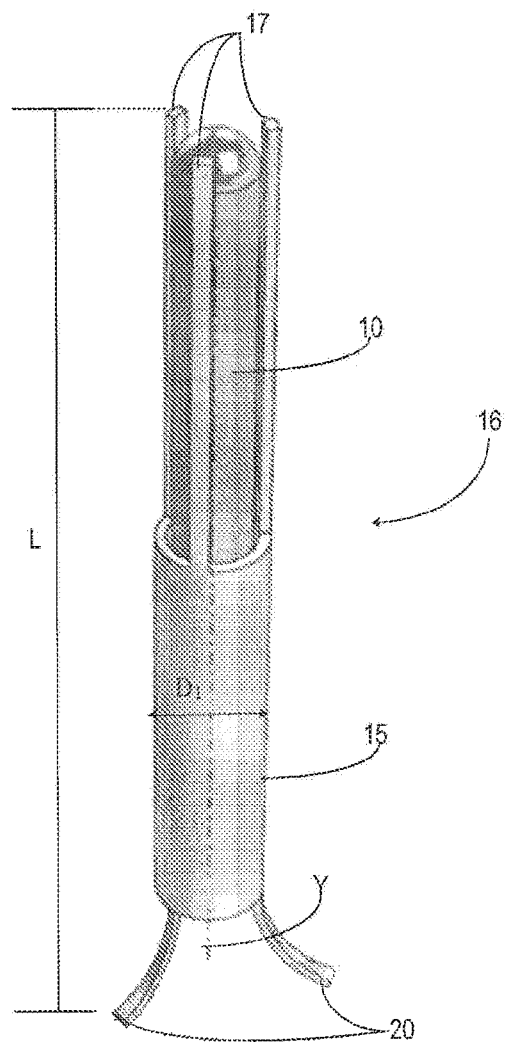
FIG. 4 is a perspective view of an exemplary fiducial sensor embedded within a hook structure according to another embodiment of the present invention.

As shown in FIG. 4, a more detailed view of the fiducial sensor 10 and hook structure 16 is shown. The hook structure 16 may include a tube portion 15 having a plurality of extensions 17 extending from one end of the tube portion 15 and a plurality of prongs 20 extending from an opposing end of the tube portion 15. The tube portion 15 may be, for example, a nitinol tube having an outer diameter $D_1$ between about 0.6 millimeters and about 0.8 millimeters, and the hook structure 16 may have an overall length L between about 8 millimeters and about 12 millimeters. The tube portion 15 may be laser micro-machined into a cylindrical shape having the plurality of extensions 17 extending therefrom to secure the fiducial sensor 10 in place. In some embodiments, the fiducial sensor 10 may be an electromagnetic sensor that is attached to the proximal end of the hook structure 16 using a medical grade epoxy adhesive, such as AA-Bond FDA22.

The plurality of prongs 20, as shown in FIG. 4, may be configured to anchor the hook structure 16, including the fiducial sensor 10, into a tissue mass or at the periphery of a tissue mass, such as the tissue mass 18 of FIG. 2. The plurality of prongs 20 may be constructed from a superelastic shape memory alloy, such as nitinol. The plurality of prongs 20 may be bent, for example, and extend outwardly from a central axis Y of the hook structure 16. The plurality of prongs 20 may also be heat-treated to ensure that the prongs 20 retain the curved shape and the phase structure of the nitinol is in the Martensite phase, for example. In the embodiment shown in FIG. 4, the hook structure 16 includes three prongs 20, however, any suitable number of prongs may be provided in order to anchor the hook structure 16 to the tissue mass or at the periphery of a tissue mass, such as the tissue mass 18.

The fiducial sensor 10 along with the hook structure 16 may be inserted through a distal end of the delivery needle 12, which may be an 18-gauge needle, for example. The plurality of prongs 20 of the hook structure 16 may be inserted into the lumen 22 of the delivery needle 12 first. Advantageously, due to the superelastic nature of nitinol, the hook structure 16 can be easily inserted into the lumen 22 of the delivery needle 12. The hook structure 16 may be deployed using a metal stylet (not shown) that is inserted through the lumen 22 of the delivery needle 12. Upon being completely deployed, the plurality of prongs 20 will regain their original curved shape and open up to firmly anchor the hook structure 16 into or at the periphery of the tissue mass 18. The delivery needle 12 may then be removed after deployment of the hook structure 16.

Figure 6:
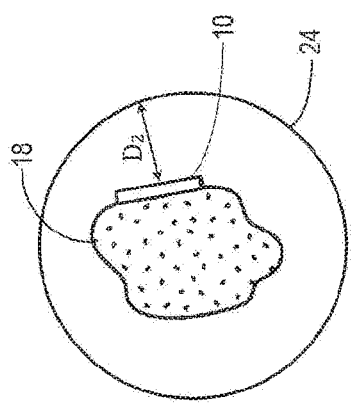
FIG. 6 is a perspective view of the fiducial sensor embedded next to the tissue mass of FIG. 2, with the resection margin surrounding the tissue mass (note that the fiducial sensor may be placed adjacent to the tissue mass so that the fiducial sensor is in contact with the tissue mass or so that the fiducial sensor is slightly spaced from the tissue mass).
Figure 5:
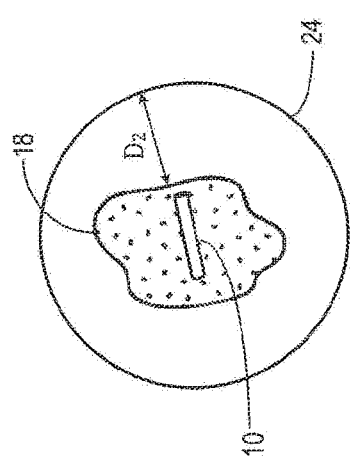
FIG. 5 is a perspective view of the fiducial sensor embedded in the tissue mass of FIG. 2, with a resection margin surrounding the tissue mass.

In some embodiments, the fiducial sensor 10 along with the hook structure 16 may be inserted through the delivery needle 12 under real-time image guidance (e.g., CT, C-arm CT, MRI, Ultrasound, etc.) and embedded within the tissue mass 18, as shown in FIG. 5, or next to the tissue mass 18 (e.g., in close proximity to), as shown in FIG. 6. The fiducial sensor 10 may be embedded within or next to the tissue mass 18 before or during a surgical procedure. By using real-time image guidance, the spatial relationship (i.e., position and orientation) of the fiducial sensor 10 to the tissue mass 18 in three dimensions is known at all times. The hook structure 16 may be in the form of a T-bar or J-bar, for example, to anchor the fiducial sensor 10 within or next to the tissue mass 18 to inhibit migration. Advantageously, the force is at the center of the T-bar 16 due to the wire 14, thereby facilitating anchoring the fiducial sensor 10 within or next to the tissue mass 18. The fiducial sensor 10 embedded within or next to the tissue mass 18 will measure the position and orientation of the tissue mass 18 in real-time in spite of any deformation introduced due to soft tissue deformation or physiological motion such as collapsing of the lung or respiration, for example, thereby easily identifying the location of the tissue mass 18 that is often difficult to determine.

In an alternative embodiment, shown in FIG. 3, a second fiducial sensor 11 (in the form of a T-bar assembly, for example) may be put in a different location near the tissue mass 18. The second fiducial sensor 11 may have a separate cable 14 from the first fiducial sensor 10, as shown in FIG. 3, or the first fiducial sensor 10 and the second fiducial sensor 11 may share the same cable 14. The second fiducial sensor 11, or any other such device, can be used to improve the localization of the tissue mass 18, even when there may be deformation. For example, the second fiducial sensor 11 can be placed on the opposite side of the tissue mass 18 from the first fiducial sensor 10 and be recognized by the first fiducial sensor 10 through distortions in the electromagnetic field. Therefore, by knowing that the tissue mass 18 is between these two sensors, the tissue mass 18 can be localized despite changes in the soft tissue.

Referring now to FIGS. 5 and 6, once the position and orientation of the tissue mass 18 is known, a resection margin 24 having a predetermined distance $D_2$ surrounding the tissue mass 18 is determined by creating a three dimensional envelope around the tissue mass 18. The resection margin 24 may be manually set to the desired predetermined distance $D_2$, for example, two centimeters, and is dependent on the surgeon's preference and the lesion type. The predetermined distance $D_2$ defines a threshold value so when a surgical device 26 (e.g., a surgical stapler), described in further detail below, is in a position less than the threshold value, auditory, visual and/or haptic cues may be provided to the surgeon or to the surgical device 26 to ensure precise and complete resection of the tissue mass 18.

Tracking The Location Of A Surgical Device Using An Instrument Sensor

Figure 7:
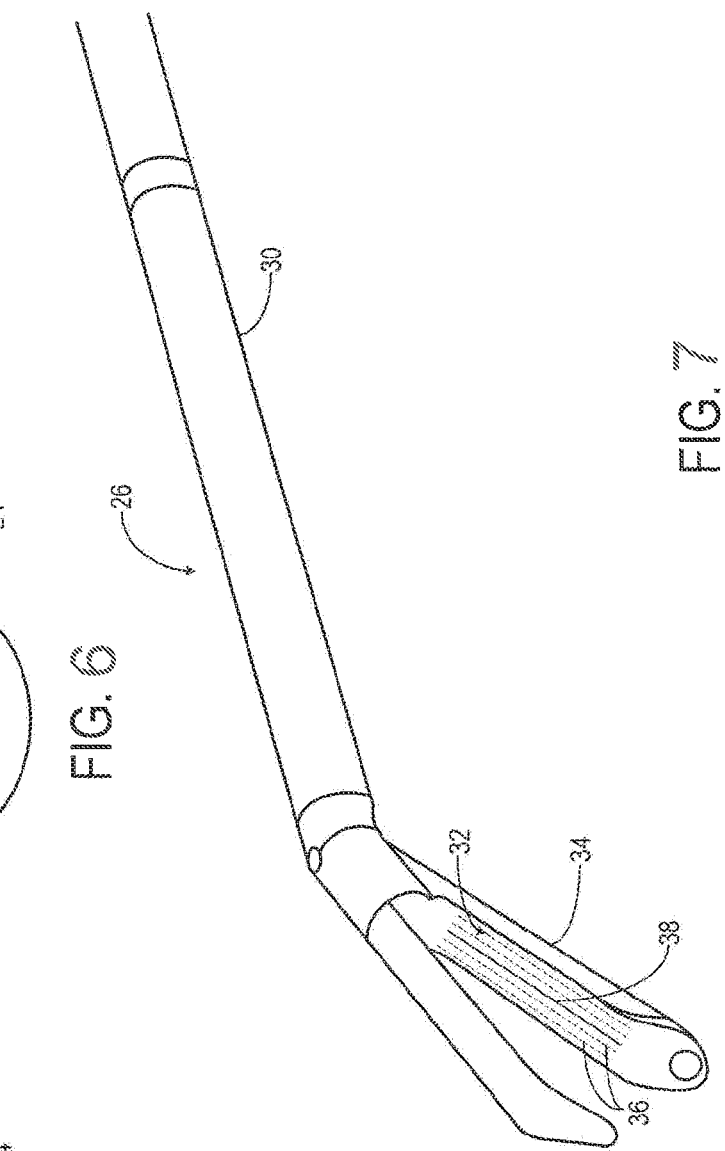
FIG. 7 is a partial perspective view of a conventional stapler device used for resecting a tissue mass.

Referring now to FIG. 7, a conventional surgical device 26, such as a surgical stapler, Bovi pencil, kitner, laparoscope and/or any suitable cutting, resecting or ablating device, is shown. The surgical device 26 may include a handle 30 coupled to a fastening assembly 32 at an opposite end of the surgical device 26. The fastening assembly 32 may be a single-use component that is removably connected to the handle 30, i.e., the fastening assembly 32 may be a cartridge that connects to the handle 30 and is removed after use. The fastening assembly 32 includes a housing 34 that contains a plurality of fasteners 36 that are secured to tissue during resection of the tissue mass 18. The fastening assembly 32 may also include a blade slot 38 that accommodates a blade (not shown) for cutting along the resection margin 24 of the tissue mass 18.

Figure 8:
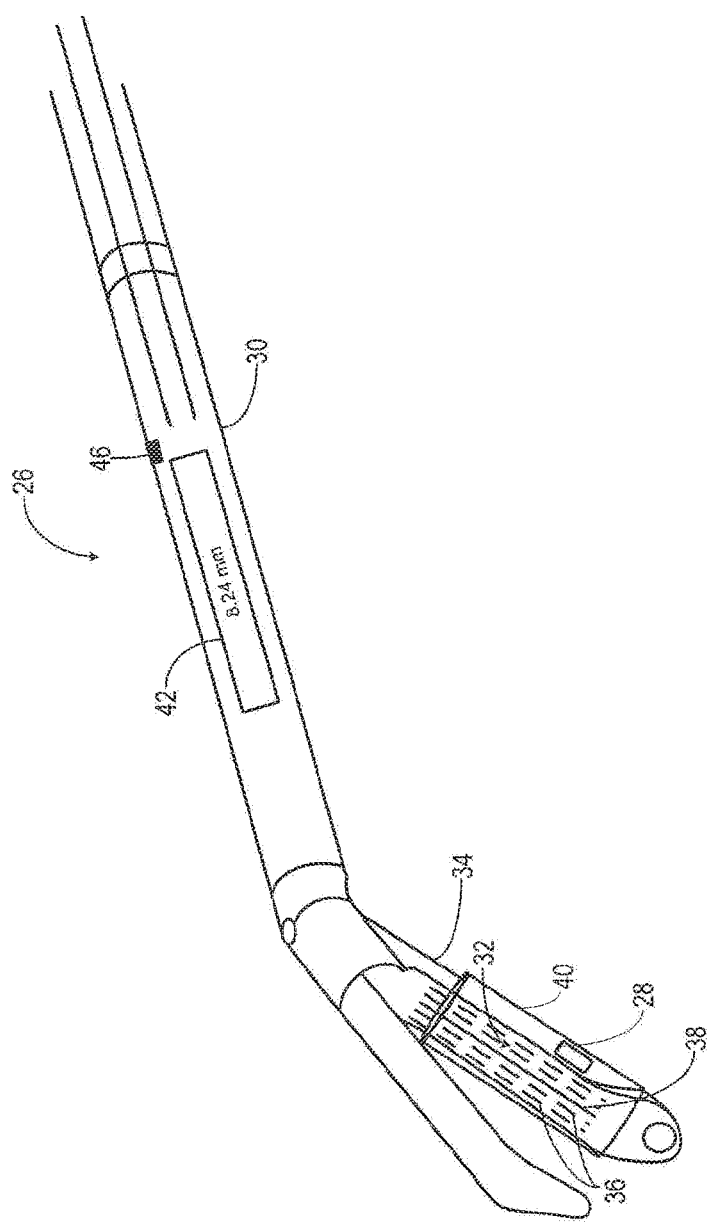
FIG. 8 is a partial perspective view of the stapler device of FIG. 7 with a sleeve including an instrument sensor over a housing of the stapler device according to one embodiment of the present invention.

In a preferred embodiment, the surgical device 26 includes a sleeve 40 that is dimensioned to slide over the housing 34, for example, as shown in FIG. 8. The sleeve 40 may be any commercially available sleeve, for example, that is configured to go over the housing 34 of the surgical device 26. An instrument sensor 28 (sometimes referred to as an instrument tracker) may be attached, by stitching for example, to the sleeve 40. Alternatively, the instrument sensor 28 may be attached directly to the housing 34 of the surgical device 26 via any suitable adhesive or integrated within the housing 34 itself. Regardless of where the instrument sensor 28 is attached, either the sleeve 40 or the housing 34, the instrument sensor 28 can measure the position and orientation of the surgical device 26 in the same imaging reference frame as the fiducial sensor 10 embedded within or next to the tissue mass 18. In other words, the position of the surgical device 26 may be precisely measured with respect to the fiducial sensor 10 which is within or next to the tissue mass 18, as will be described in further detail below. Since both the fiducial sensor 10 and the instrument sensor 28 are measured in the same reference frame, errors introduced due to the registration and calibration steps, requiring a change of reference axis, can be minimized.

The sleeve 40 may also include a display 42 that shows the user a distance $D_3$, shown in FIG. 9, of the surgical device 26 from the resection margin 24, as will be described below. The display 42 may be attached to the handle 30 of the surgical device 26 and could be any commercially available organic light-emitting diode (OLED) display or liquid-crystal (LCD) display. In the case of an OLED display, a reformatted CT image of the tissue mass 18 located at the tip of the surgical device 26, for example, may be displayed to the user.

Guiding The Surgical Device To The Tissue Mass

Figure 9:
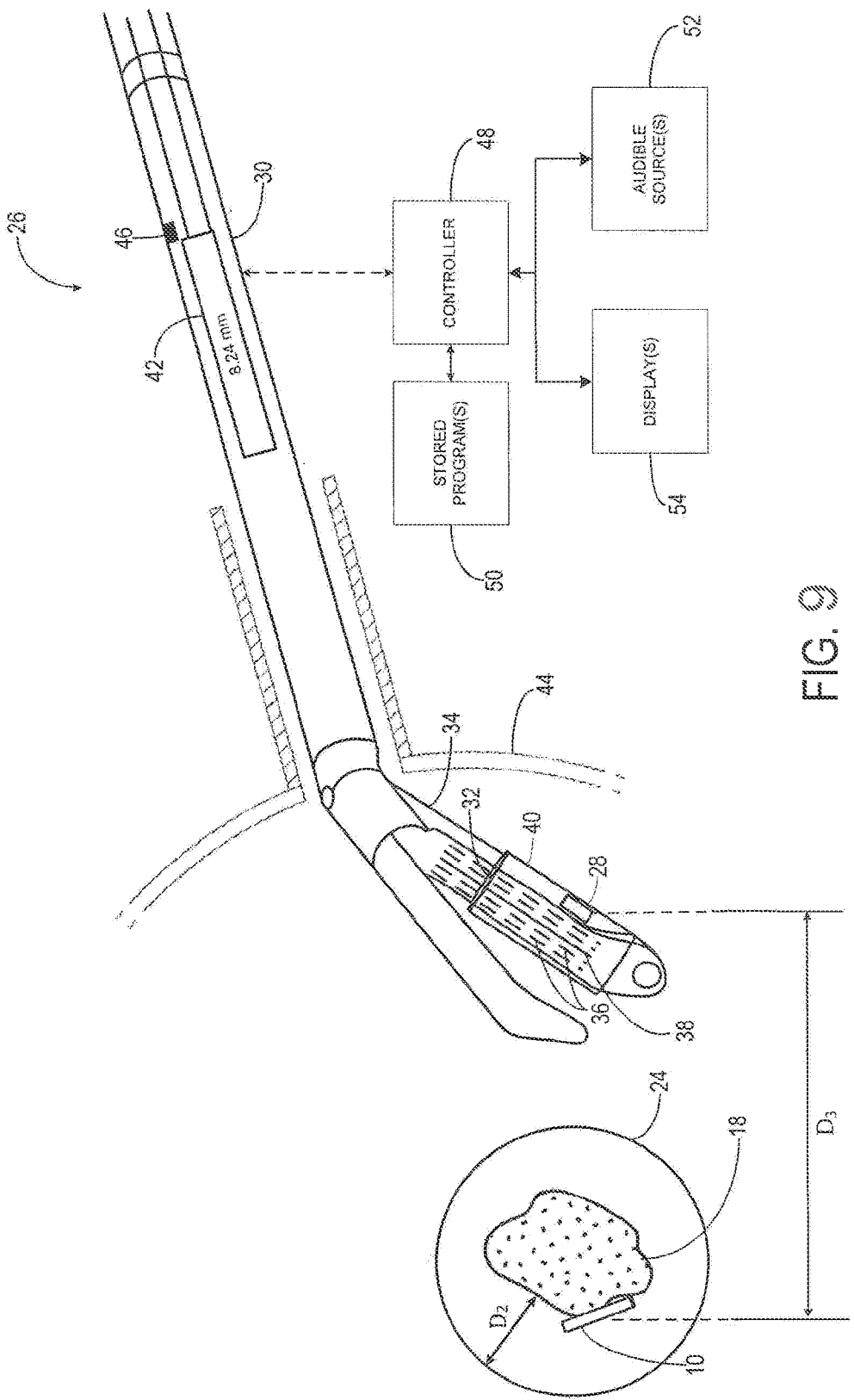
FIG. 9 is a perspective view of the stapler device of FIG. 8 inserted into a patient and shows a distance between the fiducial sensor and the instrument sensor.

Referring now to FIG. 9, during operation, the fiducial sensor 10 is positioned next to or embedded within the tissue mass 18 using the plurality of prongs 20 of the hook structure 16, as previously described. A CT/MRI/fluoroscopic/C-arm CT examination, for example, is performed to acquire images of the fiducial sensor 10 positioned next to or embedded within the tissue mass 18. The tissue mass 18 is then segmented from the pre-operative diagnostic CT/MRI examination and a three dimensional model (not shown) of the tissue mass 18 is generated. The intraoperative images obtained during placement of the fiducial sensor 10 may be registered to the patient's diagnostic exam, and the location of the fiducial sensor 10 may be estimated. As previously discussed, the resection margin 24 having the predetermined distance $D_2$ surrounding the tissue mass 18 is displayed to the user on a monitor (not shown) as a three dimensional envelope or proximity sphere around the tissue mass 18. The predetermined distance $D_2$ of the resection margin 24 may be determined based on the surgeon's preferences and the type of tissue mass 18.

The surgical device 26 is then inserted into a body 44 (i.e., the patient), as shown in FIG. 9, to cut the tissue mass 18 along the resection margin 24. The fiducial sensor 10 embedded within or close to the tissue mass 18 is in electrical or wireless communication with a controller 48. The controller 48 may be a programmable logic controller (PLC) and is configured to interpret a signal generated by the fiducial sensor 10. The fiducial sensor 10 may be an electromagnetic sensor, for example, that generates a signal indicative of the position and orientation (e.g., one or more spatial coordinates) of the fiducial sensor 10. The signal generated by the fiducial sensor 10 may be, for example, an electrical signal and the controller 48 may interpret this signal via a stored program 50. The stored program 50 may include, for example, a navigation system that is in communication with the fiducial sensor 10 and the instrument sensor 28.

Similarly, the instrument sensor 28 may be an electromagnetic sensor, for example, that generates a signal indicative of the position and orientation (e.g., one or more spatial coordinates) of the instrument sensor 28. The signal generated by the instrument sensor 28 may be, for example, an electrical signal and the controller 48 may interpret this signal via a stored program 50. The fiducial sensor 10 and the instrument sensor 28 communicate with the controller 48 and relay the position and orientation of the tissue mass 18 and the surgical device 26 using the navigation system. In some embodiments, the stored program 50 may be configured to run calibration and/or registration algorithms to track the distal tip of the surgical device 26 and the normal vector to the surgical device 26. Thereafter, the stored program 50 of the controller 48 calculates the distance $D_3$, shown in FIG. 9, between the fiducial sensor 10 and the instrument sensor 28 such that when the surgical device 26 is below a threshold value of $D_3$, an auditory, visual or haptic cue is generated for the user.

As the surgical device 26 is navigated towards the resection margin 24 of the tissue mass 18, the surgical device 26 may excise the tissue mass 18 while minimizing damage to surrounding tissue due to both the fiducial sensor 10 and instrument sensor 28 being actively tracked. Minimal damage to the surrounding healthy tissue may also ensure normal physiological function, for example, lung function. Utilizing feedback from the fiducial sensor 10 and the instrument sensor 28 on the surgical device 26, the distance $D_3$ from the tissue mass 18 and the surgical device 26 may be known to the user and visible on the display 42 at all times. As a result, the desired resection margin 24 may be maintained at all times, thereby ensuring complete resection of the tissue mass 18. In one embodiment, the position and orientation data of the tissue mass 18 and the surgical device 26 may be used to lock or unlock the surgical device 26 to inhibit erroneous resection of the tissue mass 18.

Tissue Deformation Algorithms

In some embodiments, the stored program 50 of the controller 48 may be configured to include one or more deformation algorithms that estimate or model changes that can occur to the resection margin 24 during a procedure, as a result of deformations of the tissue mass 18 and/or the surrounding tissue. The deformation algorithms attempt to account for any such changes to the resection margin 24 to provide more accurate resection margins to a user during a procedure, which aids in complete resection of the tissue mass 18 while limiting damage to, or removal of, healthy surrounding tissue.

In one non-limiting example, the stored program 50 includes a deformation algorithm that assumes that the tissue mass 18 (e.g., a breast lesion) is rigid and that the surrounding tissue (e.g., the parenchyma) deforms. The algorithm assumes every point on the tissue mass 18 moves along with the fiducial sensor 10, which is anchored to the tissue mass 18 as described above. In another non-limiting example, the stored program 50 includes a deformation algorithm that assumes the tissue mass 18 is a rigid object moving through a viscoelastic or fluid medium. In yet another non-limiting example, patient-specific properties of the tissue mass 18 and the surrounding tissue can be measured, for example, via a CT/MRI/fluoroscopic examination, to predict deformations to tissue mass 18 or resection margin 24 that occur during an operation for that specific patient. It should be appreciated that the deformation algorithms of the stored program 50 may operate on a real-time basis with the navigation system of the stored program 50.

More specifically, a tissue mass 18 (e.g., a lesion) can be segmented from volumetric images obtained, for example, from the CT/MRI/fluoroscopic examination, to create a surface model. Based upon a default resection margin inputted into the navigation system by a user, a segmented lesion label map can be dilated to the desired resection margin to create a surface model corresponding to the resection margin. Due to deformation of the lesion and the surrounding tissue, the resection margin can change, for example, due to movement of the patient. A linear elastic volumetric finite element model ("FEM") mesh can therefore be created from the surface model of the lesion and the resection margin. Using the FEM model, an estimate of the displacement of the other nodes of tissue mass 18 and resection margin 24 can be made, given the real-time position measurement of the fiducial sensor 10. Stiffness values may not be entirely accurate for the FEM model, and the FEM model may be constrained in one example to the tissue mass 18 and the surrounding tissue. Uncertainty measurements of the tissue mass 18 and the surrounding tissue deformation can therefore be provided to a user in real-time based upon the uncertainty in the estimated stiffness values of the FEM mesh.

Auditory, Visual, Quantitative And Haptic Cues

As described above, auditory, visual and haptic cues may be provided to the surgeon and/or the surgical device 26 to identify the resection margin 24 to ensure precise and complete resection of the tissue mass 18. For example, an audible source 52 may be configured to emit an audible signal. The audible source 52 may be in communication with the controller 48 that is configured to execute the stored program 50 to alter the audible signal based on the distance $D_3$ between the instrument sensor 28 and the fiducial sensor 10. The instrument sensor 28 uses the signal generated by the fiducial sensor 10 to enable the controller 48 to execute the stored program 50 to calculate the distance $D_3$, shown in FIG. 9, between the fiducial sensor 10 and the instrument sensor 28 such that when the surgical device 26 is below a threshold value of $D_3$, the audible signal is generated. The audible signal may be, for example a tone, beep or alarm. The audible signal may also increase in frequency or duty cycle as the distance $D_3$ decreases, such that as the surgical device 26 is navigated too close to the resection margin 24, the audible signal's frequency or duty cycle increases.

In addition to the auditory cues, visual cues may also be provided to the user on one or more displays 54 in communication with the controller 48. The one or more displays 54 may include, for example, visual cues provided on an endoscopic display or a separate monitor. For example, the endoscopic display or the separate monitor may be configured to emit a visual signal. The endoscopic display or the separate monitor may be in communication with the controller 48 that is configured to execute a stored program 50 to alter the visible signal based on the distance $D_3$ between the instrument sensor 28 and the fiducial sensor 10. The instrument sensor 28 uses the signal generated by the fiducial sensor 10 to enable the controller 48 to execute the stored program 50 to calculate the distance $D_3$, shown in FIG. 9, between the fiducial sensor 10 and the instrument sensor 28 (e.g., near the tip of the surgical device 26), and/or between the instrument sensor 28 (e.g., near the tip of the surgical device 26) and a vector normal to the hook structure 16, such that when the surgical device 26 is below a threshold value of $D_3$, the visual signal is generated. The visual signal may be, for example, a solid or flashing light shown on the one or more displays 54, such as the endoscopic display or the separate monitor. The visual signal may also increase in frequency or brightness, for example, as the distance $D_3$ decreases, such that as the surgical device 26 is navigated too close to the resection margin 24, the visual signal's frequency and/or brightness increases. Further, the distances from the tip, mid or base of the cutting surface of the instrument can also be determined based on a stored program and displayed to the user. Such a display of distance numerics may sometimes be referred to herein as a so-called quantitative cue.

In one non-limiting example, the visual cue may be shown as a color changing sphere, for example, on one of the displays 54. The color changing sphere may be representative of the tissue resection margin 24, for example, such that the color changes based on the distance $D_3$ between the instrument sensor 28 and the fiducial sensor 10. Thus, as the instrument sensor 28 approaches the fiducial sensor 10, for example, the sphere may be shown in the display 54 in a first color. Likewise, as the instrument sensor 28 moves away from the fiducial sensor 10, the sphere may be shown on the display 54 in a second color, for example, thereby allowing the surgeon to appreciate, visually, the distance $D_3$ between the instrument sensor 28 and the fiducial sensor 10.

Figure 11:
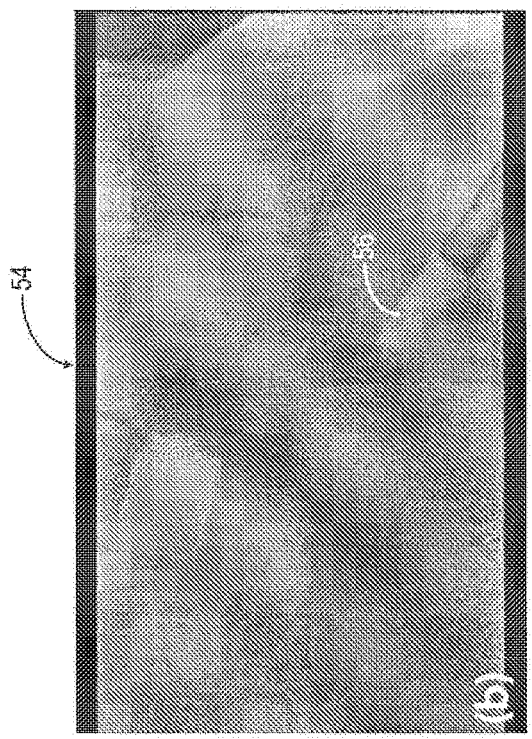
FIG. 11 is an example screenshot of a laparoscopy view of a tissue mass.
Figure 10:
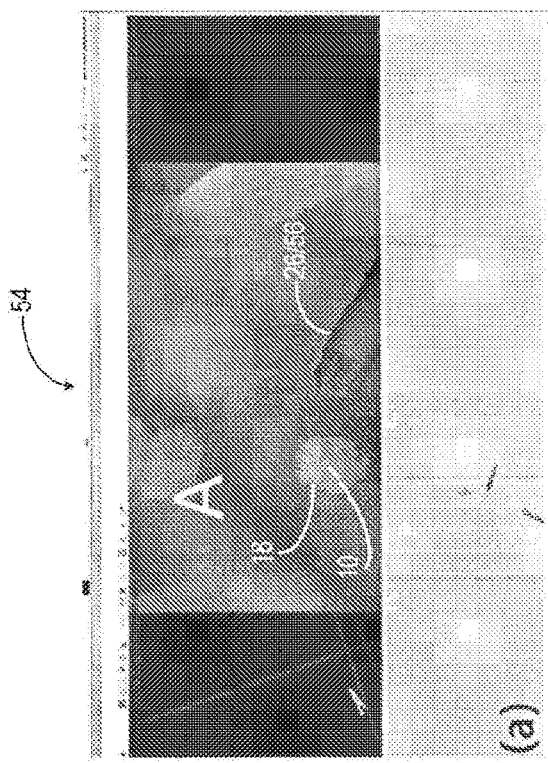
FIG. 10 is an example screenshot of a virtual endoscopy or "scope" view of a tissue mass overlaid on a laparoscopy view.

Although quantitative, visual, and auditory cues may be provided to the clinician to identify the distance of the resection margin 24 from the surgical instrument 26, the visual cue may further include a video overlay provided to the user on one or more of the displays 54 in communication with the controller 48. For example, a video overlay may be implemented to fuse the laparoscopy images and virtual endoscopy images to confirm the position of the fiducial sensor 10 and the tissue mass 18, as shown on the display 54 of FIG. 10. Based on the position of the laparoscope 56, as shown on the display 54 of FIG. 11, the virtual endoscopy video of the three dimensional anatomy can be generated. The focal length and field of view may be inputted to control the virtual endoscopy view generated using a visualization toolkit camera, for example, of the three dimensional view.

Haptic cues may also be provided to the user on the surgical device 26. For example, a piezoelectric actuator 46 may be attached to the handle 30 of the surgical device 26 that is configured to emit a haptic signal. The piezoelectric actuator 46 may be in electrical communication with the controller that is configured to execute a stored program to alter the haptic signal based on the distance $D_3$ between the instrument sensor 28 and the fiducial sensor 10. The instrument sensor 28 uses the signal generated by the fiducial sensor 10 to enable the controller to execute the stored program to calculate the distance $D_3$, shown in FIG. 9, between the fiducial sensor 10 and the instrument sensor 28 such that when the surgical device 26 is below a threshold value of $D_3$, the haptic signal is generated. The haptic signal may be, for example a vibration applied to the handle 30 of the surgical device 26. The haptic signal may also increase in amplitude and/or frequency, for example, as the distance $D_3$ decreases, such that as the surgical device 26 is navigated too close to the resection margin 24, the haptic signal's amplitude and/or frequency increases.

Application To Lung Cancer Surgery

Nearly 230,000 new cases of lung cancer are diagnosed each year in the United States, at an estimated cost of $12.1 billion to the healthcare system. Patients with lung cancer have 1-year and 5-year survival rates of 44% and 17%, respectively. For treatment of early stage small lesions, a parenchymal-sparing, minimally invasive Wedge Resection Surgery (WRS) or segmentectomy is becoming the preferred method of surgical resection over lobectomy. The preservation of healthy lung function becomes even more important when the lung physiology is compromised due to excessive smoking, old age, multiple lesions, previous lung surgery, cardiac comorbidity or Chronic Obstructive Pulmonary Disease (COPD). Although these approaches (i.e., WRS and segmentectomy) result in better lung function, the lesion recurrence rate is almost double that of a lobectomy, with significantly poorer 5-year survival rates. In addition, segmentectomy is associated with significant complications. The loco-regional recurrence and complications associated with segmentectomy may be attributed to the difficulty in accurately localizing and resecting the lesions in a deflated lung, and the difficulty in identifying the intersegmental plane. To avoid peri- and post-operative complications, precise anatomic landmarks (e.g., vascular and bronchial anatomic variations) need to be carefully identified and followed.

In the preceding sections, it is taught that a fiducial sensor 10 (e.g., a T-bar or J-bar assembly) is placed close to the lesion 18 in order to track the lesion in real-time. The surgical stapler (or other surgical device) 26 is also tracked in real-time using an instrument sensor 28 to precisely guide the resection of the lung lesion 18. More particularly, navigation software computes the distance of the surgical stapler to the fiducial sensor (e.g., the T-bar or J-bar assembly), 26 and hence the distance of the surgical stapler 26 to the lesion 18, and displays the distance measurement to the surgeon in real-time so as to ensure complete lesion resection. Further, the distances of the fiducial sensor 10 or the tumor surface to the tip, middle and base of the stapler cutting line (also sometimes referred to herein as a resection line) can also be computed and displayed in real-time.

Using The System To Identify A Specific Airway In The Lung So As To Assist A Surgeon In Identifying That Airway During Surgery From The Chest Side Of The Operation The system can also be used to identify a specific airway in the lung so as to assist a surgeon in identifying that airway during surgery from the chest side of the operation.

More particularly, the airways of the lung have a complex tree-like structure. See FIG. 12.

When treating a lesion in the lung, and particularly where the treatment may involve a resection of the lung in order to remove the lesion, it can be important to plan the resection relative to specific airways, i.e., to remove a specific airway, to avoid a specific airway, etc. Therefore, it can be important to know the location of relevant airways when conducting the resection surgery.

During bronchoscopy, it is possible to identify the location of the bronchoscope relative to specific airways, since the bronchoscope follows a descending path characterized by specific branching as the bronchoscope proceeds down the tree-like structure of the airways. However, the bronchoscope can typically traverse only a limited distance down the airways of the lung given its size and the progressively decreasing size of the airways. Furthermore, during surgery from the chest side of the operation, the visualization provided to the surgeon from the chest side is limited to a direct field of view and it can be highly problematic to identify, from the chest side, a specific airway due to the limited view provided to the surgeon from the chest side.

The present invention can be used to identify a specific airway in the lung so as to assist a surgeon in identifying that airway during surgery from the chest side of the operation.

Figure 13:
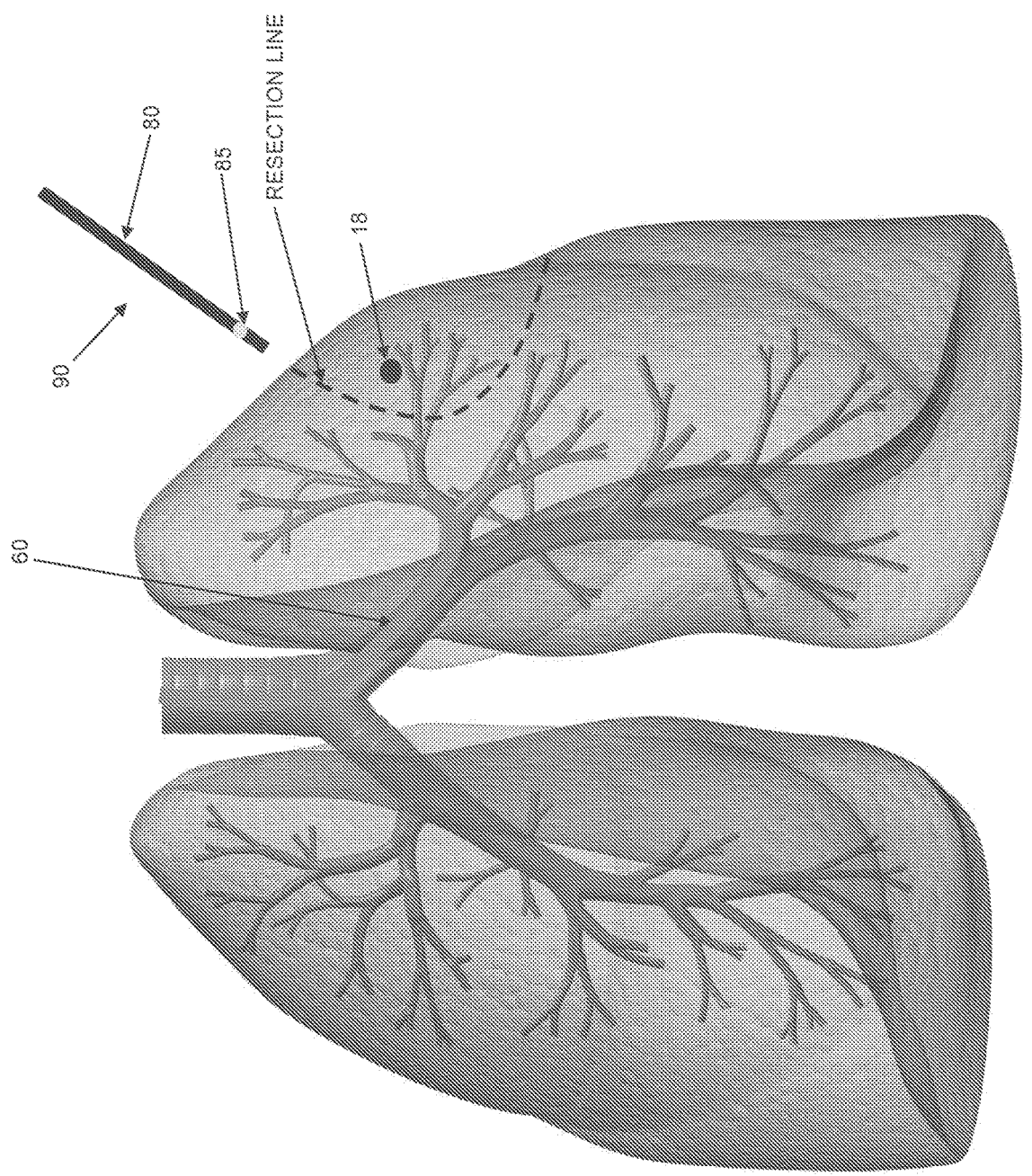
Figure 15:
Figure 14:
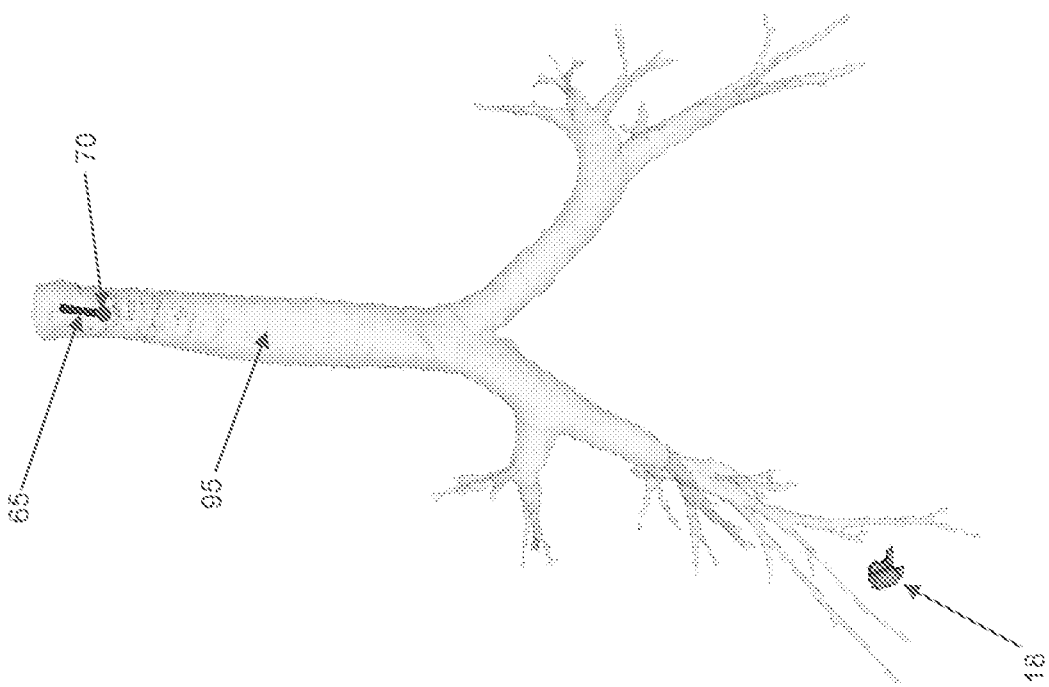
Figure 17:
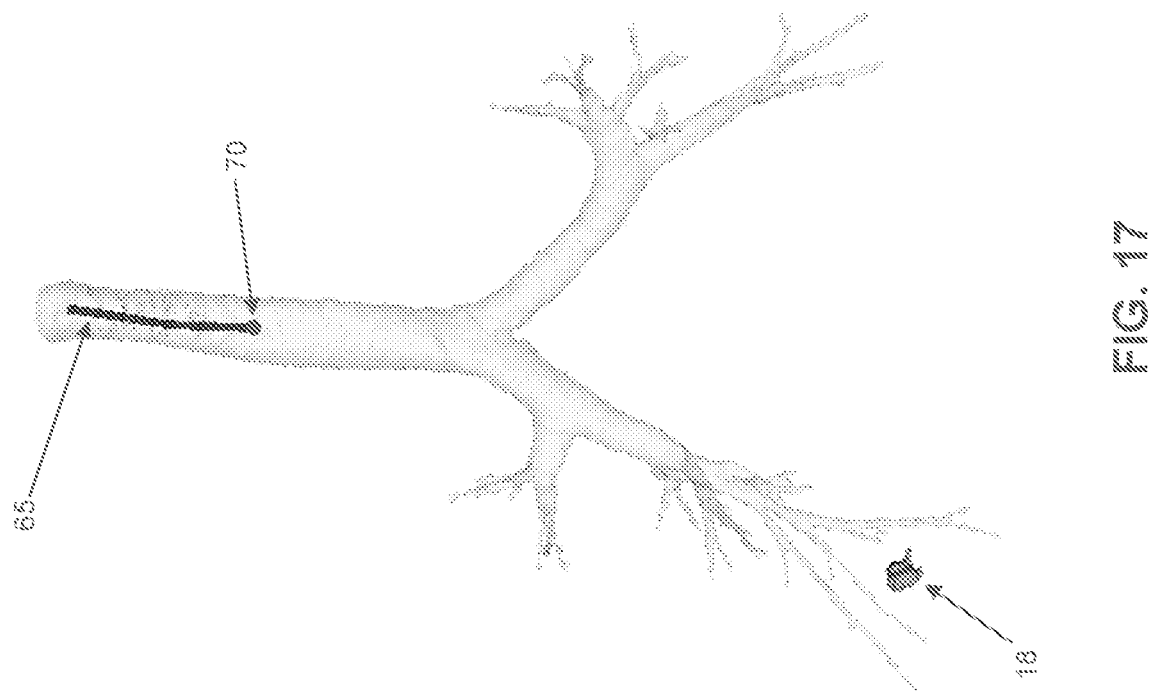
Figure 16:
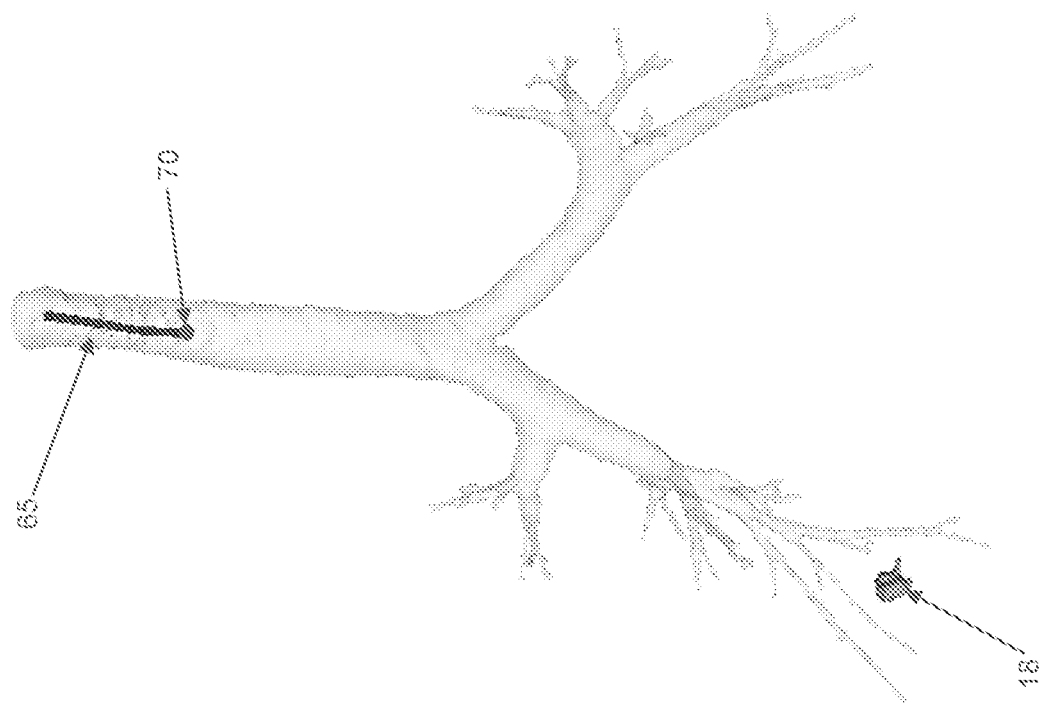
Figure 21:
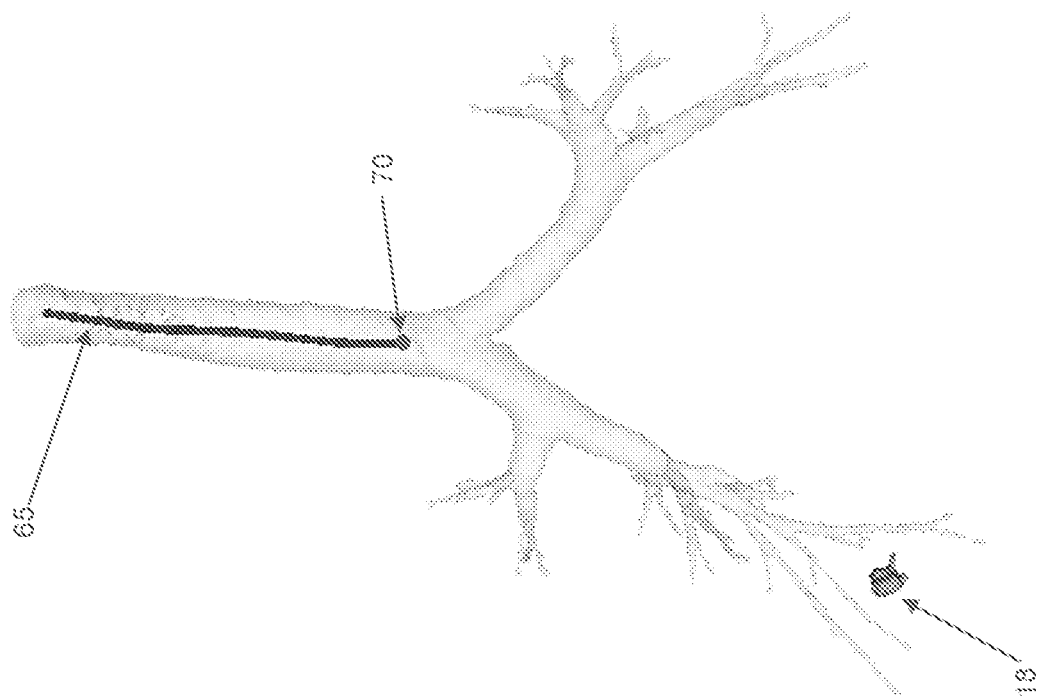
Figure 20:
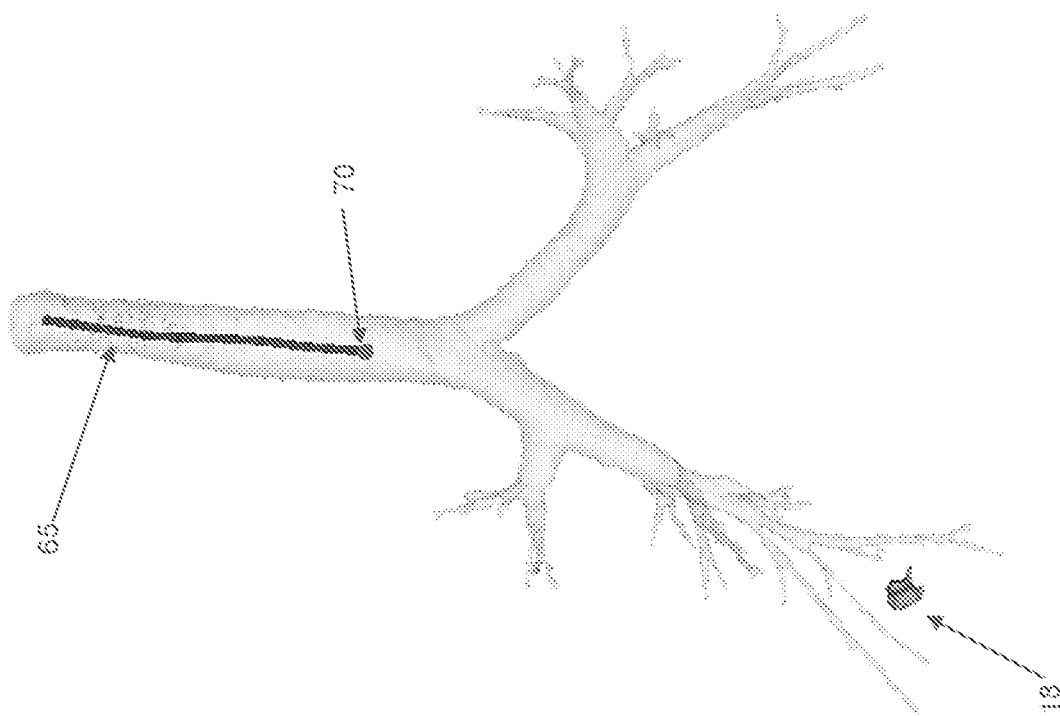
Figure 23:
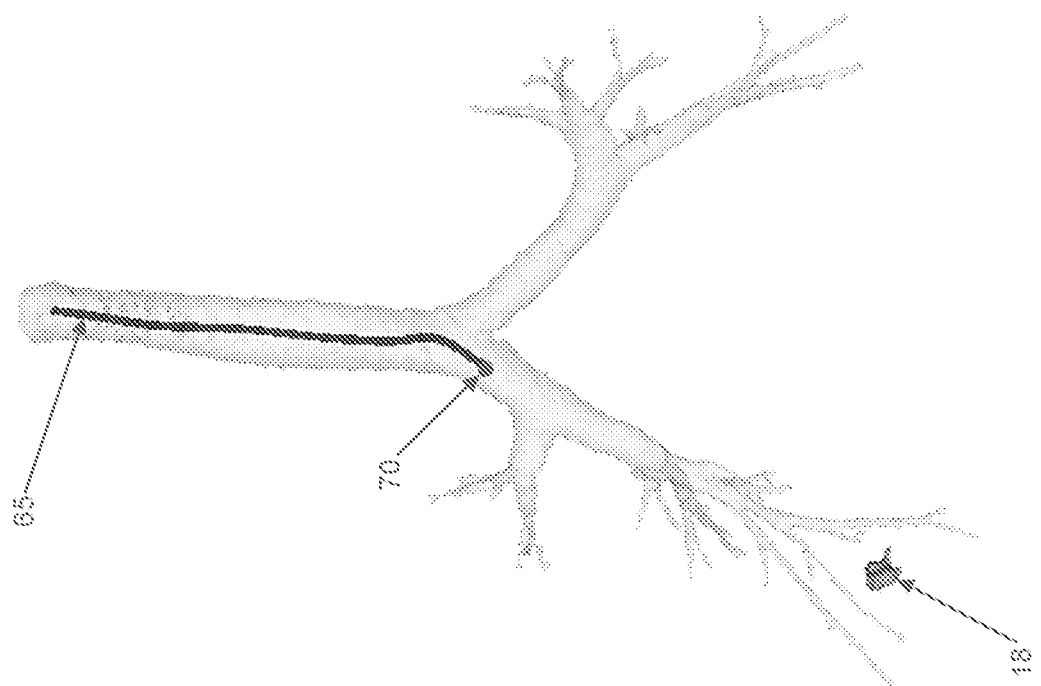
Figure 22:
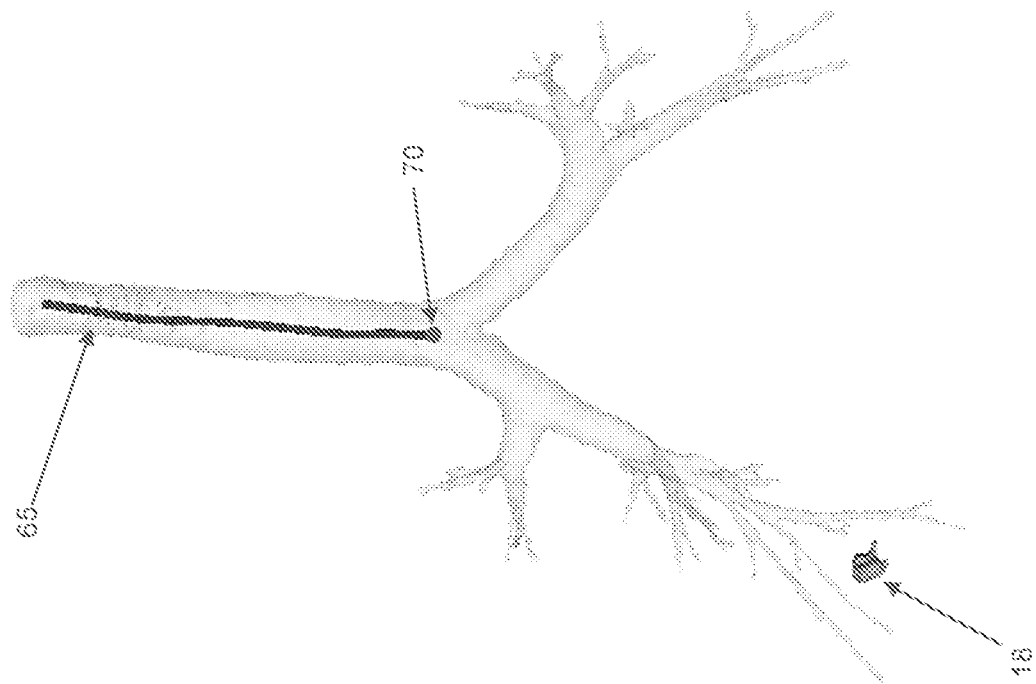
Figure 25:
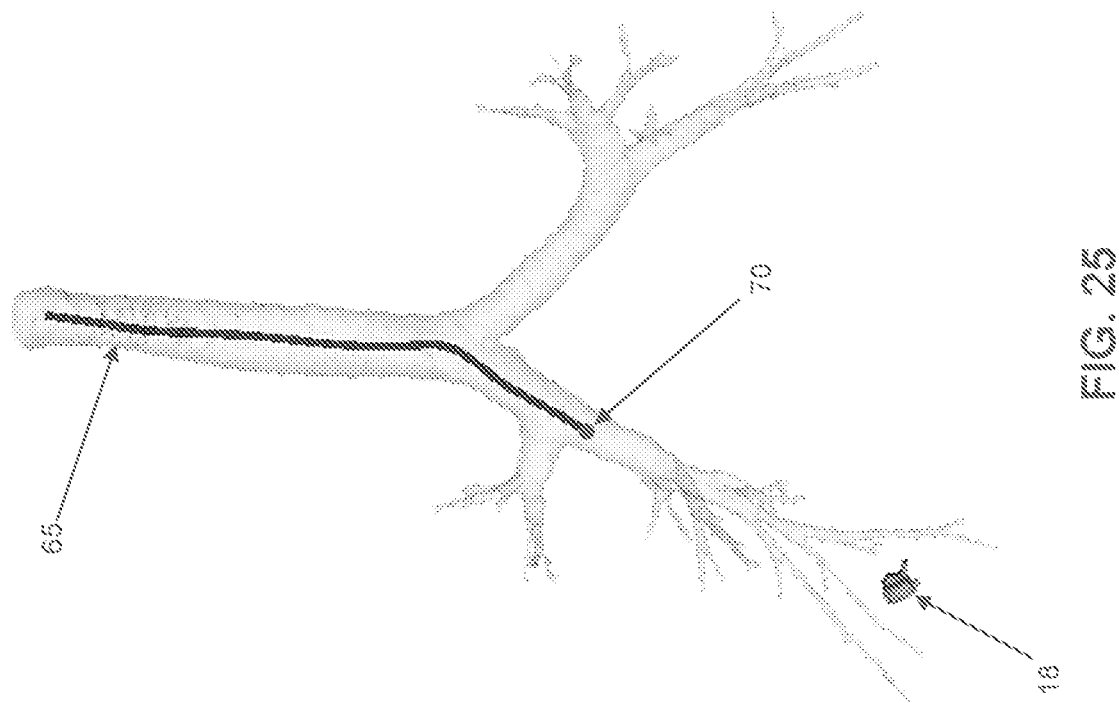
Figure 24:
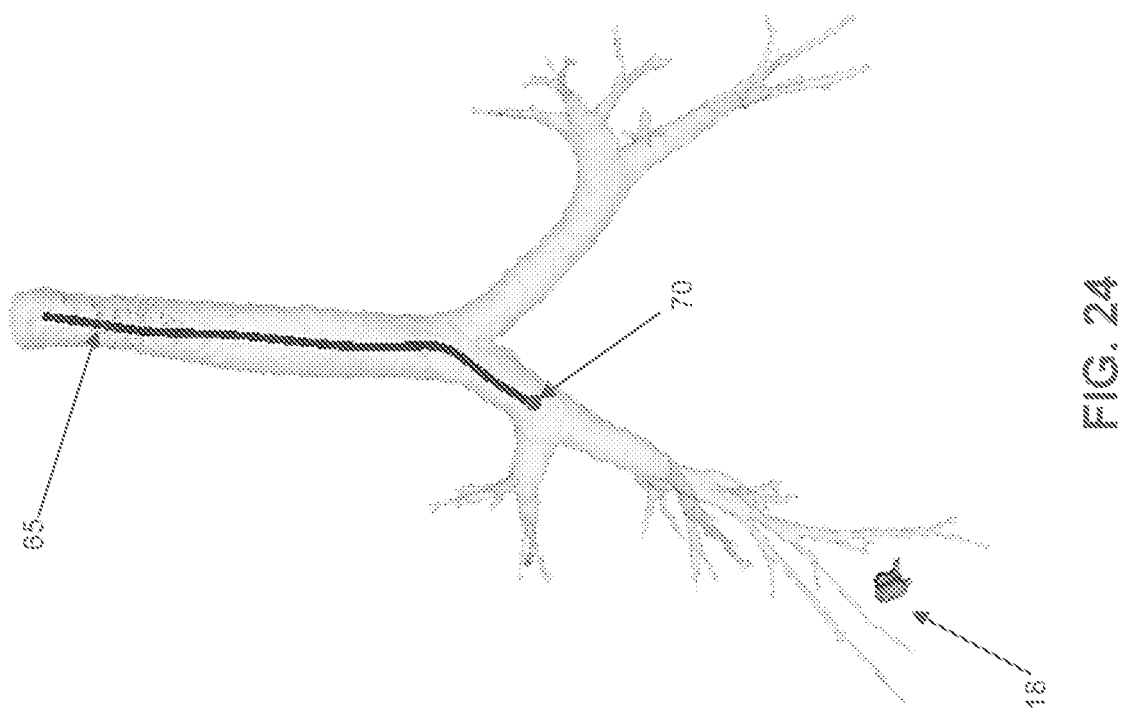
Figure 33:
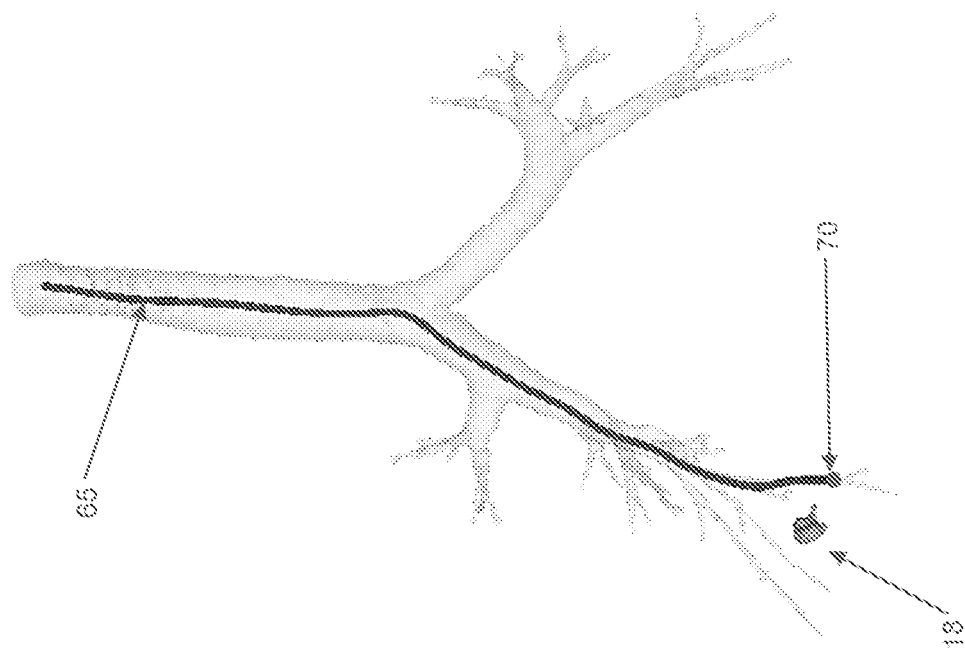
Figure 32:
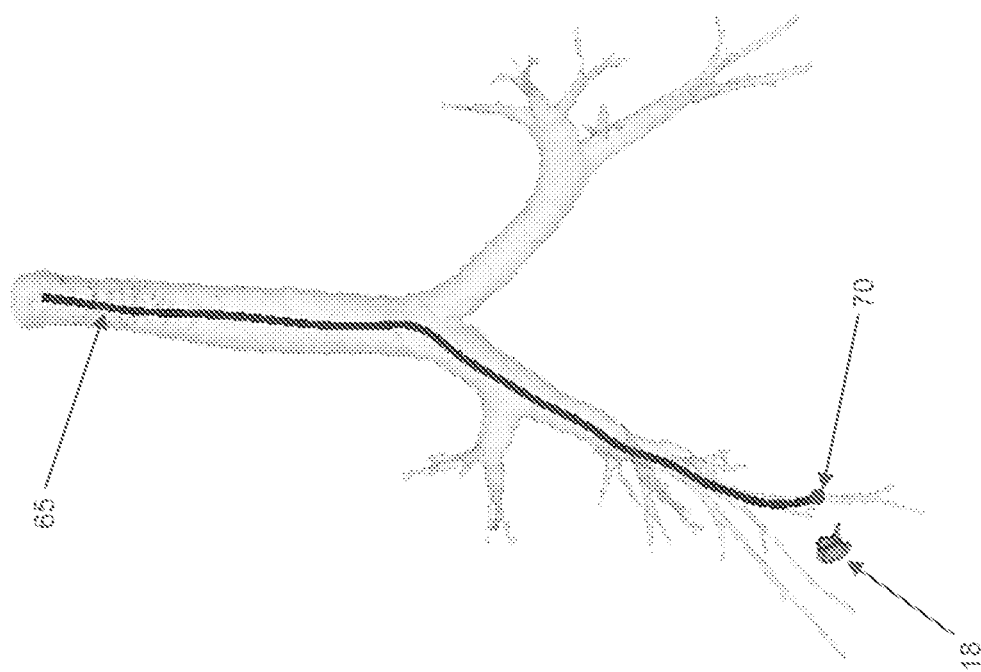

More particularly, and looking now at FIGS. 13, 13A and 13B, in this form of the invention, a bronchoscope 60 is used to position a catheter 65 carrying a sensor 70 (i.e., a "tracked catheter" 75) into a relevant airway of the lung. More particularly, in one preferred form of the invention, the bronchoscope 60 can be advanced through the airways under bronchoscopic guidance or by some other form of guidance, e.g., CT imaging, C-arm imaging, etc. until the bronchoscope 60 is advanced as far as possible toward the relevant airway. See FIG. 13. Then a tracked catheter 75 (i.e., a catheter 65 carrying a sensor 70) is advanced down the bronchoscope 60 and then out the end of the bronchoscope 60 into the relevant airway of the lung. See FIG. 13A. Note that, preferably, the tracked catheter 75 is not advanced through the bronchoscope 60 until after the bronchoscope 60 has been positioned in the lung in order to maintain maximum flexibility for the bronchoscope 60. Once the tracked catheter 75 has been advanced out the bronchoscope 60 and into position in the relevant airway, the bronchoscope 60 can be withdrawn. See FIG. 13B. Withdrawal of the bronchoscope 60 is generally desirable at this point since it can impede ventilation.

The bronchoscopic positioning of a sensor in a relevant airway of the lung (i.e., by bronchoscopically positioning a tracked catheter in a relevant airway of the lung) can then be used to define the lobar, segmental or subsegmental bronchus for surgery such as segmentectomy, lobectomy or wedge resection during the actual operation. More particularly, the position of the sensor identifying the bronchus (i.e., the sensor 70 on the tracked catheter 75) can be correlated with the position of another device (e.g., a surgical instrument) 80 carrying another sensor 85 (i.e., a tracked instrument 90) so that the surgeon can use the system to identify the correct bronchus for surgery from the chest side of the operation (when direct visualization is limited and frequently ambiguous with respect to specific airways). Thus, in this form of the invention, one sensor 70 is positioned on a catheter 65 which is inserted into a specific airway so as to identify the location of that specific airway, and another sensor 85 is positioned on a surgical instrument 80 which is advanced for surgery from the chest side of the operation, and the system then tracks the position of the surgical instrument 80 vis-à-vis the tracked catheter 75 (and hence vis-à-vis the position of the airway in which the tracked catheter 75 is positioned). In this way, the surgeon can identify the location of the surgical instrument 80 relative to the airway of interest (which is identified by the sensor 70 on the tracked catheter 75), even though direct visualization from the chest side of the operation may be limited and ambiguous with respect to specific airways. As a result, the surgeon can use the system to target the airway identified by the sensor 70 on the tracked catheter 75, or to avoid the airway identified by the sensor 70 on the tracked catheter 75, etc.

Significantly, the tracked catheter 75 may be inserted into a relevant airway of the lung while the lung is in a first configuration (e.g., an inflated configuration) and maintained in position within that airway while the lung transforms to a second configuration (e.g., a deflated configuration). This can be particularly advantageous when trying to identify a relevant airway of the lung during a limited access surgical procedure (e.g., where visualization is provided by a scope advanced into the chest) and the lung transforms between a first configuration and a second configuration.

Note that, if desired, the tracked catheter 75 may be inserted into the bronchoscope 60 before the bronchoscope 60 is advanced down the airways of the lung. However, as noted above, it is generally desirable to insert the tracked catheter 75 into the bronchoscope 60 after the bronchoscope 60 has been positioned in the lung since this provides maximum flexibility to the bronchoscope 60.

Note also, if desired, the bronchoscope 60 may be left in position in the lung after the tracked catheter 75 has been advanced into the relevant airway. However, as noted above, in many cases it is desirable to remove the bronchoscope 60 after the tracked catheter 75 has been advanced into the relevant airway since this provides better ventilation of the lung.

In addition to the foregoing, it should also be appreciated that, if desired, the bronchoscope 60 itself can carry a sensor (not shown), such that the bronchoscope 60 itself can be tracked in the airways of the lung. This approach can be useful where the bronchoscope 60 is able to advance into the airway of interest, e.g., where the airway of interest is a relatively large airway which can be directly accessed by the bronchoscope 60.

Note that, if desired, the tracked catheter 75 (and/or a tracked bronchoscope) may also be used to map a plurality of airways in the lung while the lung is in a given configuration (e.g., a first, inflated configuration).

In one form of the invention, a fiducial sensor 10 (e.g., a T-bar or J-bar assembly) is placed within the lung while the lung is in a first (e.g., inflated) configuration; a tracked catheter 75 is placed in a selected airway of the lung while the lung is in its first (e.g., inflated) configuration; the relative dispositions of the fiducial sensor 10 and the tracked catheter 75 are determined while the lung is in its first (e.g., inflated) configuration; the lung is transformed to a second (e.g., deflated) configuration; the relative dispositions of the fiducial sensor 10 and the tracked catheter 75 are determined while the lung is in its second (e.g., deflated) configuration; and the change in the relative dispositions of the fiducial sensor 10 and the tracked catheter 75 is determined after the lung transforms from its first (e.g., inflated) configuration to its second (e.g., deflated) configuration and used to estimate the extent of lung deformation and the location of lung structures when the lung is in its second (e.g., deflated) configuration.

Mapping And Tracking Of The Surrounding Airways

The foregoing system can be enhanced by mapping and tracking the surrounding airways (along with the lesion) so as to ensure that the correct segment of the lung is excised. This is because during deflation of the lung, the anatomy will shift and the tissue section to be excised may not be obvious to the surgeon.

The procedure for mapping and tracking the airways of the lung may be done as follows.

Figure 35:
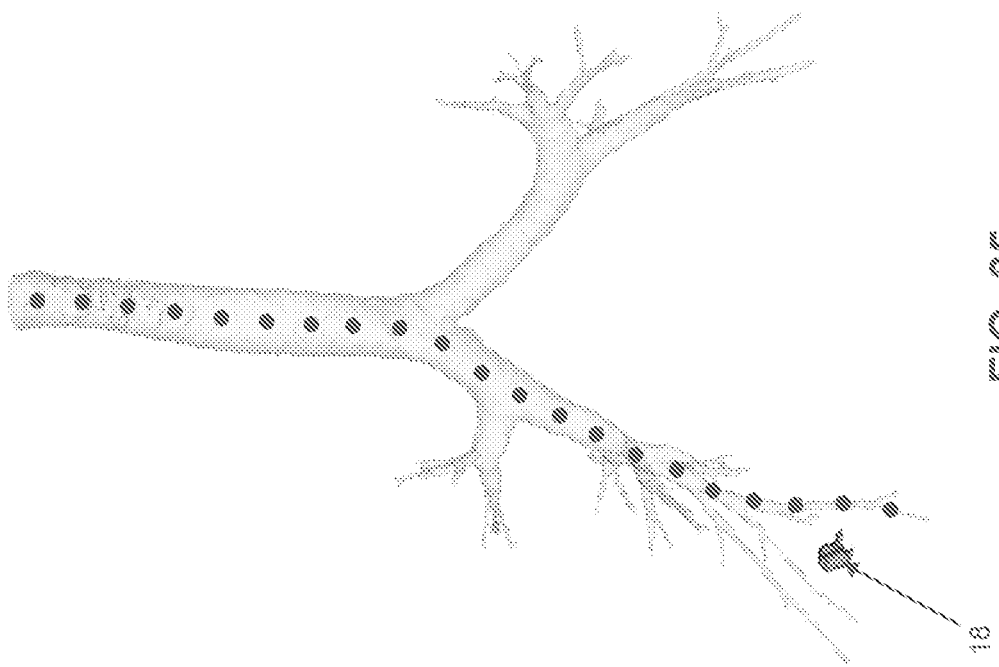
Figure 34:
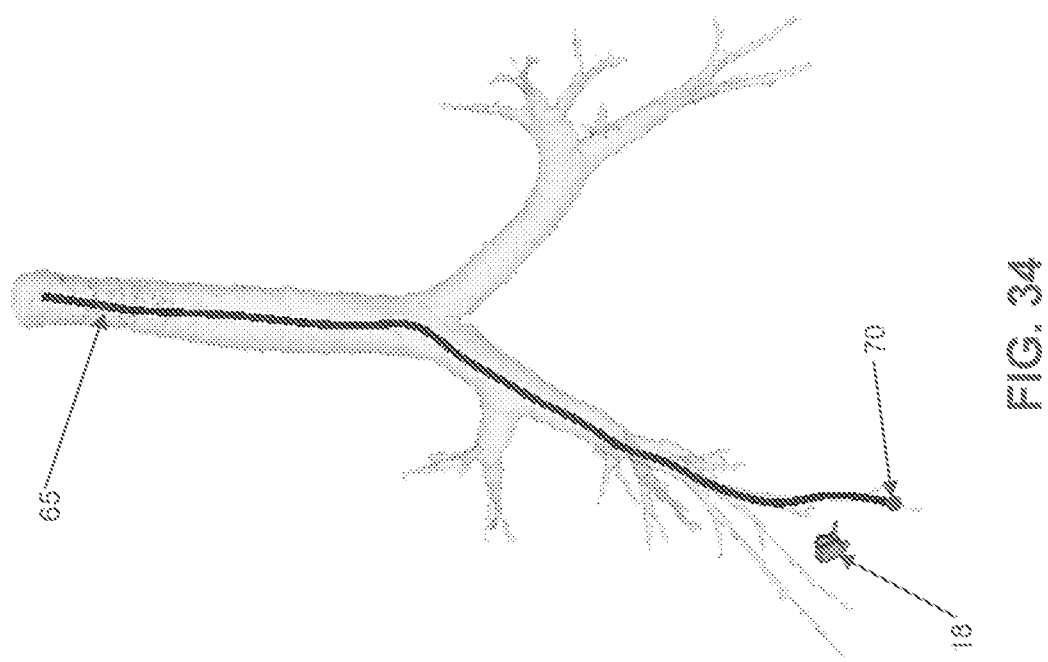

First, the patient is placed in the supine position. Then, bronchoscopically, a flexible catheter 65 having an on-board catheter sensor 70 is placed in the nearest/target bronchus of the lung segment containing the lesion 18. This is done either by identifying the correct bronchus visually or by some form of guidance (e.g., CT imaging, C-arm imaging, etc.). The tracked catheter 75 is inserted into the targeted bronchus near to the mass of the lesion 18, and as the catheter 65 is inserted, the trajectory of the catheter 65 is logged using the on-board catheter sensor 70 and an electromagnetic tracker system configured to identify the position and orientation of the catheter sensor 70 (and hence the position and orientation of the catheter 65). This trajectory marks the position of the airway 95 in the coordinate space of the electromagnetic tracker system. See FIGS. 14-34. The successive detected locations of the catheter sensor 70 as the catheter 65 advances down the airway 95 can be concatenated so as to provide the centerline of the targeted airway. See FIG. 35.

Figure 36:
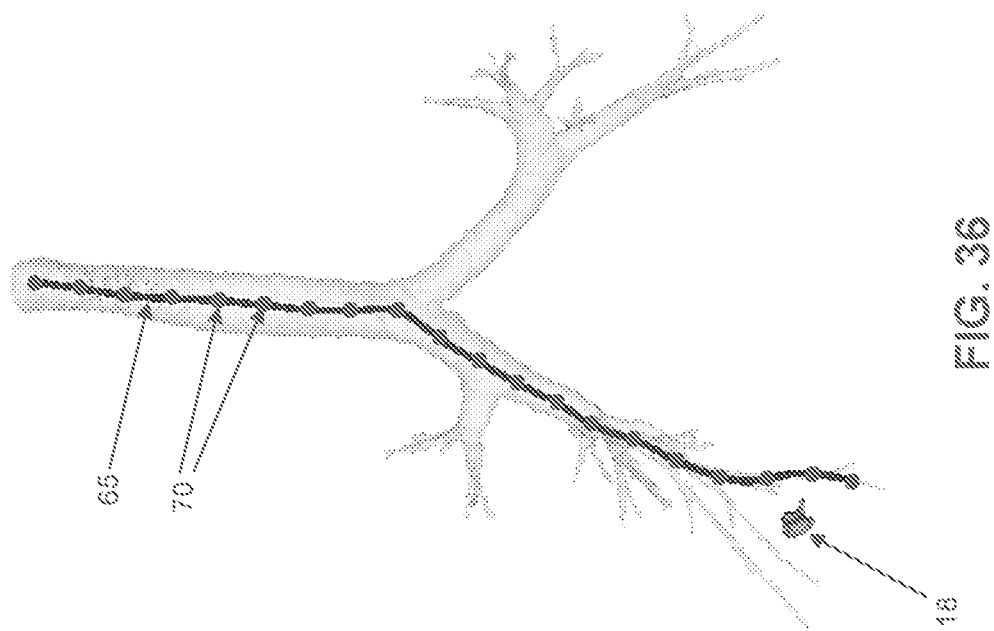
FIGS. 36 and 37 are schematic views showing another way that a tracked catheter can be used to identify the location of an airway.
Figure 37:
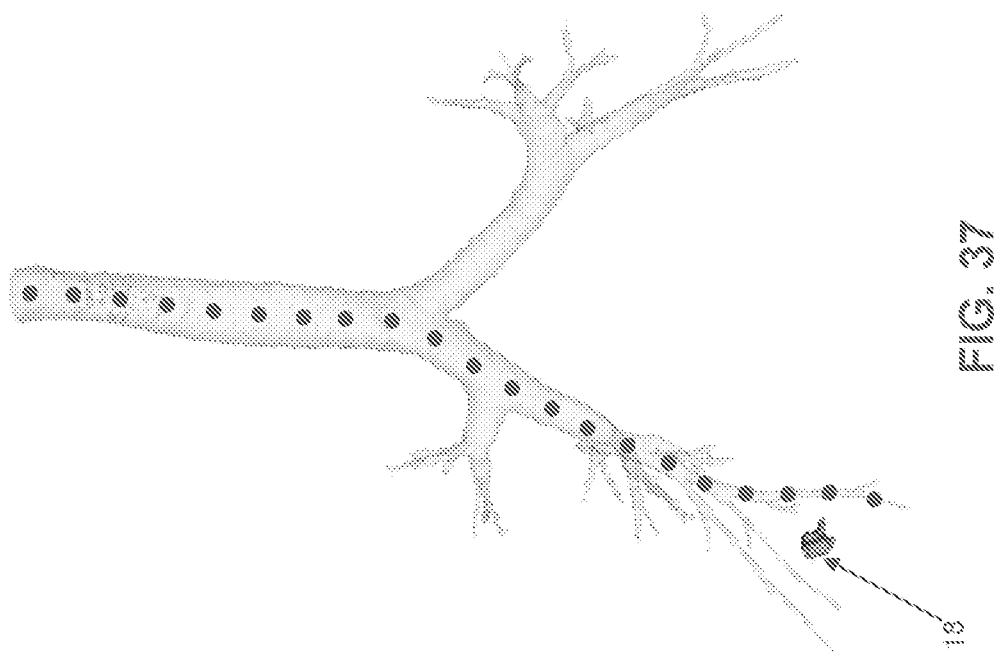

Alternatively, the catheter 65 can comprise a plurality of catheter trackers 70 located along its length so that airway mapping can be conducted by simply logging the locations of the various catheter sensors 70 after the catheter 65 has been fully inserted in an airway. See FIGS. 36 and 37. Note that the catheter 65 can be advanced through the airways under bronchoscopic guidance or by some other form of guidance, e.g., CT imaging, C-arm imaging, etc.

The process can then be repeated with adjacent airways so as to map out the airways surrounding the lesion.

Once the mapping of the relevant airways has been completed, the position of the fiducial sensor 10 (e.g., the T-bar or J-bar assembly or similar tracker) and mapped airways are recorded in the inflated lung (and, ultimately, in the deflated lung).

Figure 38:
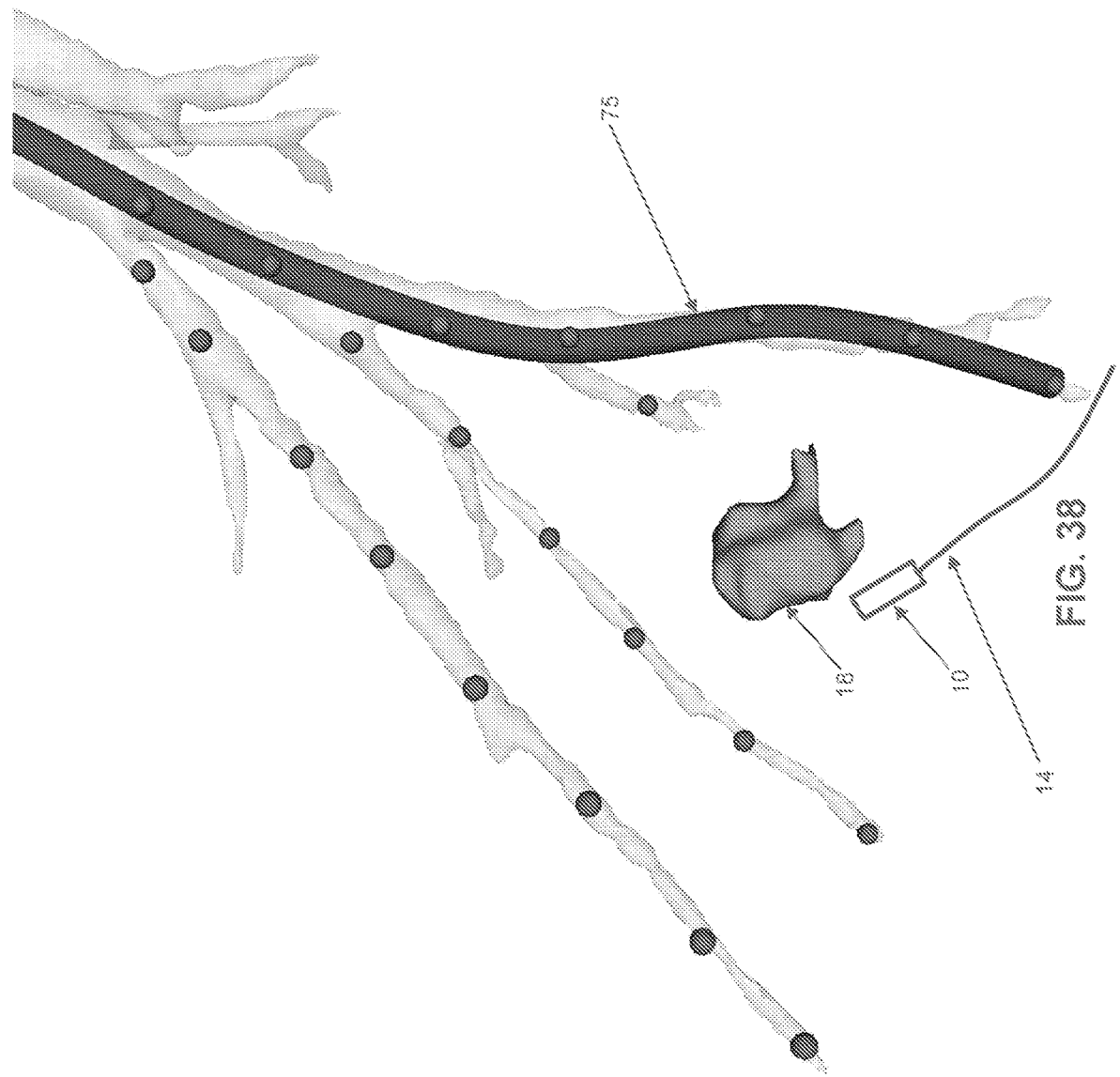
FIG. 38 is a schematic view showing an anatomical site containing a lesion, a fiducial sensor and a tracked catheter.

Thereafter, with a fiducial sensor 10 next to the lesion 18 and the tracked catheter 75 disposed in a critical airway near the lesion, the lung is collapsed prior to the start of the surgery. The fiducial sensor 10 (e.g., the T-bar or J-bar assembly) and the tracked catheter 75 are tracked in real-time as the lung is collapsed. See FIG. 38. The position of the fiducial sensor 10 (e.g., the T-bar or J-bar assembly) and the critical airway (e.g., the airway containing the tracked catheter 75) is recorded in the deflated lung. Using a finite element-based particle filter or FEM deformation algorithm, the spatial translation of the fiducial sensor 10 (e.g., the T-bar or J-bar assembly) and the critical airway from the inflated condition to the deflated condition is estimated. A smooth deformation field around the critical airway is estimated. The deformation field is then applied to the other airways mapped in the inflated lung so as to estimate the position of those other airways in the deflated lung. The "deformed" airways (i.e., the airways in the deflated lung) are displayed to the surgeon in the navigation system, along with the lesion, to precisely guide the surgical stapler 26 to the optimal resection margin while ensuring that critical anatomy is spared. This approach also, even without stapler navigation, helps define the correct segment for resection (as well as the correct bronchial segment to resect or not resect as part of the planned operation). Once the appropriate bronchial segment is identified in the thoracoscopic, or thoracic point of view, the catheter 65 may be removed prior to any surgical resection, by simply pulling it out of the airway from the mouth, nose or endotracheal tube.

In one aspect of the invention, a plurality of lumens in a deformable anatomical structure may be mapped and tracked by:

providing a virtual model of the anatomical structure while the anatomical structure is in a first configuration;

while the anatomical structure is in the first configuration, positioning a tracked catheter in one of the lumens in the anatomical structure which is to be mapped and tracked, and determining the position of the tracked catheter in that lumen so as to map the position of that lumen;

repeating the foregoing step for each of the lumens in the anatomical structure which is to be mapped and tracked so that those lumens are mapped;

supplementing the virtual model with the mapped lumens, whereby to provide a supplemented virtual model of the anatomical structure and the mapped lumens while the anatomical structure is in its first configuration;

maintaining the tracked catheter in one of the mapped lumens of the anatomical structure as the anatomical structure is deformed from its first configuration to a second configuration;

determining the position of the tracked catheter in the anatomical structure while the anatomical structure is in the second configuration; and modifying the supplemented virtual model so as to represent the anatomical structure and the mapped lumens while the anatomical structure is in its second configuration, whereby to provide a modified supplemented virtual model, wherein modification is effected by:

determining the spatial transformation of the tracked catheter as the anatomical structure deforms from its first configuration to its second configuration; and applying the spatial transformation of the tracked catheter to the mapped lumens of the supplemented virtual model so as to provide the modified supplemented virtual model of the anatomical structure and the mapped lumens while the anatomical structure is in its second configuration.

In another aspect of the invention, a selected lumen in a deformable anatomical structure may be mapped and tracked by:

positioning a tracked catheter in the selected lumen of the anatomical structure while the anatomical structure is in a first configuration;

determining the position of the tracked catheter while the anatomical structure is in the first configuration;

scanning the anatomical structure and the tracked catheter positioned in the selected lumen of the anatomical structure while the anatomical structure is in the first configuration;

creating a virtual model of the scanned anatomical structure and the tracked catheter positioned in the selected lumen of the anatomical structure while the anatomical structure is in its first configuration;

maintaining the tracked catheter in position within the selected lumen of the anatomical structure while the anatomical structure deforms to a second configuration;

determining the position and orientation of the tracked catheter while the anatomical structures is in its second configuration, whereby to determine the position of the selected lumen of the anatomical structure while the anatomical structure is in the second configuration; and adjusting the virtual model so as to represent the anatomical structure and the selected lumen while the anatomical structure is in its second configuration, whereby to provide an adjusted virtual model, wherein modification is effected by:

determining the spatial transformation of the tracked catheter as the anatomical structure deforms from its first configuration to its second configuration; and applying the spatial transformation of the tracked catheter to the selected lumen of the virtual model so as to provide the adjusted virtual model of the anatomical structure and the selected lumen while the anatomical structure is in its second configuration.

Bronchoscopic Deployment Of The Fiducial Sensor

Figure 39:
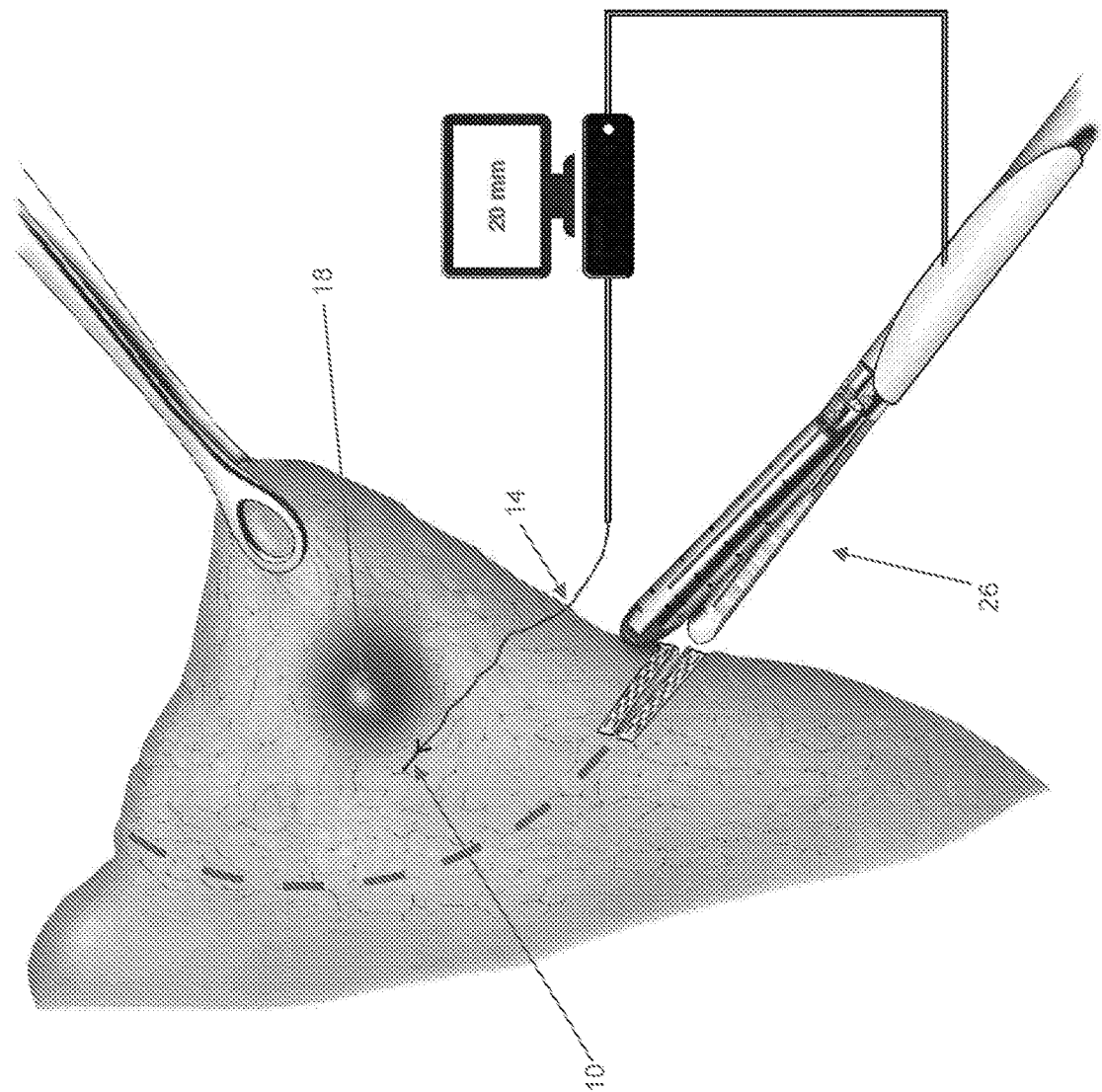
FIG. 39 is a schematic view showing a fiducial sensor deployed using a percutaneous access.

In the system described above, the fiducial sensor 10 (e.g., the T-bar or J-bar assembly) is described as being deployed percutaneously. See FIG. 39. However, if desired, the fiducial sensor 10 (e.g., the T-bar or J-bar assembly) can be deployed via a bronchoscopic approach, or open chest approach or VATS approach.

Figure 40:
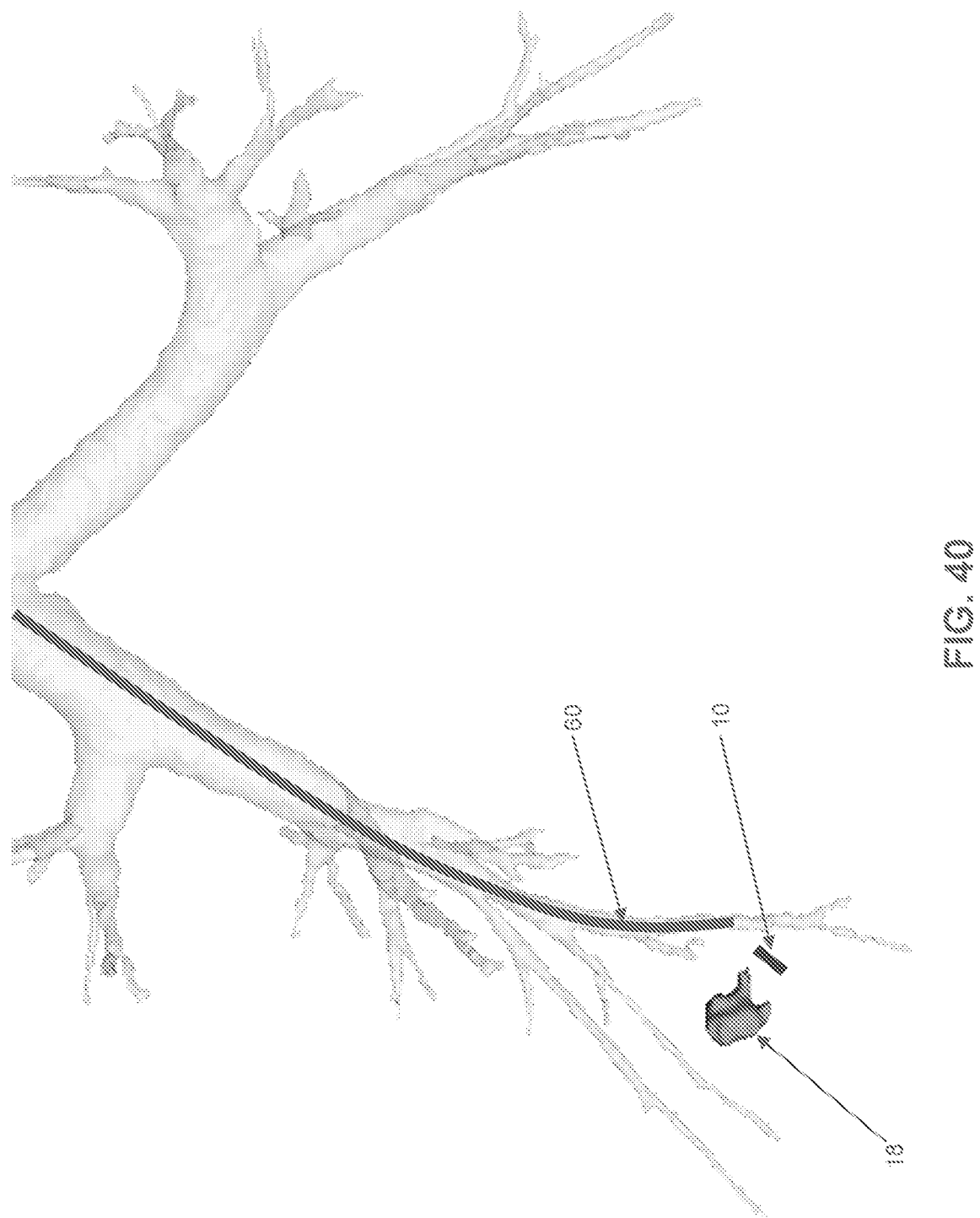
FIGS. 40 and 41 are schematic views showing a wireless fiducial sensor deployed through a bronchoscope.
Figure 41:
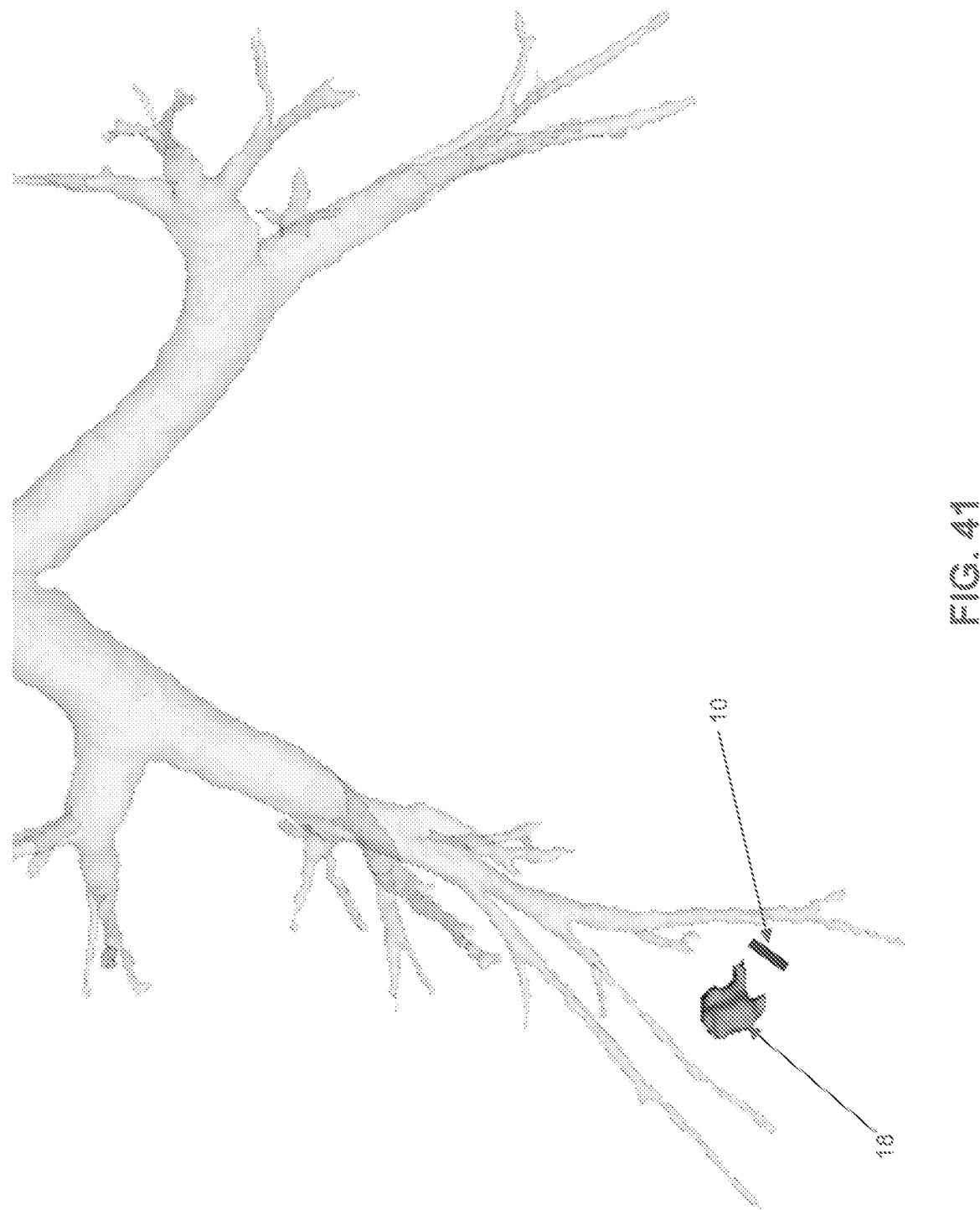

More particularly, the fiducial sensor 10 (e.g., the T-bar or J-bar assembly) is a metal anchor with a wireless electromagnetic sensor embedded within a hook-like structure. The metal anchor could be made from superelastic material, for example nitinol, or it could be made from stainless steel. The fiducial sensor 10 (e.g., the T-bar or J-bar assembly) is placed within a long flexible hollow tube with a bevel tip at the end. This hollow tube is inserted through the working channel of the bronchoscope 60. Under real-time image guidance using the navigation system, the wireless fiducial sensor 10 (e.g., the T-bar or J-bar assembly) is navigated through the airways using the bronchoscope 60 and placed close to the lesion. See FIG. 40. Once the fiducial sensor 10 (e.g., the T-bar or J-bar assembly) has been deployed close to the lesion 18, the bronchoscope 60 (and the hollow tube extending through the working channel of the bronchoscope) is removed. See FIG. 41. Thereafter, the lung is collapsed and the lesion 18 is tracked in real-time using the fiducial sensor 10 (e.g., the T-bar or J-bar assembly). The surgical stapler (not shown) is also tracked in real-time using the instrument sensor attached to the surgical stapler. Note that the surgical stapler is tracked in the same reference frame as the fiducial sensor 10 (e.g., the T-bar or J-bar assembly). The surgical stapler can then be navigated to the optimal resection margin using the navigation system.

Figure 42:
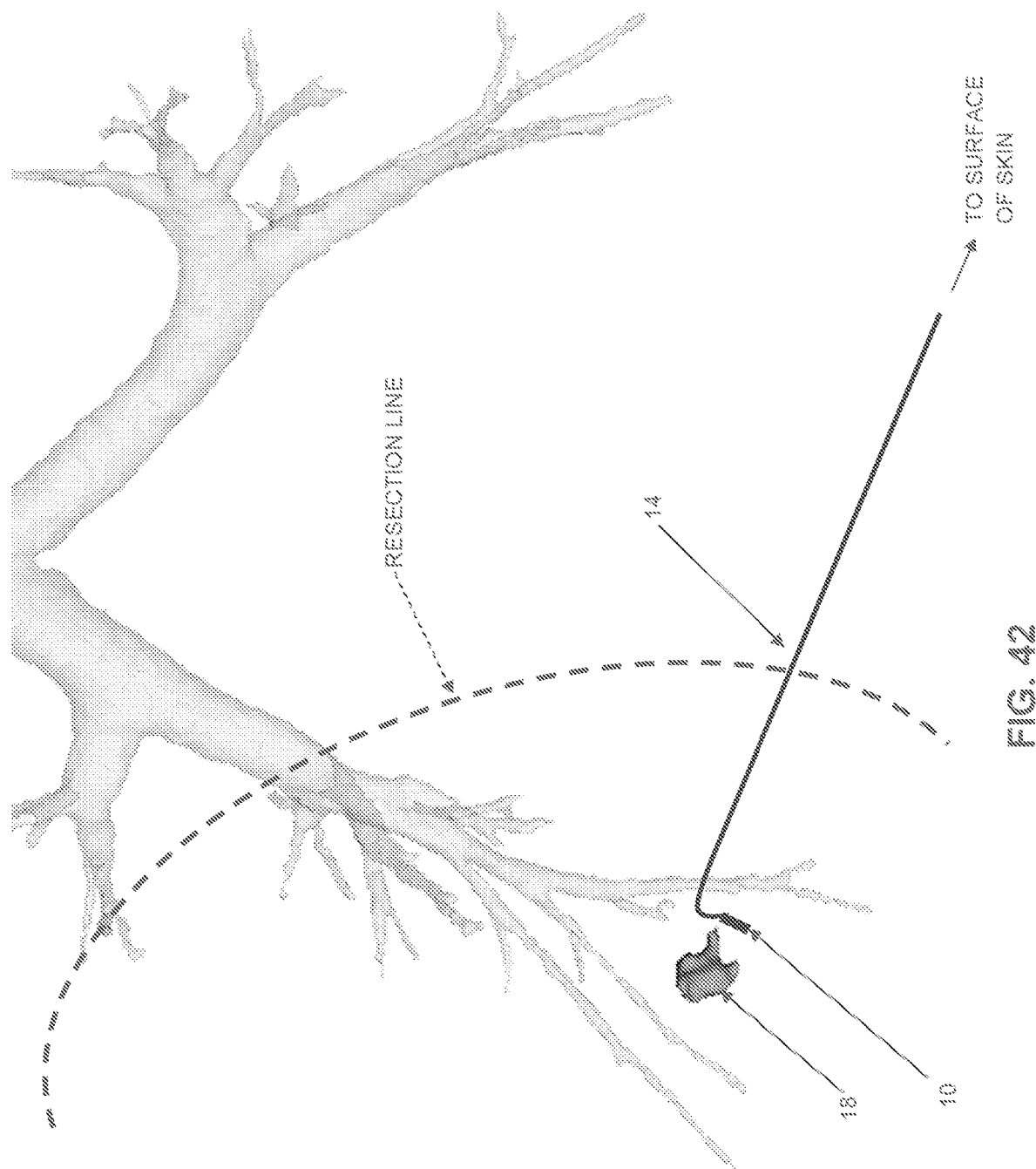
FIG. 42 is a schematic view showing a wire-based fiducial sensor deployed through a bronchoscope and having its wire then pushed bronchoscopically, under image guidance, through the lung parenchyma to the surface of the skin.

Alternatively, if desired, the fiducial sensor 10 (e.g., the T-bar or J-bar assembly) could carry a wire-based electromagnetic sensor. In this case, after the fiducial sensor 10 (e.g., the T-bar or J-bar assembly) has been deployed, the wire 14 of the fiducial sensor is then pushed bronchoscopically, under image guidance, through the lung parenchyma to the surface of the skin at the nearest spot to the lesion 18 so as to mark the lesion 18. See FIG. 42.

Figure 43:
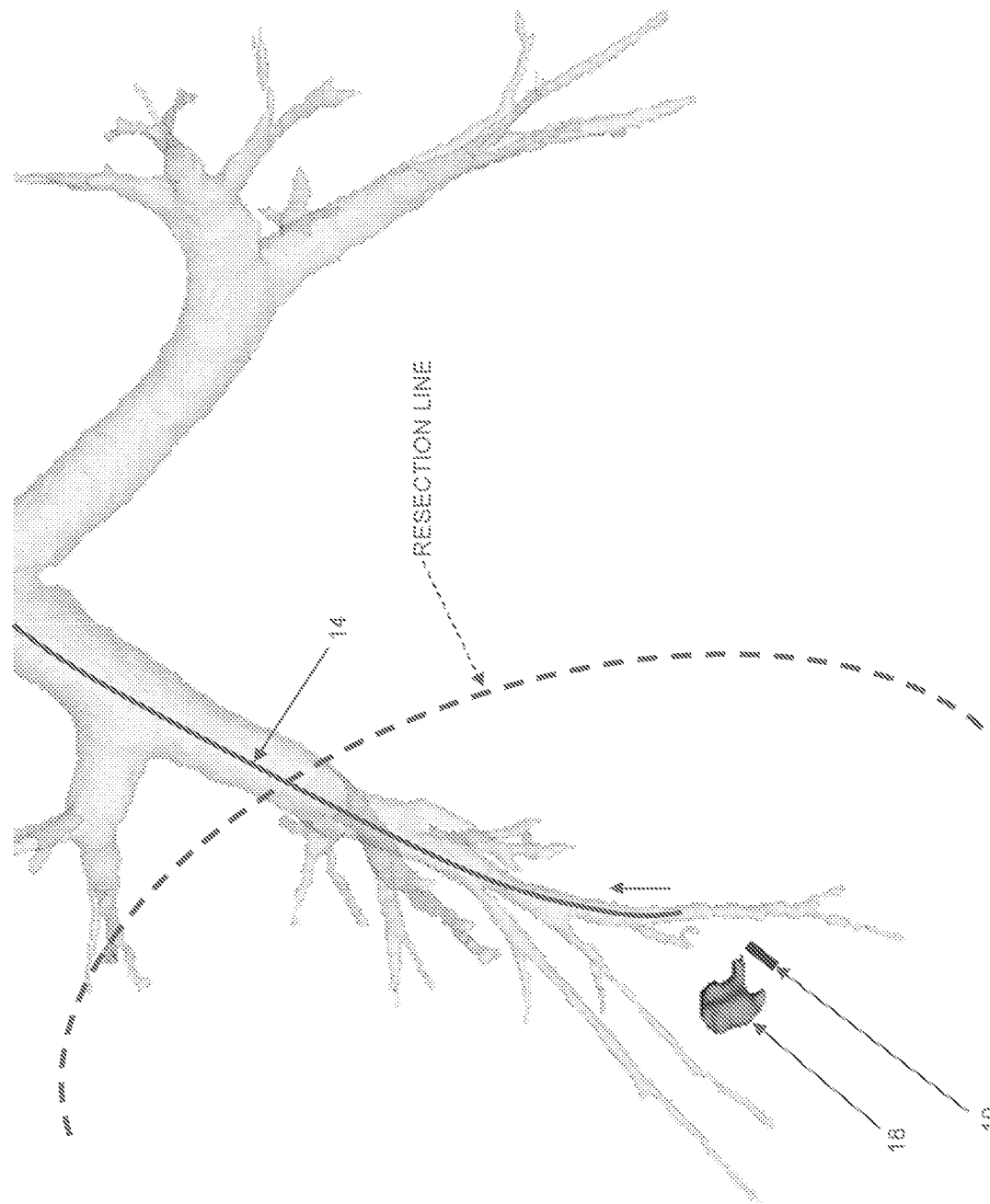
FIG. 43 is a schematic view showing a wire-based fiducial sensor deployed through a bronchoscope and having its wire thereafter detached from the fiducial sensor and withdrawn up the airway.

In still another form of the invention, where the fiducial sensor 10 (e.g., the T-bar or J-bar assembly) carries a wire-based electromagnetic sensor, the wire 14 has a detachable connection to the electromagnetic sensor. Then, after the stapler has been used to establish the resection line, the wire 14 is detached from the electromagnetic sensor and pulled back up the airway. See FIG. 43.

In yet another form of the invention, and looking now at FIGS. 44-52, a bronchoscopic sensor unit 100 is provided for bronchoscopic deployment of fiducial sensor 10 into tissue mass 18 or adjacent to tissue mass 18.

Figure 44:
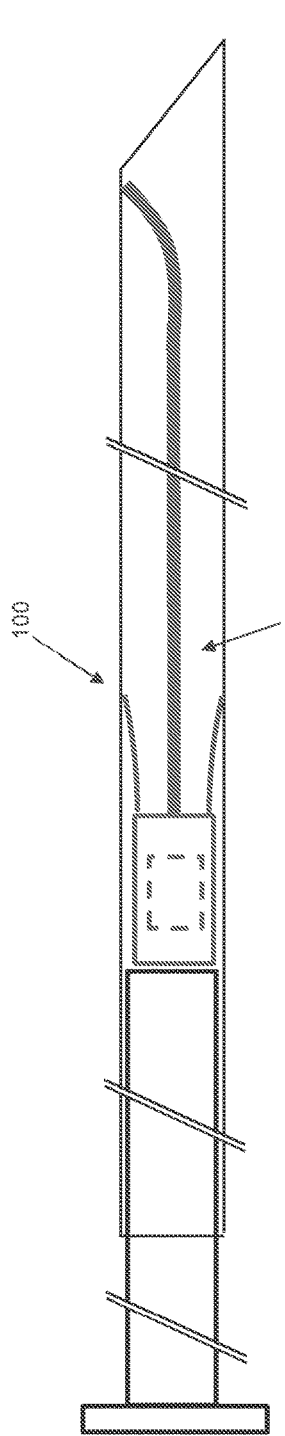
FIGS. 44-46 are schematic views showing apparatus for another approach for bronchoscopic deployment of the fiducial sensor into tissue (e.g., bronchoscopic deployment of the fiducial sensor into the tissue mass or adjacent to the tissue mass).
Figure 45:
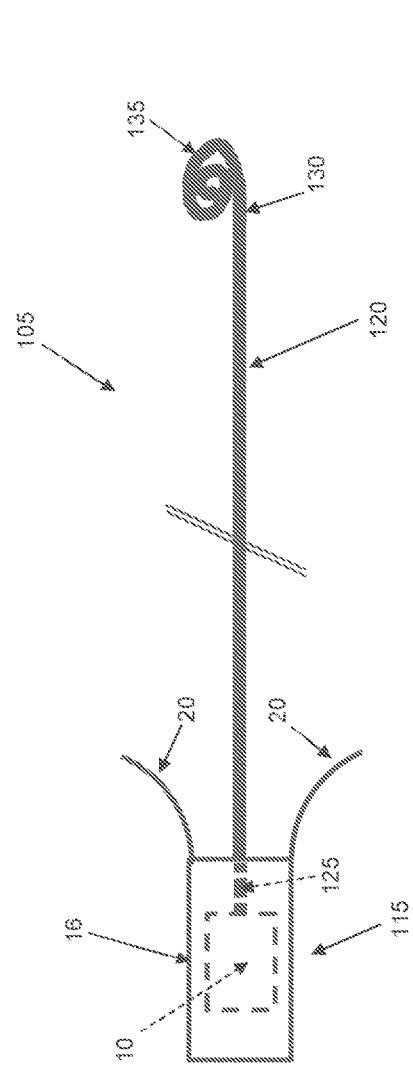
Figure 46:
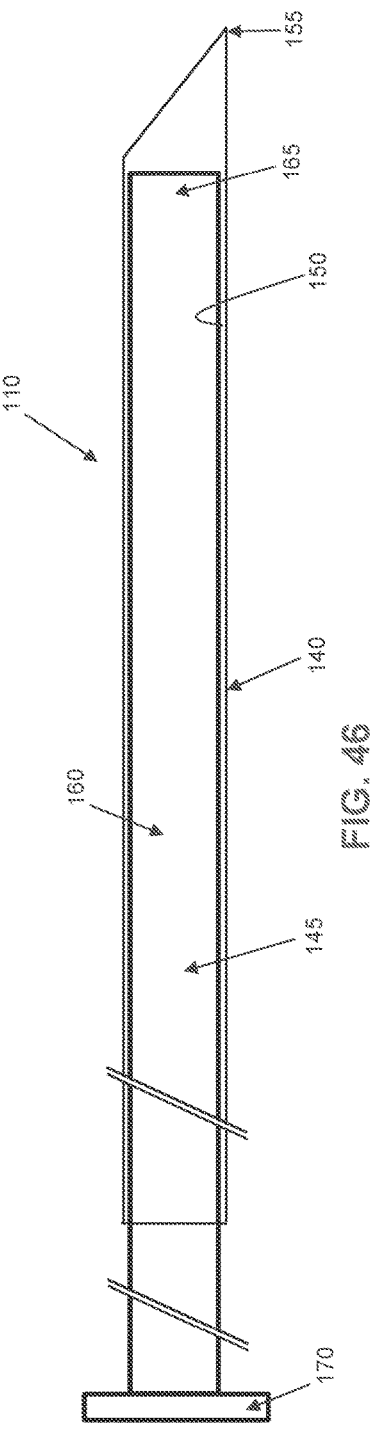

More particularly, and looking now at FIGS. 44-46, bronchoscopic sensor unit 100 (FIG. 44) generally comprises a J-bar and electrical lead assembly 105 (FIG. 45) and a deployment assembly 110 (FIG. 46).

J-bar and electrical lead assembly 105 generally comprises a J-bar assembly 115 and an electrical lead 120. J-bar assembly 115 comprises the aforementioned hook structure 16 which carries the aforementioned fiducial sensor 10 and the aforementioned prongs 20. One end 125 of electrical lead 120 is connected to fiducial sensor 10 such that electrical power delivered to electrical lead 120 can power fiducial sensor 10. The other end 130 of electrical lead 120 comprises an atraumatic tip 135. Electrical lead 120 may be covered with a hydrophobic braided wire to allow for easy insertion and retraction of J-bar and electrical lead assembly 105 through lumen 150 (see below) of deployment assembly 110.

Figure 46A:
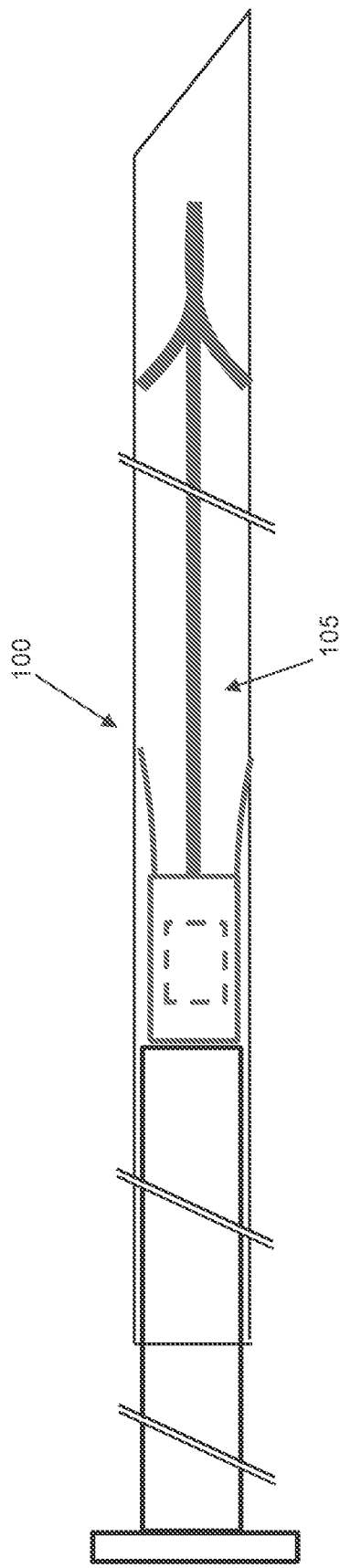
FIGS. 46A and 46B are schematic views showing another apparatus for bronchoscopic deployment of the fiducial sensor into tissue (e.g., bronchoscopic deployment of the fiducial sensor into the tissue mass or adjacent to the tissue mass).
Figure 46B:
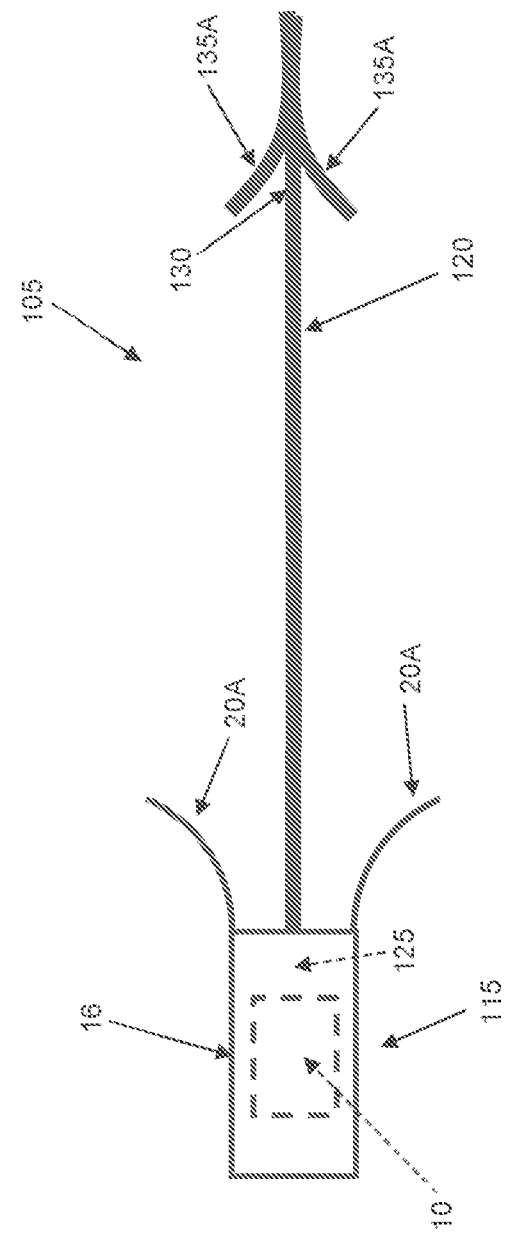
Figure 47:
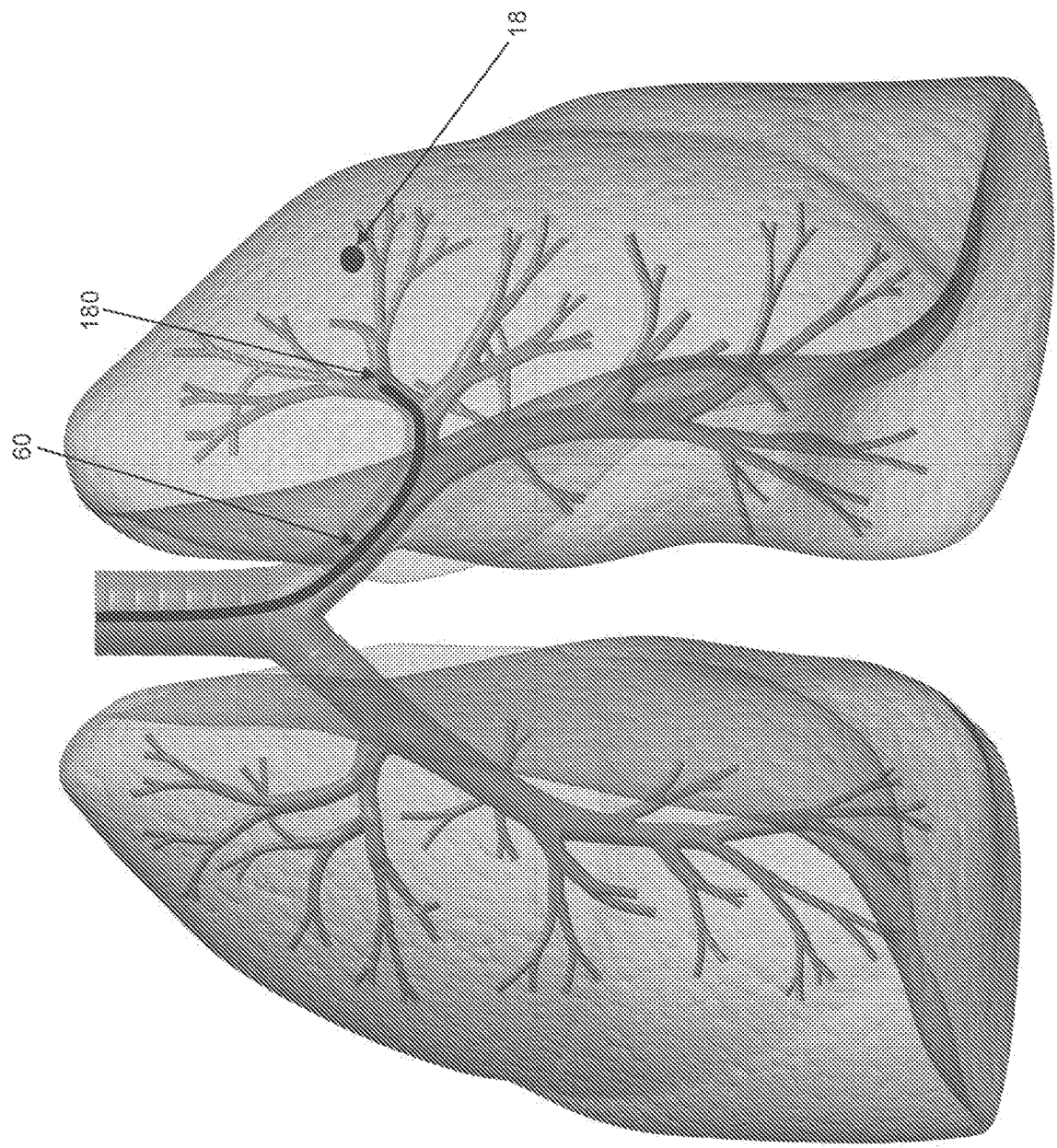
FIGS. 47-52 are schematic views showing how the apparatus of FIGS. 44-46 may be used for bronchoscopic deployment of the fiducial sensor into tissue (e.g., bronchoscopic deployment of the fiducial sensor into the tissue mass or adjacent to the tissue mass).
Figure 48:
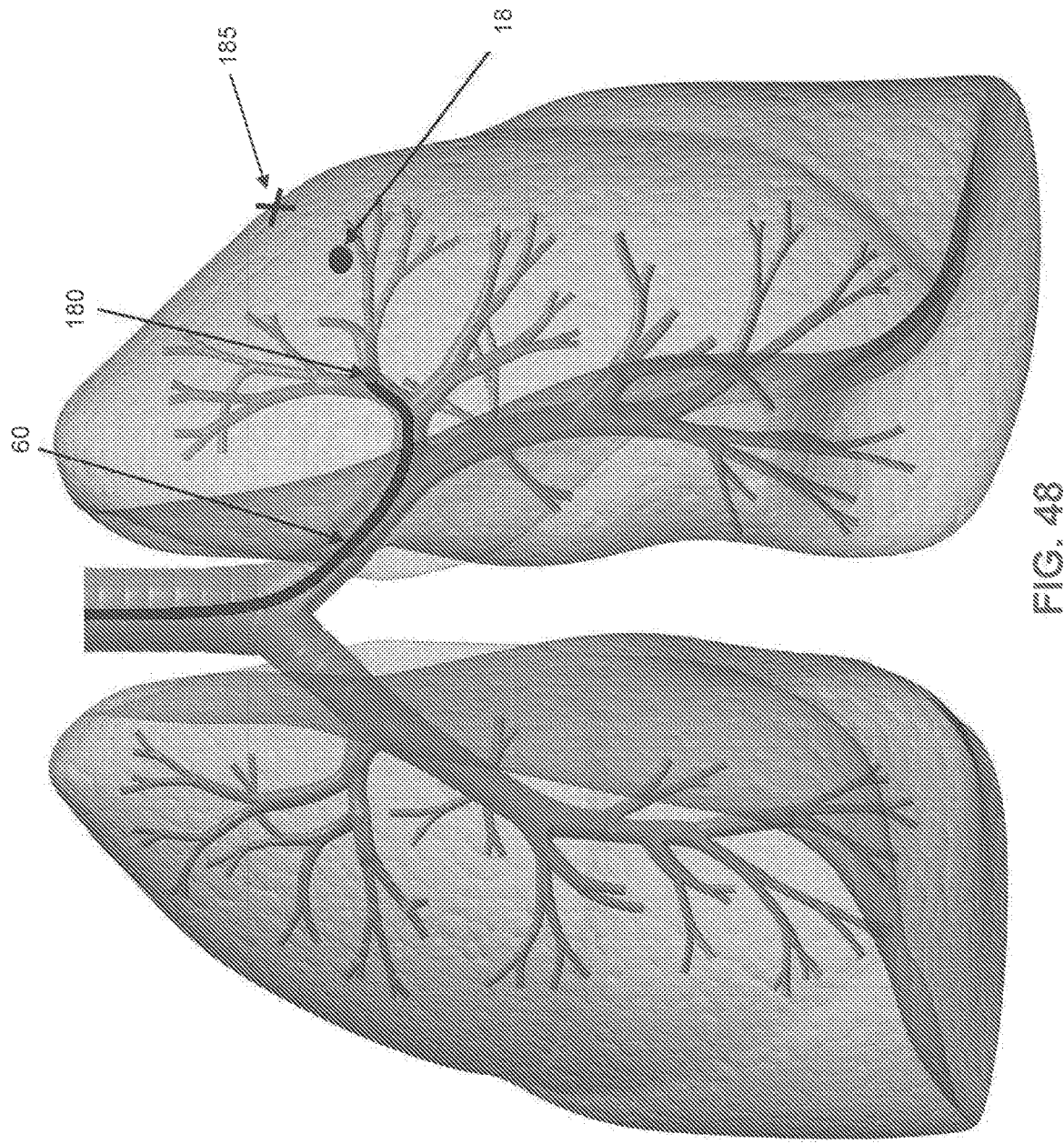
Figure 49:
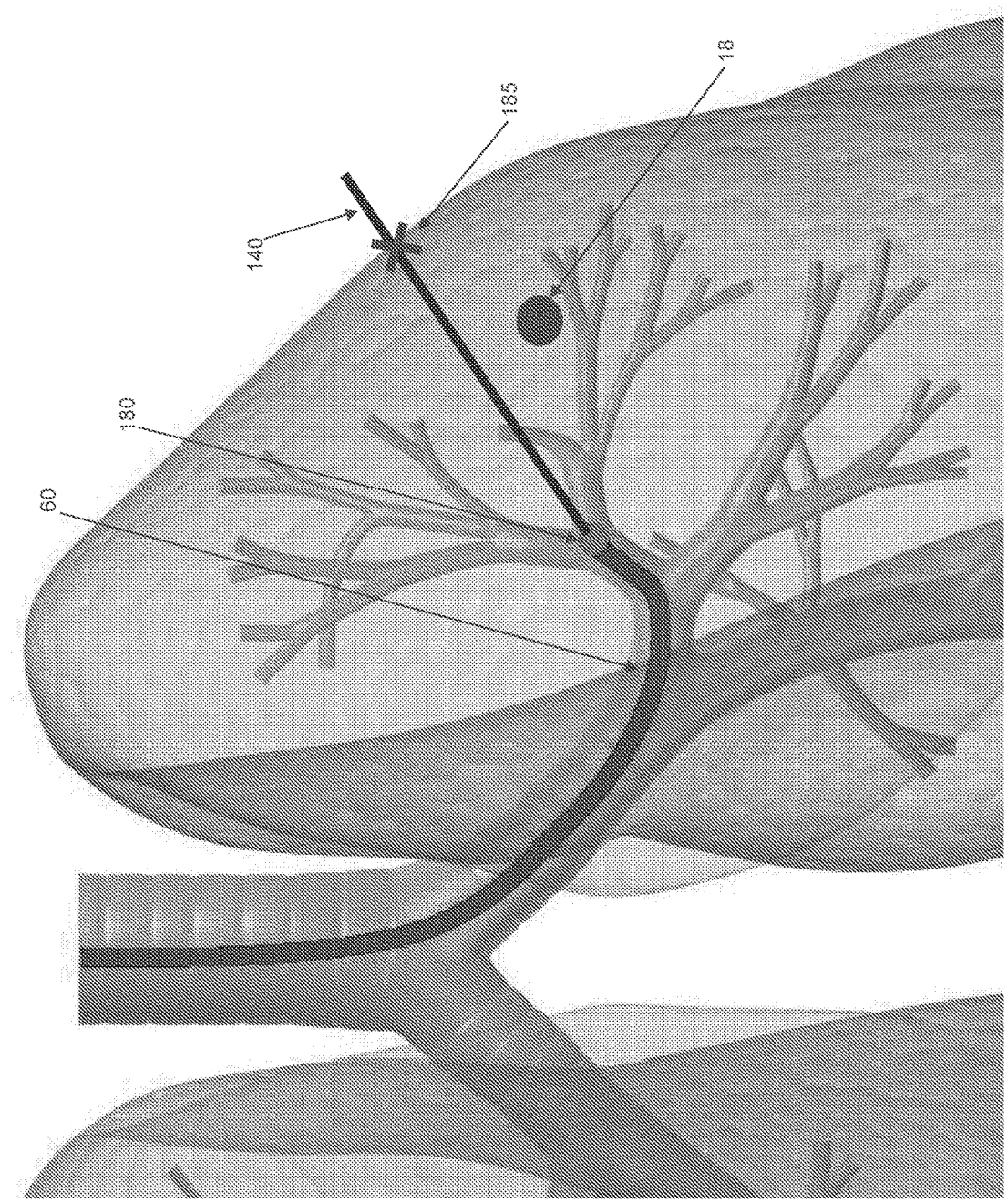
Figure 50:
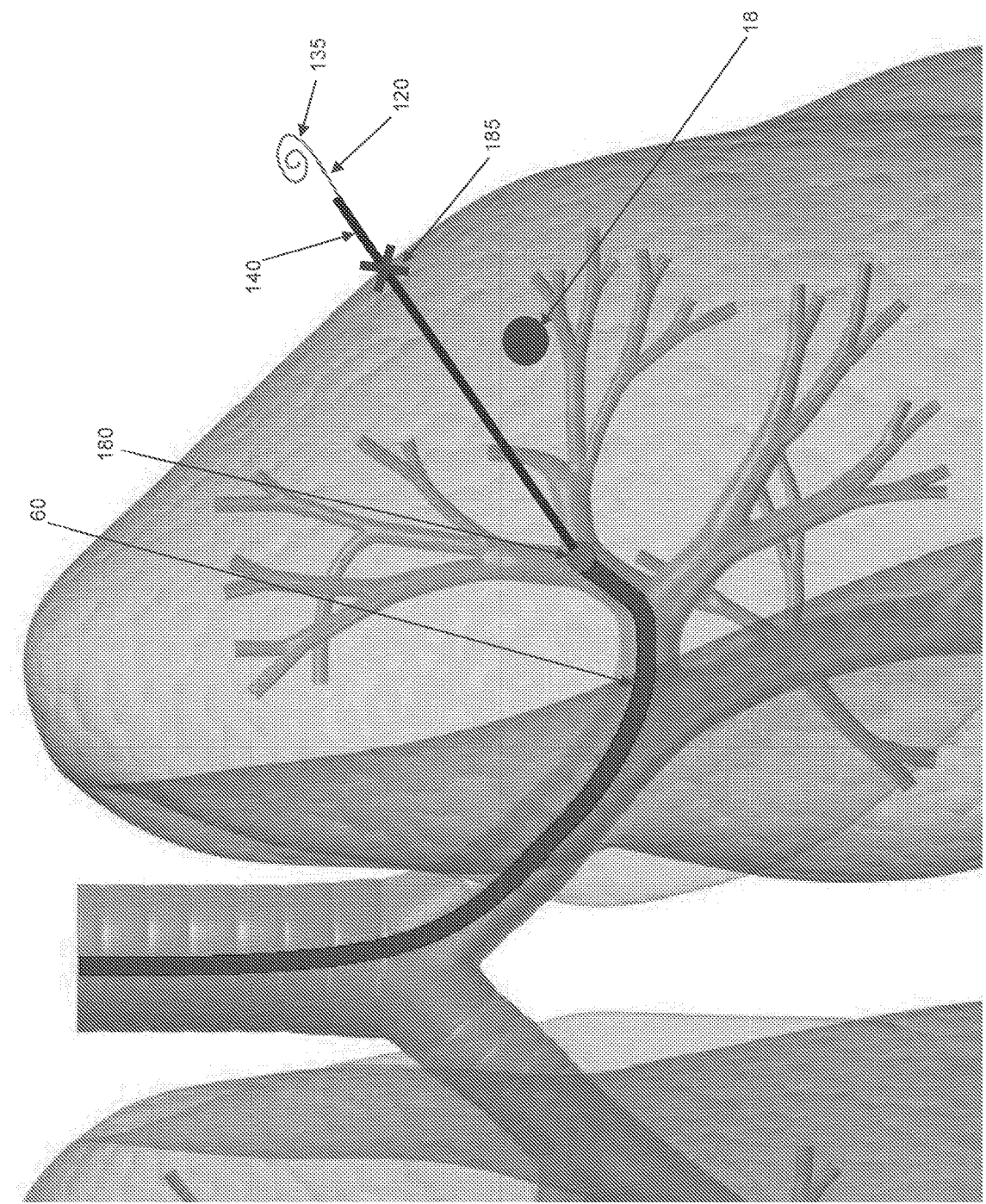
Figure 51:
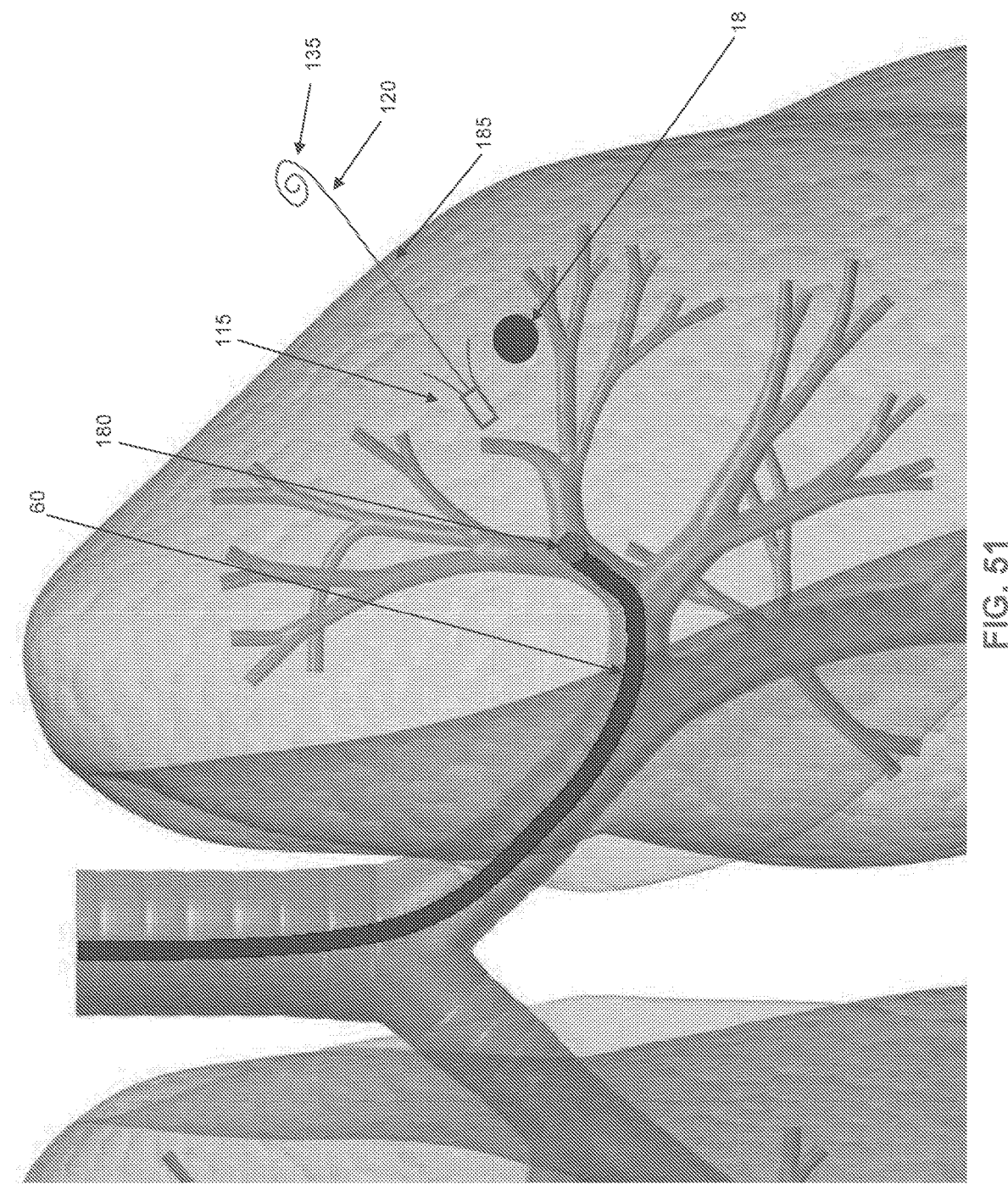

Alternatively, if desired, instead of an atraumatic tip 135, the distal end of J-bar and electrical lead assembly 105 may comprise a second anchor that could prevent electrical lead 120 from re-entering the lung once the distal end of electrical lead 120 has emerged from the lung. In other words, this second anchor would prevent retrograde movement of the distal end of electrical lead 120 after deployment. Furthermore, in such a form of the invention, prongs 120 of J-bar assembly 115 could have a configuration which prevents antegrade movement of J-bar assembly 115 once it is released from deployment assembly 110. See, for example, FIGS. 46A and 46B, which show prongs 135A at the distal end of electrical lead 120, and prongs 20A at the distal end of J-bar assembly 115, with prongs 135A preventing post-deployment proximal movement of the distal end of electrical lead 120 and prongs 20A preventing post-deployment distal movement of J-bar assembly 115.

Deployment assembly 110 comprises a needle cannula 140 and a pusher 145. Needle cannula 140 comprises a hollow lumen 150 and terminates in a sharp tip 155. Pusher 145 comprises a shaft 160. One end of shaft 160 ends in a blunt distal end 165. The other end of shaft 160 terminates in a handle 170. Shaft 160 of pusher 145 is sized to be slidably received in lumen 150 of needle cannula 140. Note that needle cannula 140 of deployment assembly 110 is sized so that it can be inserted through the working channel of a bronchoscope.

As seen in FIG. 44, J-bar and electrical lead assembly 105 and shaft 160 of pusher 145 are initially disposed within lumen 150 of needle cannula 140, with prongs 20 of J-bar assembly 115 being elastically deformed into a straighter configuration so as to be received within lumen 150 of needle cannula 140, and with the proximal ends of the elastically deformed prongs 20 residing just distal to blunt end 165 of pusher 145. Note also that when J-bar and electrical lead assembly 105 is disposed within lumen 150 of needle cannula 140, atraumatic tip 135 of electrical lead 120 is elastically deformed so that it sits substantially straight within needle cannula 140 (note that FIG. 44 is intended to be schematic in nature, and in practice electrical lead 120 has a diameter which more closely fills lumen 150 of needle cannula 140, such that atraumatic tip 135 of electrical lead 120 sits substantially straight when it is confined within needle cannula 140, and returns to the coiled configuration shown in FIG. 45 when atraumatic tip 135 is not confined within needle cannula 140). In this way, needle cannula 140 can carry J-bar and electrical lead assembly 105, with needle cannula 140 shielding J-bar and electrical lead assembly 105 from contact with surrounding structures (e.g., a bronchoscope, tissue, etc.). However, distal movement of pusher 145 can eject J-bar and electrical lead assembly 105 from lumen 150 of needle cannula 140.

In a preferred method of use, the intended position of J-bar and electrical lead assembly 105 vis-à-vis the anatomy of the patient is planned prior to deployment in the lung using diagnostic or intraprocedural CT, C-arm CT, MRI or other imaging modalities, i.e., the intended position of J-bar assembly 115, and the exit point of electrical lead 120 as it emerges from the lung surface, are planned in advance on diagnostic or intraprocedural CT, C-arm CT, MRI or other imaging modalities. The electromagnetic (EM) tracking coordinates are mapped to the diagnostic/intraprocedural imaging coordinates using image registration algorithms well known in the art to track the bronchoscope and J-bar and electrical lead assembly 105 in the imaging coordinates. The position of J-bar assembly 115 is chosen to be in the proximity of the tumor, preferably along the line joining the bronchoscope target position and the exit position of the electrical lead, while the exit point of electrical lead 120 from the lung is chosen to be (i) the shortest path from the J-bar location to the lung surface (or the fissure surface), or (ii) according to surgeon preference.

By way of example but not limitation, in a preferred method of use, and looking now at FIGS. 47-52, a bronchoscope 60 is advanced through the airways of the patient until the distal tip of bronchoscope 60 is disposed near the lesion (i.e., tissue mass) 18. See FIG. 47. Note that bronchoscope 60 may be advanced under direct visualization and its position may be tracked using one or more sensors 180 carried by bronchoscope 60. Alternatively, the position of bronchoscope 60 may be tracked using J-bar assembly 115, provided that a temporary electrical connection is provided for J-bar assembly 115 (i.e., via an electrical connection extending through the interior of needle cannula 140, such as by electrifying a portion of pusher 145). The position of the tracked bronchoscope 60 can be mapped to the imaging coordinates (see above) using image registration algorithms of the sort well known in the art in order to guide the bronchoscope 60 to the lesion 18.

Next, if it has not already been done, a target point 185 is identified on the outer surface of the lung as the point where it is desired that needle cannula 140 will emerge from the lung and enter the pleural space. See FIG. 48.

Then bronchoscopic sensor unit 100 (comprising deployment assembly 110 and its passenger J-bar and electrical lead assembly 105) has its distal end advanced through bronchoscope 60, through the lung, through target point 185 and into the pleural space. See FIG. 49. Note that the distal end of bronchoscopic sensor unit 100 can be guided visually via bronchoscope 60, and/or via scanner visualization (e.g., CT imaging, C-arm imaging, ultrasound imaging, etc.), or by using the temporarily-electrically-connected J-bar assembly 115, if a temporary electrical connection has been established through the interior of needle cannula 140.

Next, pusher 145 of deployment assembly 110 may be used to push J-bar and electrical lead assembly 105 distally so that (i) atraumatic tip 135 and a portion of electrical lead 120 pass out of needle cannula 140 and into the pleural space, and (ii) J-bar assembly 115 is disposed adjacent to lesion 18 (note, however, that at this point J-bar assembly 115 and a portion of electrical lead 120 remain within needle cannula 140). See FIG. 50.

Next, needle cannula 140 is retracted proximally while maintaining pusher 145 in position, thereby exposing (i) the portion of electrical lead 120 extending from target point 185 to J-bar assembly 115, and (ii) J-bar assembly 115. As needle cannula 140 retracts past prongs 20 of J-bar assembly 115, prongs 20 are no longer constrained within lumen 150 of needle cannula 140 and are free to spring outboard and set into the tissue, whereby to anchor J-bar assembly 115 (and hence fiducial sensor 10) adjacent to lesion 18. See FIG. 51. At this point, if J-bar assembly 115 was temporarily connected to electrical power through the interior of needle cannula 140, the wires of the J-bar are disconnected and retracted to within needle cannula 140. Note that this disconnection and retraction of the electrical leads passing through needle cannula 140 is desirable, since it removes them from the intended resection line.

Then a power supply clamping tool 190 is advanced into the pleural space and clamped onto the portion of electrical lead 120 extending out of the lung, whereby to provide electrical power to electrical lead 120 and hence fiducial sensor 10 of J-bar assembly 115. See FIG. 52. Note that by supplying electrical power to J-bar assembly 115 via a power supply clamping tool 190 advanced into the pleural space from a point outside the body (rather than through needle cannula 140 and bronchoscope 60 advanced through the bronchi), the electrical leads do not cross the intended resection line.

Power supply clamping tool 190 can take various forms. In essence, it is an elongated tool which is configured to extend from outside the body into the pleural space, and to make an electrical connection to the portion of electrical lead 120 extending out of the lung and into the pleural space, whereby to deliver power to J-bar assembly 115. By way of example but not limitation, power supply clamping tool 190 may comprise a pair of electrically-connected jaws which can be closed about the portion of electrical lead 120 extending out of the lung and into the pleural space. Note that power supply clamping tool 190 can be deployed either through a needle extending through the skin or through a port created on the skin surface. The power supplied by power supply clamping tool 190 to electrical lead 120 enables J-bar assembly 115 to connect to the EM tracking system.

Once powered, fiducial sensor 10 communicates with the electromagnetic (EM) tracking system and the location of fiducial sensor 10 (and hence the location of lesion 18) can be determined by controller 48.

At this point, a surgical instrument 80 (carrying an instrument sensor 85) can be used to effect the desired resection line in the lung, whereby to excise lesion 18 from the remainder of the lung. Note that J-bar and electrical lead assembly 105 extends from lesion 18 to the pleural space, and hence is contained within the tissue which is being excised, and does not cross the resection line. In other words, J-bar and electrical lead assembly 105 is always outboard of lesion 18. As a result, fiducial sensor 10 of J-bar assembly 115 can remain powered throughout the resection procedure, does not interfere with the resection procedure, and J-bar and electrical lead assembly 105 is carried away with the resected tissue after resection has been completed.

As noted above, in one form of the invention, a bronchoscope 60 is advanced through the airways of the patient until the distal tip of bronchoscope 60 is disposed near the lesion (i.e., tissue mass) 18. As also noted above, the bronchoscope 60 may be advanced under direct visualization and its position may be tracked using one or more sensors 180 carried by bronchoscope 60. Alternatively, the position of bronchoscope 60 may be tracked using J-bar assembly 115, provided that a temporary electrical connection is provided for J-bar assembly 115 (i.e., via an electrical connection extending through the interior of needle cannula 140, such as by electrifying a portion of pusher 145). Thus, it can be desirable to provide a temporary electrical connection for J-bar assembly 115 (i.e., via an electrical connection extending through the interior of needle cannula 140, such as by electrifying a portion of pusher 145) so that J-bar assembly 115 can be powered while the J-bar assembly is in needle cannula 140.

It can also be desirable to provide a temporary electrical connection for J-bar assembly 115 (i.e., via an electrical connection extending through the interior of needle cannula 140, such as by electrifying a portion of pusher 145) so that J-bar assembly 115 can be powered prior to connecting power supply clamping tool 190 to the portion of the electrical lead 120 extending out of the lung.

Figure 52:
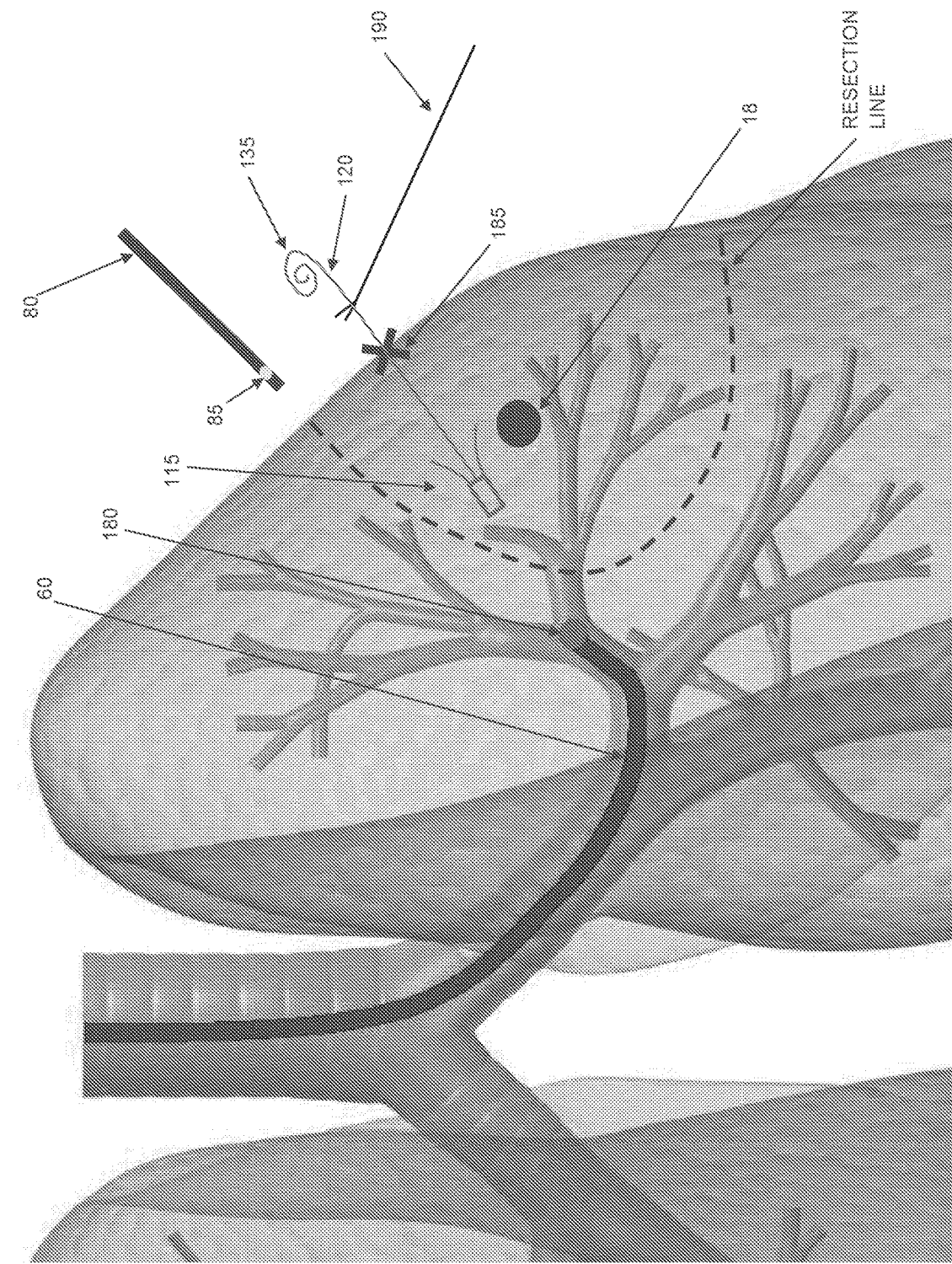
Figure 52A:
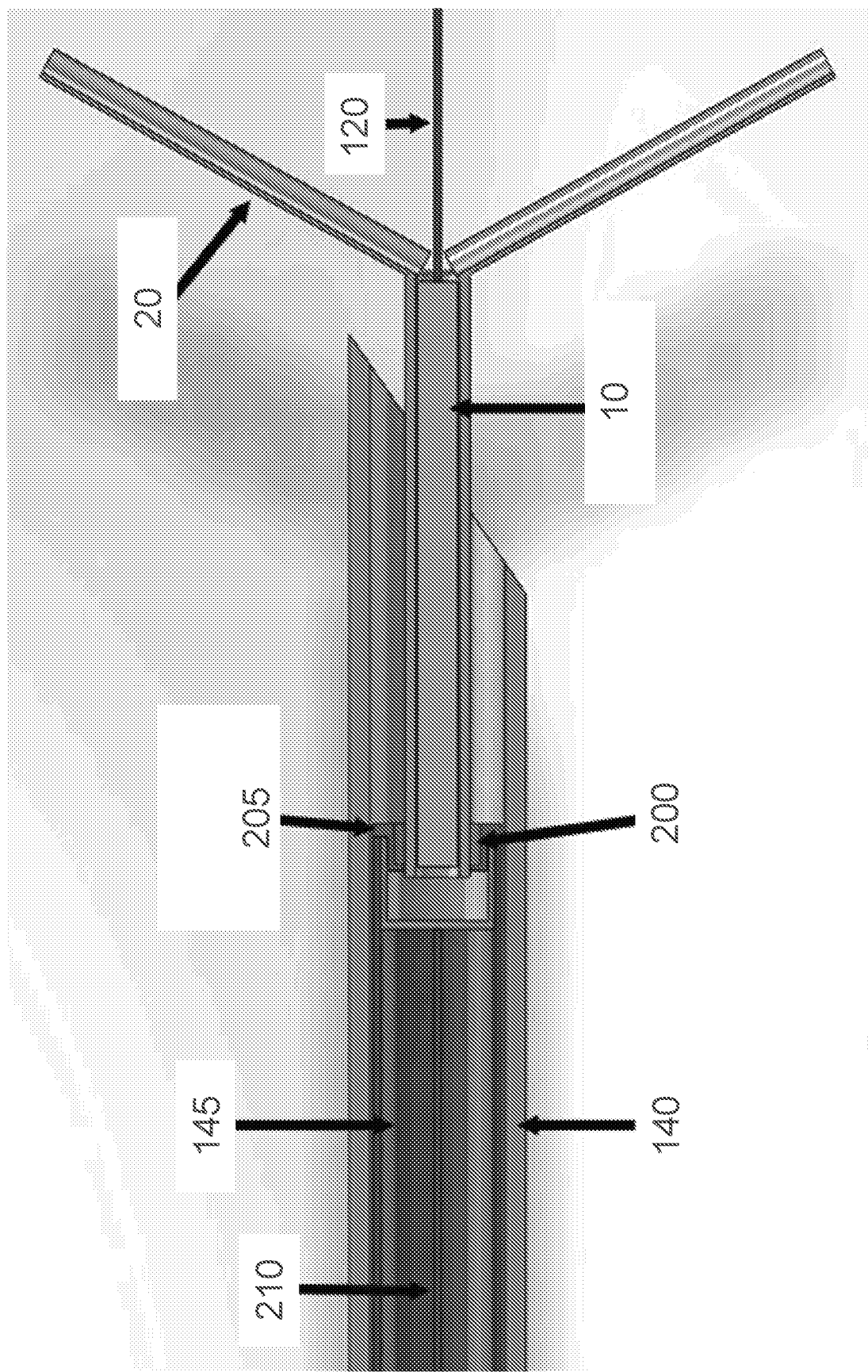
FIG. 52A is a schematic view showing how a temporary proximal electrical connection may be provided for the fiducial sensor, e.g., such as when the fiducial sensor is deployed through a bronchoscope.

In one preferred form of the invention, and looking now at FIG. 52A, a temporary electrical connection for J-bar assembly 115 can be provided as follows. Fiducial sensor 10 of J-bar assembly 115 comprises a proximal electrical connector 200 (as well as the electrical lead 120, which extends distally from fiducial sensor 10). Pusher 145 is cannulated and comprises a distal electrical connector 205. Electrical power is provided to distal electrical connector 205 of pusher 145 by a wire 210 which extends through pusher 145 (and which connects to a power source, not shown). While J-bar assembly 115 is seated in needle cannula 140, proximal electrical connector 200 of J-bar assembly 115 is connected to distal electrical connector 205 of pusher 145, whereby to power fiducial sensor 10. After J-bar assembly 115 has been deployed in the anatomy of a patient (and after prongs 20 have set in the tissue), pusher 145 is retracted, separating distal electrical connector 205 of pusher 145 from proximal electrical connector 200 of J-bar assembly 115, thereby disconnecting J-bar assembly 115 from the power supplied by wire 210 extending through pusher 145. However, it will be appreciated that power may still be delivered to J-bar assembly 115 via electrical lead 120 and power supply clamping tool 190 (connected to electrical lead 120).

Stapler Articulation Measurement

Surgical stapler heads can be articulated about a pivot point 220 to provide the desired orientation while resecting the lesion. While the instrument sensor 28 may be placed on the articulating head of the surgical stapler 26 (e.g., such as is shown in FIGS. 8 and 9), this can cause interference from ferromagnetic material on the stapler head. Therefore, in practice, the instrument sensor 28 is typically positioned on the shaft of the surgical stapler 26, just proximal to the articulation point, e.g., about 10 cm from the stapler tip, in order to avoid interference from ferromagnetic material on the stapler head. In this position, the instrument sensor 28 is proximal to the pivot point 220 on the surgical stapler 26, so that the instrument sensor 28 sits on the non-articulating portion of the stapler 26. See FIG. 53. As a result, the instrument sensor 28 placed on the non-articulating portion of the surgical stapler 26 does not capture the articulation motion of the surgical stapler 26.

Therefore, in another form of the invention, the surgical stapler 26 is configured to measure the articulation angle of the stapler head. More particularly, an articulation sensor 225 is provided which preferably comprises two parts. The first part 230 of the articulation sensor 225 is placed on the stapler shaft. The second part 235 of the articulation sensor 225 is placed on the articulating stapler head. The connection between the first and second parts 230, 235 of the articulation sensor 225 is through a flexible encoder circuit that measures the angulation of the articulating end of the stapler head. The encoder circuit is preferably a modified circular potentiometer to measure the angulation of the stapler head. See FIG. 54. A Wheatstone bridge circuit measures the variable resistance produced on the encoder circuit so as to estimate the stapler articulation angle. In addition, the surgical stapler 26 may also include an LED indicator (not shown) on the stapler shaft to confirm the placement of the articulation sensor 225 on the surgical stapler 26. Once the articulation sensor 225 is placed on the surgical stapler 26, the circuit is completed to light up the LED indicator.

If desired, the articulation sensor 225 may use schemes other than electrical resistance to measure stapler head articulation, e.g., an optical encoder may be used to measure stapler head articulation, or a magnetic encoder may be used to measure stapler head articulation, etc. The articulation sensor 225 can also be internalized to the specific working internal of the stapler device 26. Alternatively, a second sensor (not shown) can be placed on an elastic extension from the sleeve towards the tip and past the articulation to allow direct measurement of the stapler articulation angle. This extension may be secured with tape or other adhesive.

Marking The Boundary Of A Resection Margin And Stapler Positioning

In one form of the invention, the lesion will be segmented from the diagnostic CT imaging so as to create a 3D model of the lesion 240 that will be inputted to the navigation system. In another form of the invention, the lesion may be segmented based on a direct visualization of the lesion by the surgeon, with or without input from radiologic findings. Based on input from the surgeon or a machine learning algorithm, the resection margin will be determined. A segmented model for the resection margin 245 is generated by expanding the lesion label map by the desired resection margin. See FIGS. 55 and 56. With knowledge of the position of the fiducial sensor (e.g., the T-bar or J-bar assembly) and the lesion model 240, the position of the tracked surgical stapler can be precisely estimated with respect to the lesion model 240 and the estimated resection margin model 245.

Figure 57:
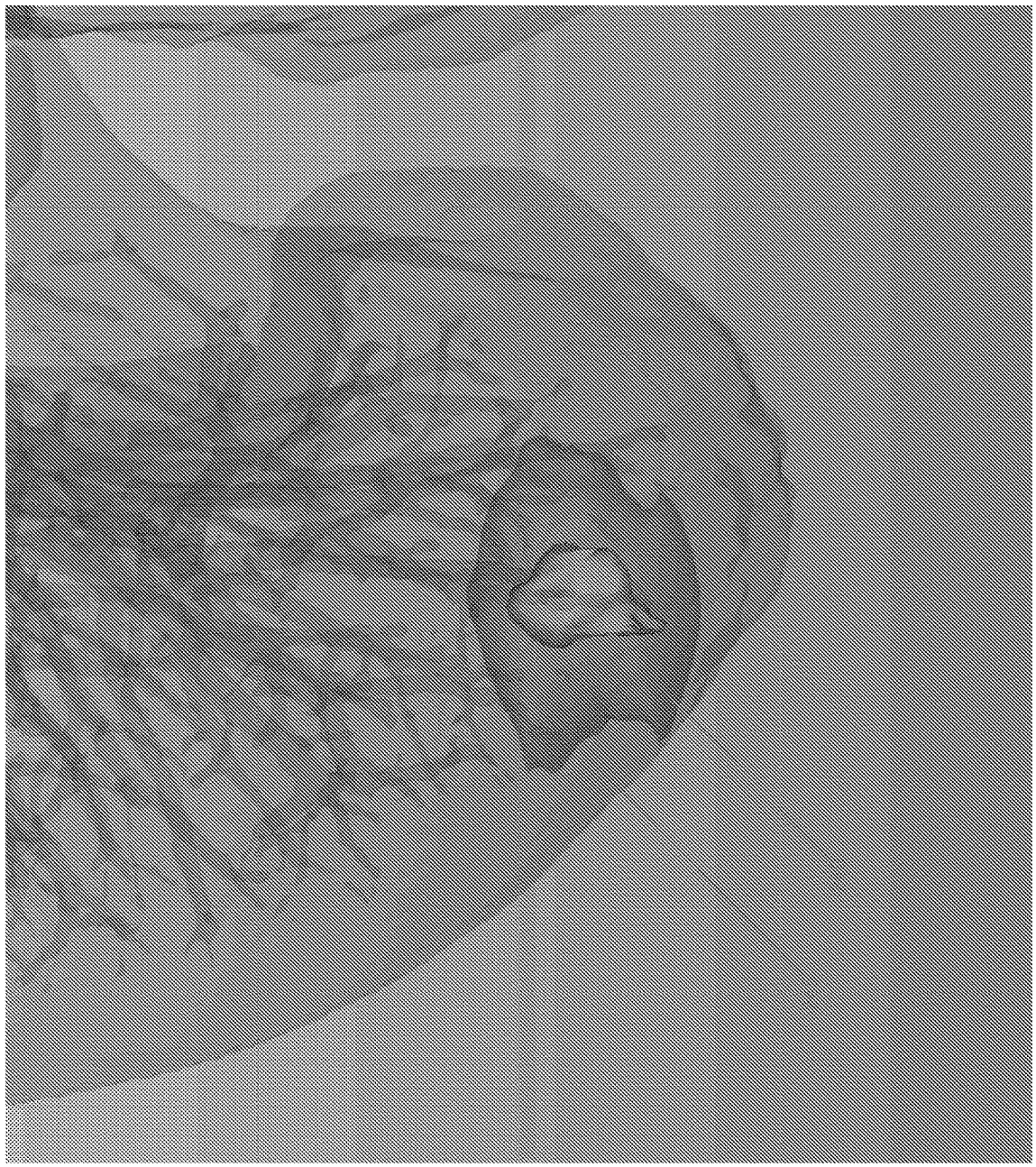
FIGS. 57-60 are schematic views showing how staples may be deployed adjacent to the resection margin of a lesion.
Figure 58:
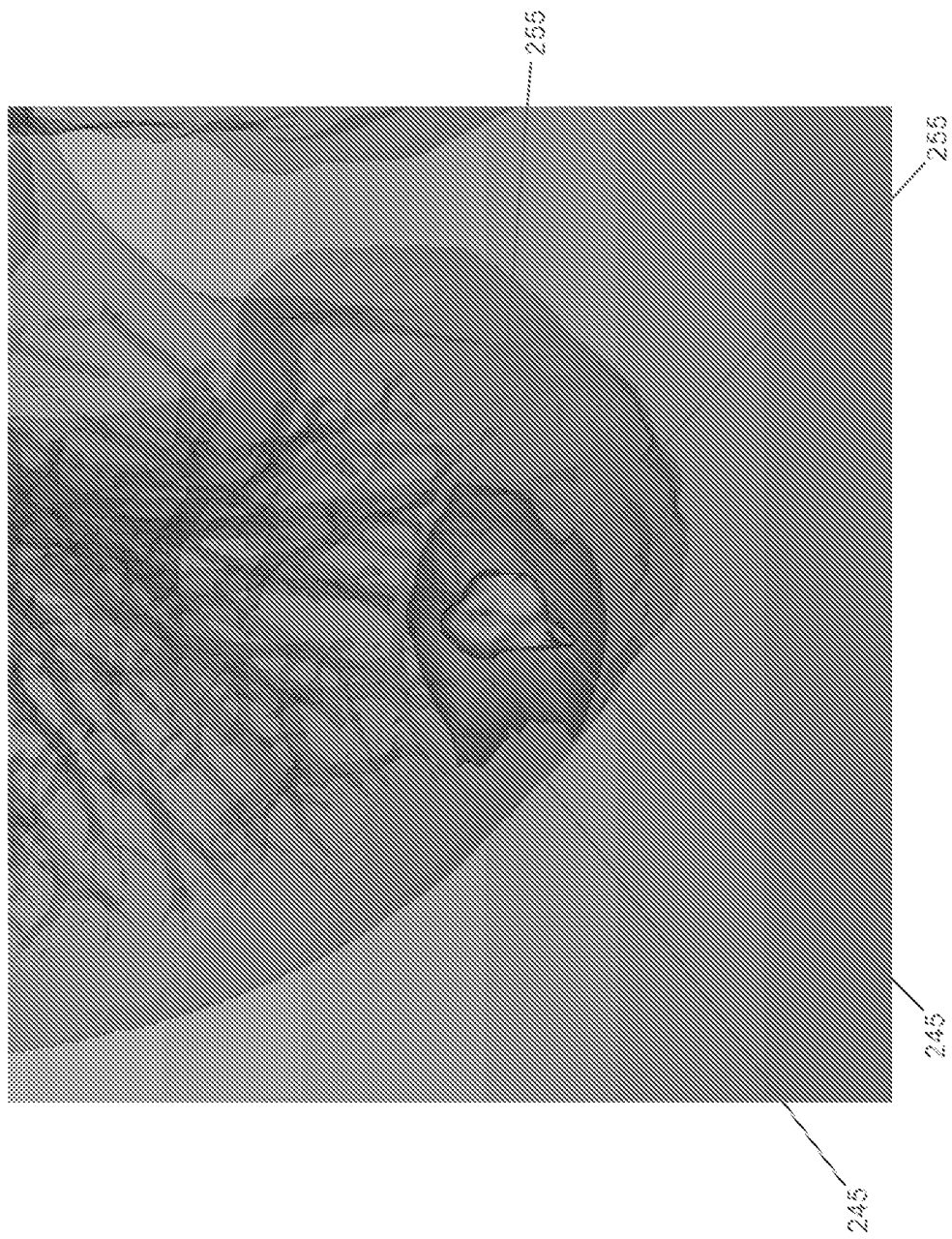
Figure 59:
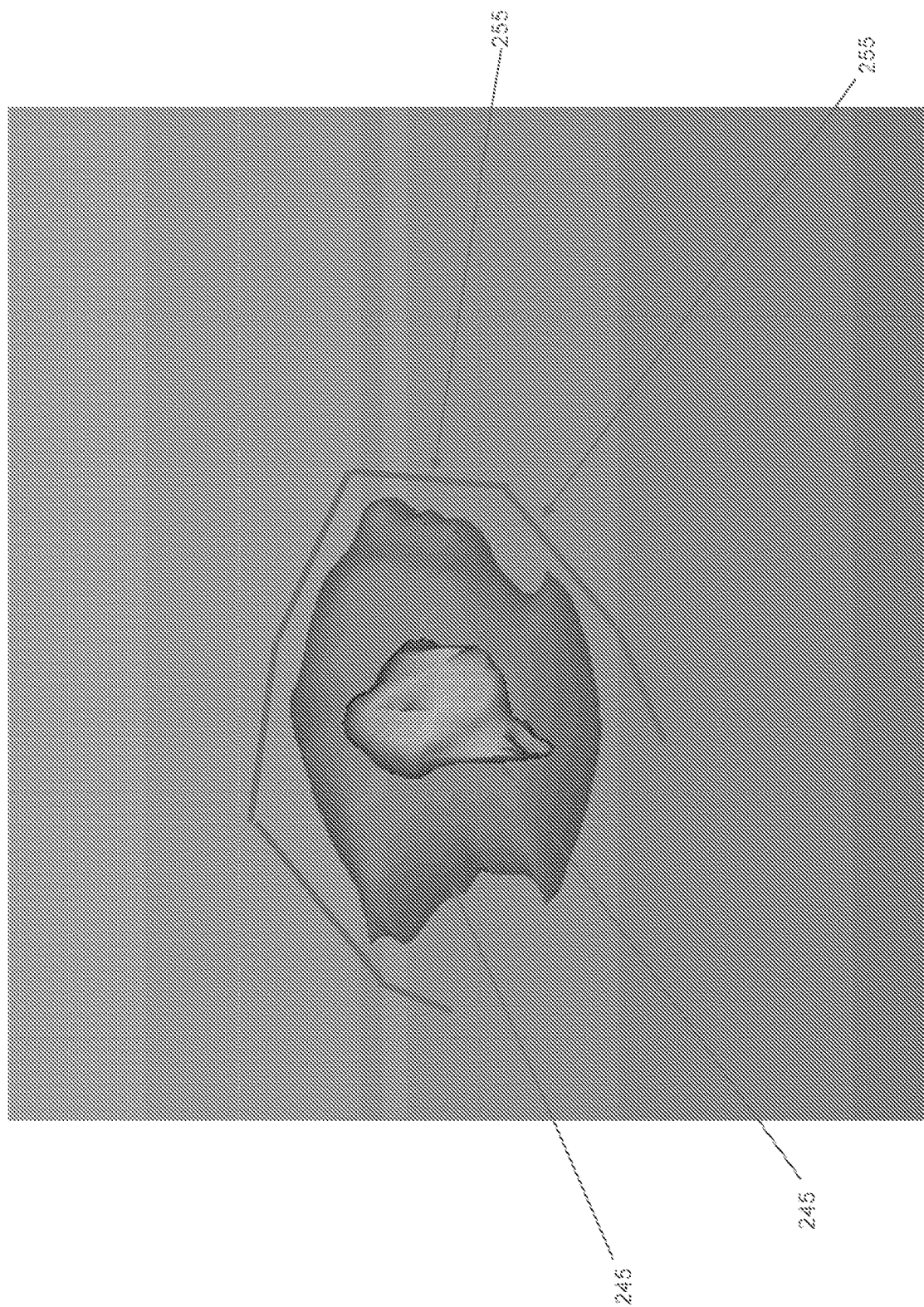
Figure 60:
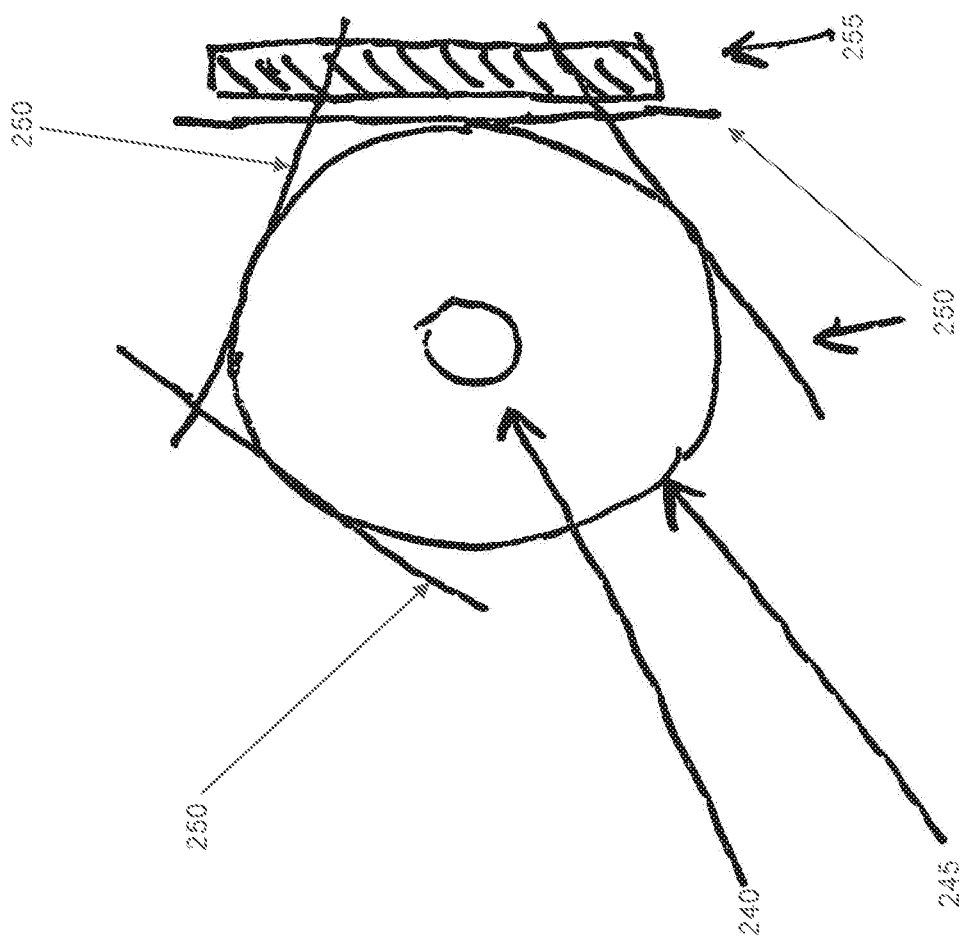

In addition to the foregoing, in one form of the invention, the navigation software can guide the surgeon to precisely resect around the lesion, based on a distance to secure a sufficient margin defined by the surgeon based on the mass size and presumed diagnosis. See FIGS. 57-59. More particularly, in one form of the invention, and looking now at FIG. 60, the navigation software computes the tangent lines 250 at the perimeter of the modeled resection margin 245, and then guides the surgeon to place the staples 255 just outside those tangent lines 250, so that the staples 255 follow a tangential path around the estimated resection margin model 245.

Although the above described system and method for resecting a tissue mass was described for surgery involving the lung, it is also applicable to resection of lesions in any other organ or structure of the body, for example, resection for breast conserving surgery, liver resection, sarcoma resection, partial nephrectomy or lung wedge resection surgery. In addition, the above described system and method for resecting a tissue mass is not limited to VATS or minimally invasive surgery.

What is claimed is:

1. A method for tracking a tissue mass disposed in or on an anatomical structure, wherein the anatomical structure comprises at least one lumen, the method comprising:
   advancing a scope along the at least one lumen until the distal end of the scope is disposed in the vicinity of the selected tissue mass;
   advancing a fiducial sensor through the scope, into the anatomical structure, and securing the fiducial sensor to the anatomical structure in the vicinity of the tissue mass; and
   detecting the position of the fiducial sensor within the anatomical structure,
   wherein the fiducial sensor is part of a sensor assembly, and further wherein the sensor assembly comprises the fiducial sensor and an electrical lead extending distally from the fiducial sensor, with the electrical lead preceding the fiducial sensor as the fiducial sensor advances through the scope.

2. A method according to claim 1 wherein the sensor assembly is advanced through the scope and into the anatomical structure using a deployment assembly which comprises a needle cannula and a pusher.

3. A method according to claim 2 wherein the sensor assembly is slidably disposed within the needle cannula, the needle cannula is advanced through the scope in order to advance the sensor assembly through the scope, and the sensor assembly is deployed out of the needle cannula and into the anatomical structure by advancing the pusher relative to the needle cannula or by retracting the needle cannula relative to the pusher.

4. A method according to claim 3 wherein the electrical lead is passed through an outer surface of the anatomical structure.

5. A method according to claim 4 wherein the electrical lead is passed through an outer surface of the anatomical structure before the sensor assembly is deployed out of the needle cannula and into the anatomical structure.

6. A method according to claim 5 wherein the needle cannula extends through an outer surface of the anatomical structure while the electrical lead is disposed within the needle cannula.

7. A method according to claim 6 wherein, after the distal portion of the electrical lead is carried through an outer surface of the anatomical structure, the needle cannula is retracted so as to expose the distal portion of the electrical lead extending through an outer surface of the anatomical structure.

8. A method according to claim 7 wherein the sensor assembly is released from the needle cannula and engages the anatomical structure after the distal portion of the electrical lead extends through an outer surface of the anatomical structure.

9. A method according to claim 4 wherein a surgical navigation system is used to determine the location where the electrical lead extends through an outer surface of an anatomical structure.

10. A method according to claim 9 wherein the surgical navigation system uses tracking of the fiducial sensor to determine the location where the electrical lead is to extend through an outer surface of an anatomical structure.

11. A method according to claim 1 wherein the electrical lead comprises a hydrophobic braided wire.

12. A method according to claim 1 wherein the electrical lead comprises an atraumatic tip.

13. A method according to claim 1 wherein the electrical lead comprises at least one barb which restricts proximal movement of the electrical lead.

14. A method according to claim 1 wherein the fiducial sensor comprises at least one barb which restricts distal movement of the fiducial sensor.

15. A method according to claim 1 wherein the electrical lead comprises at least one barb which restricts proximal movement of the electrical lead and wherein the fiducial sensor comprises at least one barb which restricts distal movement of the fiducial sensor.

16. A method according to claim 1 wherein the sensor assembly further comprises a proximal electrical lead for powering the fiducial sensor, wherein the proximal electrical lead extends through the scope while the fiducial sensor is advanced through the scope and secured to the anatomical structure in the vicinity of the tissue mass.

17. A method according to claim 16 wherein the fiducial sensor is tracked as the scope is inserted along the at least one lumen.

18. A method according to claim 16 wherein the fiducial sensor is tracked as the fiducial sensor is advanced through the scope, into the anatomical structure, and secured to the anatomical structure in the vicinity of the tissue mass.

19. A method according to claim 16 wherein the method further comprises, after the fiducial sensor is secured to the anatomical structure, detaching the proximal electrical lead from the sensor assembly after the sensor assembly is deployed in the anatomical structure.

20. A method according to claim 16 wherein the method further comprises, after the fiducial sensor is secured to the anatomical structure, powering the fiducial sensor through the electrical lead extending distally from the fiducial sensor.

21. A method for tracking a tissue mass disposed in or on an anatomical structure, wherein the anatomical structure comprises at least one lumen, the method comprising:

providing a sensor assembly comprising a fiducial sensor and an electrical lead extending distally from the fiducial sensor, and providing a deployment assembly comprising a needle cannula and a pusher, wherein the sensor assembly is slidably disposed in the needle cannula distal to the pusher;

advancing a scope along the at least one lumen until the distal end of the scope is disposed in the vicinity of the selected tissue mass;

advancing the needle cannula through the scope, into the anatomical structure, and through an outer surface of the anatomical structure;

retracting the needle cannula so as to expose a portion of the electrical lead extending through the outer surface of the anatomical structure;

supplying electrical power to the fiducial sensor via the electrical lead extending through the outer surface of the anatomical structure;

securing the fiducial sensor to the anatomical structure in the vicinity of the tissue mass by advancing the pusher relative to the needle cannula or by retracting the needle cannula relative to the pusher; and detecting the position of the fiducial sensor within the anatomical structure.

22. A method according to claim 21 wherein the sensor assembly further comprises a proximal electrical lead for powering the fiducial sensor, wherein the proximal electrical lead is releasably attached to the fiducial sensor and extends through the pusher while the fiducial sensor is disposed in the needle cannula, and further wherein the proximal electrical lead powers the fiducial sensor while the fiducial sensor is disposed in the needle cannula.

23. A method according to claim 22 wherein the proximal electrical lead is detached from the fiducial sensor after electrical power is supplied to the fiducial sensor via the distal electrical lead.

* * * * *